US009839214B2

(12) United States Patent
Goldblum et al.

(10) Patent No.: US 9,839,214 B2
(45) Date of Patent: Dec. 12, 2017

(54) SOLAVETIVONE AND 5-EPI-BETA-VERTIVONE AS PEST REPELLANTS AND PESTICIDES

(71) Applicant: EVOLVA, INC., Lexington, KY (US)

(72) Inventors: Seth Goldblum, San Diego, CA (US); Craig B. Warren, San Diego, CA (US)

(73) Assignee: Evolva, Inc., Lexington, KY (US)

(*) Notice: Subject to any disclaimer, the term of this patent is extended or adjusted under 35 U.S.C. 154(b) by 0 days.

(21) Appl. No.: 14/653,017

(22) PCT Filed: Dec. 16, 2013

(86) PCT No.: PCT/US2013/075492

§ 371 (c)(1), (2) Date: Jun. 17, 2015

(87) PCT Pub. No.: WO2014/099821

PCT Pub. Date: Jun. 26, 2014

(65) Prior Publication Data

US 2016/0174552 A1 Jun. 23, 2016

Related U.S. Application Data

(60) Provisional application No. 61/797,965, filed on Dec. 18, 2012.

(51) Int. Cl.
*A01N 35/00* (2006.01)
*A01N 35/06* (2006.01)

(52) U.S. Cl.
CPC .................................... *A01N 35/06* (2013.01)

(58) Field of Classification Search
CPC ...................................................... A01N 35/06
USPC ......................................................... 514/691
See application file for complete search history.

(56) References Cited

U.S. PATENT DOCUMENTS

| | | | |
|---|---|---|---|
| 2,423,284 | A | 7/1947 | Babbini |
| 2,954,347 | A | 9/1960 | Griebstein et al. |
| 2,954,348 | A | 9/1960 | Schwoeppe |
| 3,352,664 | A | 11/1967 | Nolan et al. |
| 3,377,249 | A | 4/1968 | Marco |
| 3,396,223 | A | 8/1968 | Stark |
| 3,515,782 | A | 6/1970 | Nolan |
| 3,516,941 | A | 6/1970 | Matson |
| 3,707,503 | A | 11/1970 | Terrence |
| 3,884,828 | A | 5/1975 | Butler |
| 3,892,680 | A | 7/1975 | Benjamin et al. |
| 3,915,343 | A | 10/1975 | Barcock |
| 3,929,663 | A | 12/1975 | Arai et al. |
| 3,936,538 | A | 2/1976 | Marshall et al. |
| 3,970,584 | A | 7/1976 | Hart et al. |
| 4,009,114 | A | 2/1977 | Yurko |
| 4,062,937 | A | 12/1977 | Rea |
| 4,145,184 | A | 3/1979 | Brain et al. |
| 4,304,680 | A | 12/1981 | Wixon |
| 4,308,279 | A | 12/1981 | Smeltz |
| 4,376,784 | A | 3/1983 | Harney et al. |
| 4,520,142 | A | 5/1985 | Leinen |
| 4,528,226 | A | 7/1985 | Sweeney |
| 4,566,980 | A | 1/1986 | Smith |
| 4,581,385 | A | 4/1986 | Smith et al. |
| 4,681,806 | A | 7/1987 | Matkan et al. |
| 4,948,013 | A | 8/1990 | Thomas et al. |
| 5,043,090 | A | 8/1991 | Camp et al. |
| 5,413,795 | A | 5/1995 | Lee et al. |
| 5,425,891 | A | 6/1995 | Pujol et al. |
| 5,434,189 | A | 7/1995 | Steltenkamp |
| 5,472,686 | A | 12/1995 | Tsubaki et al. |
| 5,571,901 | A | 11/1996 | Boeck et al. |
| 6,048,892 | A | 4/2000 | Iwasaki et al. |
| 6,180,594 | B1 | 1/2001 | Fender et al. |
| 6,415,992 | B1 | 7/2002 | Blondeel et al. |
| 6,495,193 | B2 | 12/2002 | Hiramoto et al. |
| 6,521,589 | B2 | 2/2003 | Demeyere et al. |
| 6,531,303 | B1 | 3/2003 | Millis et al. |
| 6,574,883 | B2 | 6/2003 | Giblin et al. |
| 6,689,593 | B2 | 2/2004 | Millis et al. |
| 6,875,732 | B2 | 4/2005 | Jurek et al. |
| 6,930,082 | B2 | 8/2005 | Harichian et al. |
| 7,354,892 | B2 | 4/2008 | Bastigkeit et al. |
| 7,387,992 | B2 | 6/2008 | Hsu et al. |
| 7,622,614 | B2 | 11/2009 | Julien et al. |
| 7,648,953 | B2 | 1/2010 | Bastigkeit et al. |

(Continued)

FOREIGN PATENT DOCUMENTS

| | | |
|---|---|---|
| GB | 2073132 | 10/1980 |
| JP | 0881306 | 3/1996 |

(Continued)

OTHER PUBLICATIONS

Jain et al., "Insect Repellents From Vetiver Oil: Zizanal and Epizizanl", Tetrahedron Letters, vol. 23, No. 45, pp. 4639-4642 (1982).*

Alves et al., "Effects of Controlled Atmospheres on Production of Sesquiterpenoid Stress Metabolites by White Potato Tuber: Possible Involvement of Cyanide-resistant Respiration," Plant Physiol. 63(2):359-62 (Feb. 1979).

Back & Chappell, "Cloning and bacterial expression of a sesquiterpene cyclase from Hyoscyamus muticus and its molecular comparison to related terpene cyclases," J Biol Chem. 270(13):7375-81 (Mar. 1995).

Blount & Williams, "Revised structure of xanthochymol," Tetrahedron Letters 34:2921-4 (1976).

Corry et al., "Enhanced recovery of solavetivone from Agrobacterium transformed root cultures of Hyoscyamus muticus using integrated product extraction," Biotechnol Bioeng. 42(4):503-8 (Aug. 1993).

(Continued)

*Primary Examiner* — Kevin E Weddington

(74) *Attorney, Agent, or Firm* — McDonnell Boehnen Hulbert & Berghoff LLP

(57) ABSTRACT

Provided are pest control compositions, including pest repellent and pesticidal compositions, containing solavetivone, 5-epi-P-vetivone or a derivative or analog thereof, alone or in combination with one or more additional active ingredients. Also provided are formulations containing the compositions and methods of use.

44 Claims, 1 Drawing Sheet

(56) References Cited

U.S. PATENT DOCUMENTS

| | | | |
|---|---|---|---|
| 7,838,037 | B2 | 11/2010 | Kvitnitsky et al. |
| 7,838,279 | B2 | 11/2010 | Millis et al. |
| 7,842,497 | B2 | 11/2010 | Millis et al. |
| 7,863,236 | B2 | 1/2011 | Kaschig et al. |
| 7,910,534 | B2 | 3/2011 | Muller et al. |
| 7,910,538 | B2 | 3/2011 | Tang et al. |
| 7,928,050 | B2 | 4/2011 | Schneiderman et al. |
| 7,951,768 | B2 | 5/2011 | Boutique et al. |
| 7,989,413 | B2 | 8/2011 | Ogden et al. |
| 7,994,112 | B2 | 8/2011 | Vanpachtenbeke et al. |
| 2010/0129306 | A1 | 5/2010 | Julien et al. |

FOREIGN PATENT DOCUMENTS

| | | |
|---|---|---|
| WO | 9917871 | 4/1999 |
| WO | 2006079020 | 7/2006 |

OTHER PUBLICATIONS

Coxon et al., "Two new vetispirane derivatives: Stress metabolites from potato (*Solanum tuberosum*) tubers," Tetrahedron Letters 15(34):2921-4 (1974).

Da Silva et al., "1,2,3,4-tetrahydro-2-methyl-β-carboline and solavetivone from Solanum jabrense," Biochemical Systematics and Ecology 30:1083-5 (2002).

Fradin & Day, "Comparative efficacy of insect repellents against mosquito bites," N Engl J Med. 347(1):13-8 (Jul. 2002).

Fujimori et al., "Isolation of solavetivone from Nicotiana tabacum," Phytochemistry 16(3):392 (1977).

GenBank Accession No. U20187, dated Mar. 7, 2000 (2 pages).

Greenhagen et al., "Probing sesquiterpene hydroxylase activities in a coupled assay with terpene synthases," Arch Biochem Biophys. 409(2):385-94 (Jan. 2003).

Guedes et al., "Accumulation of six sesquiterpenoid phytoalexins in tobacco leaves infiltrated with Pseudomonas lachrymans," Phytochemistry 21(12):2987-8 (1980).

Hanus et aL, "Substances isolated from *Mandragora* species," Phytochemistry 66(20):2408-17 (Oct. 2005).

Hwu and Wetzel, "Silicon-promoted ring contractions in the formation of carbocyclic spiro compounds. Total synthesis of (-)-solavetivone," J Org Chem. 57(3):922-8 (1992).

Iwata et al., "Effects of neighbouring hydroxy-groups in metal-ammonia reductions of aβ-unsaturated carbonyl compounds," Journal of the Chemical Society, Chemical Communications 10: 463-5 (1981).

Jain et al., "Insect repellents from vetiver oil: I. zizanal and epizizanal," Tetrahedron Letters 23(45):4139-42 (Jan. 1982).

Kawauchi et al., "Production of sesquiterpene-type phytoalexins by hairy roots of Hyoscyamus albus co-treated with cupper sulfate and methyl jasmonate," Chem Pharm Bull (Tokyo) 58(7):934-8 (Jul. 2010).

Kuroyanagi et al., "Phytoalexins from hairy roots of Hyoscyamus albus treated with methyl jasmonate," J Nat Prod. 61(12):1516-9 (Dec. 1998).

Lee et al., "Microencapsulation of fragrant oil via in situ polymerization: effects of pH and melamine-formaldehyde molar ratio," J Microencapsul. 19(5):559-69 (Sep.-Oct. 2002).

Miguel & Barroso, "Accumulation of stress metabolites in cell suspension cultures of Hyoscyamus albus," Phytochemistry 35(2):371-5 (Jan. 1994).

Murai et al., "Biosyntesis from solavetivone of the phytoalexin rishitin potato. Implicit role of solavetivone as an activator," Journal of the Chemical Society, Chemical Communications 1:32-3 (1982).

Murai et al., "π-Cyclization: The synthesis of (±)-solavetivone and (±)-hinesol," Tetrahedron Letters 22(11):1033-6 (1981).

Nagase et al., "Sesquiterpenoids from the Roots of Solanum aethiopicum," Z Naturforsch C 56:181-7 (2001).

Nishikawaji et al., "Sesquiterpenoids from flue-cured tobacco leaves," Phytochemistry 22(8):1819-20 (1983).

Pompon et al., "Genetically engineered yeast cells and their applications," Toxicol Lett. 82-83:815-22 (1995).

Priya & Padmakumari, "HPTLC and reverse phase HPLC methods for the simultaneous quantification and in vitro screening of antioxidant potential of isolated sesquiterpenoids from the rhizomes of Cyperus rotundus," J Chromatogr B Analyt Technol Biomed Life Sci. 904:22-8 (Sep. 2012).

Ribera & Zuniga, "Induced plant secondary metabolites for phytopatogenic fungi control: a review," J. Soil Sci. Plant Nutr. 12(4):893-11 (Jan. 2012).

Ro et al., "Loblolly pine abietadienol/abietadienal oxidase PtAO (CYP720B1) is a multifunctional, multisubstrate cytochrome P450 monooxygenase," Proc Natl Acad Sci USA 102(22):8060-5 (May 2005).

Sabater-Jara et al., "Induction of sesquiterpenes, phytoesterols and extracellular pathogenesis-related proteins in elicited cell cultures of Capsicum annuum," J Plant Physiol 167(15):1273-81 (Oct. 2010).

Sannai et al., "Isolation of (-)-1,2-dehydro-α-cyperone and solavetivone from Lycium chinense," Phytochemistry 21 (12):2986-7 (1980).

Srikrishna et al., "Enantiospecific total synthesis of phytoalexins, (+)-solanascone, (+)-dehydrosolanascone, and (+)-anhydro-β-rotunol," Tetrahedron Letters 46(43):7373-6 (Oct. 2005).

Stoessl et al., "Sesquiterpenoid stress compounds of the solanaceae," Phytochemistry 15(6):855-72 (1976).

Syu et al., "Cytotoxic and novel compounds from Solanum indicum," J Nat Prod. 64(9):1232-3 (Sep. 2001).

Takahashi et al., "Metabolic engineering of sesquiterpene metabolism in yeast," Biotechnol Bioeng. 97(1):170-81 (May 2007).

Takahashi et al., "Functional characterization of premnaspirodiene oxygenase, a cytochrome P450 catalyzing regio- and stereo-specific hydroxylations of diverse sesquiterpene substrates," J Biol Chem. 282(43):31744-54 (Oct. 2007).

Takemoto et al., "Total synthesis of (-)-solavetivone using enantioselective copper-catalysed conjugate addition of Me3Al to a cyclohexa-2,5-dienone intermediate," Chem Commun. 14:1655-6 (1996).

Takemoto et al., "Diastereoselective total synthesis of (-)-solavetivone via a copper-catalyzed conjugate addition of Me3Al to a cyclohexa-2,5-dienone intermediate," Tetrahedron 53(2):606-16 (Jan. 1997).

Tugizimana et al., "Ergosterol-induced sesquiterpenoid synthesis in tobacco cells," Molecules 17(2):1698-715 (Feb. 2012).

Uegaki et al., "Phytuberol from Nicotiana rustica inoculated with tobacco mosaic virus," Phytochemistry 19(6): 1229-30 (1980).

Yamada et al., "Total synthesis and stereostructure of (±)-solavetivone, a stress metabolite from infected potato tubers; X-ray crystal and molecular structure of an intermediate in the synthesis ," Journal of the Chemical Society, Chemical Communications 16:554-5 (1977).

Yao et al., "Effect of mycorrhization on the accumulation of rishitin and solavetivone in potato plantlets challenged with Rhizoctonia solani," Mycorrhiza 13(6)333-6 (Dec. 2003).

Yokose et al., "Anti-fungal sesquiterpenoid from the root exudate of Solanum abutiloides," Biosci Biotechnol Biochem. 68(12)2640-2 (Dec. 2004).

International Search Report by the International Searching Authority for International Application No. PCT/US2013/075492, dated Jul. 21, 2014 (pp. 1-4).

Written Opinion of the International Searching Authority for International Application No. PCT/US2013/075492, dated Jul. 21, 2014 (pp. 1-5).

International Preliminary Report on Patentability by the International Preliminary Examining Authority for International Application No. PCT/US2013/075492, dated Mar. 25, 2015 (pp. 1-44).

* cited by examiner

A.
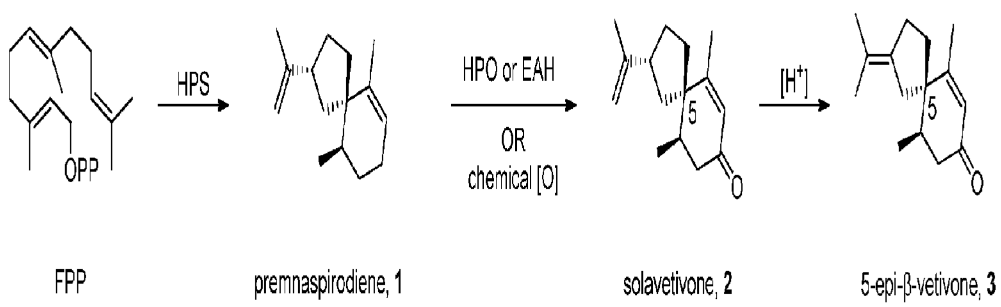
B.
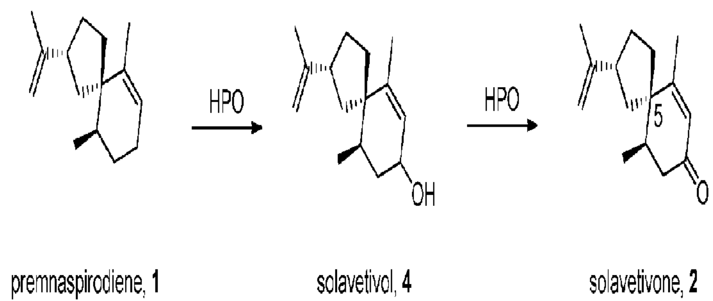

SOLAVETIVONE AND 5-EPI-BETA-VERTIVONE AS PEST REPELLANTS AND PESTICIDES

RELATED APPLICATIONS

This application is a national stage application under 35 U.S.C. §371 of International Application No. PCT/US2013/075492, filed Dec. 16, 2013, which claims the benefit of U.S. Provisional Application Ser. No. 61/797,965, filed Dec. 18, 2012, entitled "SOLAVETIVONE AND 5-EPI-BETA-VETIVONE AS PEST REPELLANTS AND PESTICIDES." The subject matter of the above-noted applications are incorporated by reference in their entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file is 13.1 kilobytes in size, and titled 233SEQPC1.txt.

FIELD OF THE INVENTION

Provided are pest, including insect, control methods, including pest repellent and pesticidal compositions, containing solavetivone and/or 5-epi-β-vetivone and/or derivatives and analogs thereof, alone or in combination with one or more other active ingredients.

BACKGROUND

Pests are organisms, such as insects and small organisms, that can be detrimental to animals, including humans, domesticated animals and pets, and to plants, because of their ability to transmit deadly diseases, cause physical harm, such as bites and rashes, and/or destroy property, including crops, homes and possessions. Chemical-based insect repellants, which can be applied to skin, clothing, or in the immediate surroundings of a person, are available, but these can be harmful to humans and/or animals. Further, resistance to such chemicals can develop. Natural-substance based pesticides that are considered safe to humans and the environment are available, but such substances have proven difficult and/or expensive to provide in commercial qualities. Thus, among the objects herein, is the provision of pest control compositions for use as pesticides and pest repellants that are safe and effective and can be manufactured with minimal environmental impact.

SUMMARY

Provided herein are methods for repelling or killing pests or insects by contacting the pests with solavetivone, 5-epi-β-vetivone or a derivative or analog thereof, or mixtures thereof. In the provided methods, pests are repelled, incapacitated, deterred, eliminated, alleviated, mitigated, reduced in number, eradicated or killed when the pests come into contact with the composition or formulation, or vapors of the composition or formulation, containing the solavetivone, 5-epi-β-vetivone or a derivative or analog thereof, or mixtures thereof. Also provided are pest or insect repellent compositions containing solavetivone, 5-epi-β-vetivone or a derivative or analog of either, or mixtures thereof in a concentration sufficient to repel a pest or insect. Also provided herein are pesticide or insecticide compositions containing solavetivone, 5-epi-β-vetivone or a derivative or analog of either, or mixtures thereof in a concentration sufficient to kill a pest or insect. The solavetivone, 5-epi-β-vetivone or a derivative or analog of either, or mixtures thereof, can be formulated as aerosol propellant pressurized sprayable pest repellent and pesticide products, cleansing compositions, fabric treatment sheet products, liquid fabric treatment compositions, fabric refresher spray compositions and moist towelette products.

Provided herein is a method for repelling or killing pests or insects by contacting a pest or insect with solavetivone, 5-epi-β-vetivone or a derivative or analog of either, or mixtures of any of the foregoing, whereby the pest or insect is repelled or killed. For example, provided herein is a method for repelling or killing insects or pests by providing an amount of a composition containing solavetivone, 5-epi-β-vetivone or a derivative or analog thereof of either or mixtures thereof to a location in which the pest or insect occurs, wherein the amount is sufficient to repel or kill the pests or insects; and deploying the composition at the location, whereby the pest or insect is repelled from the location or dies after coming in contact with the composition or vapors from the composition.

In some examples of the provided method, the solavetivone, 5-epi-β-vetivone or a derivative or analog thereof is present in an amount sufficient to kill pests or insects. In one example, an amount sufficient to kill insects or pests is an amount of at least at or at least about 0.1% solavetivone, 5-epi-β-vetivone or a derivative or analog thereof, by weight, of the composition. In some examples of the provided methods, the solavetivone, 5-epi-β-vetivone or a derivative or analog thereof is present in an amount between at least or at least about 0.1% and at or about 100%, or between at or about 0.1% and at or about 50%, or between at or about 0.1% and at or about 25%, or between at or about 0.1% and at or about 20%, or between at or about 0.1% and at or about 10%, by weight, of the composition. For example, the solavetivone, 5-epi-β-vetivone or a derivative or analog thereof is present in an amount of at least or at least about 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 99%, or 100%, by weight, of the composition.

In some examples of the provided methods for killing or repelling pests, the derivative or analog of solavetivone is selected from among 3-hydroxysolavetivone, 3,9-dihydroxysolavetivone, 3-hydroxy-9-(3-methyl-2-butenoyloxy)solavetivone, 3-acetoxysolavetivone, 13-hydroxysolavetivone, 3-acetoxy-9-(2-methylpropionyloxy)solavetivone, 3-hydroxy-9-(3-methylbutanoyloxy)solavetivone, 3-acetoxy-9-(3-methyl-butanoyloxy)-solavetivone, 3-acetoxy-9-(3-methyl-2-butenoyloxy)solavetivone, 3-hydroxy-9-tigloyloxysolavetivone, 3-hydroxy-9-isobutanoyloxysolavetivone, 3-beta-acetoxysolavetivone and 3-beta-hydroxysolavetivone.

In the provided methods for repelling or killing pests, the solavetivone, 5-epi-β-vetivone or a derivative or analog thereof is deployed by applying topically, atomizing, brushing on, coating, dipping, drenching, dripping, dusting, foaming, infusing, injecting into or onto, pouring, rolling on, scattering, spraying, spreading, sprinkling or wiping the composition onto at least a portion of the location. In some examples, the location is surface of the body of a human or animal. For example, the surface is the skin, hair or fur of a human or animal. In some examples, the composition is deployed by applying topically to the skin or hair of a human. In other examples, the composition is deployed by applying topically to the skin, hair or fur of an animal, such as a companion animal. In yet other examples, the composition is deployed by spraying or applying topically to an article of clothing of a human. In some examples, the composition is deployed by laundering an article of clothing of a human with a composition that is provided as a detergent or fabric softener or both. The fabric softener can be a liquid fabric softener, a fabric softening rinse or a fabric softening gel. In other examples, the composition is deployed by drying an article of clothing of a human with a composition that is provided as a fabric softener sheet.

In the provided methods for repelling or killing pests, the composition can be provided as an aerosol, a solution, an emulsion, an oil, a lotion, a soap, a spray or a gel. In some examples of the method, the composition is provided as a skin conditioner, hand lotion, body lotion, facial lotion, skin moisturizer, skin toner, skin sanitizer, skin cleansing composition, skin soothing and lubricating composition, sunscreen product, hair conditioner, hair styling gel, hair anti-dandruff composition, hair lotion, hair tonic, rinse, conditioner, hair anti-frizzing agent composition, hair shining composition, mousse, styling gel, hair pomade product, hair spray, soap, foaming bath product, hand cleanser, body cleanser, facial cleanser, astringent cleanser, anti-acne product, body shampoo, body wash, synthetic detergent bar, shower gel, anti-aging product, tanning product, self-tanning product, after-sun product, masking product, anti-wrinkle product, hair growth promoter composition, hair colorant composition or shampoo.

In some examples of the provided methods for killing or repelling pests, the location is a bedding location, such as bedding, bed boards, bed slats, a mattress, box springs, furniture, carpeting, baseboards and flooring, or a combination thereof. In other examples, the composition is deployed by applying the composition to bedding, bed boards, bed slats, a mattress, box springs, furniture, carpeting, baseboards or flooring or a combination thereof. For example, provided herein is a method for killing or repelling pests wherein a composition containing solavetivone, 5-epi-β-vetivone or a derivative or analog thereof of either or mixtures thereof is provided to a location in which the pest or insect occurs, wherein the amount is sufficient to repel or kill the pests or insects and the composition is deployed by spraying the composition onto the surface of bedding, bed boards, bed slats, a mattress, box springs, furniture, carpeting, baseboards or flooring; injecting the composition into the mattress, box springs, furniture, carpeting, baseboards or flooring; or any combination of spraying or injecting, whereby the pest or insect is repelled from the location or dies after coming in contact with the composition or vapors from the composition.

In some examples of the provided methods for killing or repelling insects, the composition is formulated to form a viscous fluid or gel when dispensed and applied to the insect or pest. In other examples, the composition is an absorbent substrate or gel that is deployed in the vicinity of bed boards, bed slats, a mattress, box springs, furniture or carpeting so that vapors from the composition come into contact with a surface of the bed boards, bed slats, a mattress, box springs, furniture or carpeting. In a specific example the composition is deployed by injecting the composition into a wall space.

In some examples, the location is a wood structure, wooden object or wall space. In other examples, the location is selected from among an air supply duct, an attic, an awning, a basement, a cellar, a crawlspace, a deck, a dock, a garage, a hamper, a heating vent, a home foundation, a linen storage closet, a pool deck, roof tiles, a shipping container, a storage unit, a suitcase, a walkway and a wall space. In yet other examples, the location is an animal that is selected from among a bovine, canine, caprine, cervine, cricetine, feline, galline, equine, lapine, murine, musteline and ovine.

In some examples of the provided methods for killing or repelling insects, the pests or insects are selected from among a Siphonaptera insect, cat flea (*Ctenocephalides felis*), dog flea (*Ctenocephalides canis*), oriental rat flea (*Xenopsylla cheopis*), human flea (*Pulex irritans*), chigoe (*Tunga penetrans*), European rat flea (*Nosopsyllus fasciatus*), Anoplura insect, head louse (*Pediculus humanus capitis*), crab louse (*Pthirus pubis*), short-nosed cattle louse (*Haematopinus eurysternus*), sheep louse (*Dalmalinia ovis*), hog louse (*Haematopinus suis*), long-nosed cattle louse (*Linognathus vituli*), cattle biting louse (*Bovicola bovis*), poultry shaft louse (*Menopon gallinae*), poultry body louse (*Menacanthus stramineus*), little blue cattle louse (*Solenopotes capillatus*), *Haematopinus* spp., *Linognathus* spp., *Pediculus* spp., *Phtirus* spp., *Solenopotes* spp., Acarina insect, bush tick (*Haemaphysalis longicornis*), *Haemaphysalis flava, Dermacentor taiwanicus*, American dog tick (*Dermacentor variabilis*), *Ixodes ovatus, Ixodes persulcatus*, black legged tick (*Ixodes scapularis*), lone star tick (*Amblyomma americanum*), *Boophilus microplus, Rhipicephalus sanguineus, Ixodes holocyclus*, western black legged tick (*Ixodes pacificus*), *Dermacentor andersoni, Amblyomma maculatum*, ear mite (*Octodectes cynotis*), *Psoroptes* spp., *Chorioptes* spp., *Otodectes* spp., *Sarcoptes* spp., *Notoedres* spp., *Knemidocoptes* spp., *Sacroptes scabiei, Demodex* spp., follicle mite (*Demodex canis*), northern fowl mite (*Ornithonyssus sylviarum*), poultry red mite (*Dermanyssus gallinae*), *Trombicula* spp., *Leptotrombidium akamushi, Ornithodorus hermsi, Ornithodorus turicata, Ornithonyssus bacoti, Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Cytodites* spp., *Laminosioptes* spp., Heteroptera insect, common bedbug (*Cimex lectularius*), tropical bedbug (*Cimex hemipterus*), *Reduvius senilis, Triatoma* spp., *Rhodnius* spp., *Panstrongylus* spp., *Arilus critatus*, Mallophage (Amblycera and Ischnocera) insect, *Trimenopon* spp., *Menopon* spp., *Trinoton* spp., *Bovicola* spp., *Werneckiella* spp., *Lepikentron* spp., *Trichodectes* spp. and *Felicola* spp. In one example, the pest or insect is selected from among ants, bedbugs, carpet beetles, centipedes, chiggers, drain flies, dust mites, earwigs, fleas, flies, gnats, hornets, lice, millipedes, mites, mosquitoes, scabies, silverfish, spiders, stinkbugs, termites, ticks, wasps, weevils and yellow jackets. For example, the pests or insects are ants which are selected from among Argentine ants, black ants, carpenter ants, fire ants, odorous house ants, pavement ants and pharaoh ants. In other examples, the pest or insect are lice that are selected from among head lice, body lice, pubic lice and nits thereof.

In some examples of the provided methods for killing or repelling pests and insects, the composition is formulated for delivery of solavetivone, 5-epi-β-vetivone or a derivative, analog or mixtures thereof for a period of time selected from among at least 1 hour, 2 hours, 3 hours, 4 hours, 5 hours, 6, hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, at least 1 day, 2 days, 3 days, 4 days, 5 days, 6 days 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, at least 45 days, at least 60 days, at least 75 days, at least 90 days, at least 4 months, at least 5 months, at least 6 months, at least 7 months, at least 8 months, at least 9 months, at least 10 months, at least 11 months and at least 1 year.

In some examples of the provided methods for killing or repelling insects, the composition containing the solavetivone, 5-epi-β-vetivone or a derivative or analog thereof of either or mixtures thereof further contains a carrier that is present in an amount between at least or at least about 0.1% and least or at least about 99.9%, or between at least or at least about 10% and at least or at least about 80%, or between at least or at least about 20% and at least or at least about 70%, or between at least or at least about 30% and at least or at least about 60%, or between at least or at least about 10% and at least or at least about 40%, or between at least or at least about 30% and at least or at least about 70%, or between at least or at least about 60% and at least or at least about 90%, by weight, of the composition. In some examples, the carrier is selected from among water, an alcohol, an aldehyde, an alkane, an alkene, an amide, an amine, a diglyceride, an ester, an ether, a glycol ether, a fat, a fatty acid, a glycol ester, a ketone, lanolin, mineral oil, a monoglyceride, paraffin oil, a polyethylene glycol, petrolatum, a propylene carbonate, silicone, tall oils, a terpene hydrocarbon, a terpene alcohol, a triglyceride, finely divided organic solid material, finely divided inorganic solid materials and mixtures thereof. For example, the carrier contains an alcohol selected from among an aromatic alcohol, a $C_1$-$C_6$ monohydric alcohol, $C_2$-$C_6$ polyhydric alcohol, a polyvalent alcohol, and mixtures thereof. In another example, the carrier contains an oil selected from among almond oil, avocado oil, canola oil, cashew oil, cherry seed oil, cocoa butter, coconut oil, corn oil, cottonseed oil, flaxseed oil, grape seed oil, jojoba oil, macadamia nut oil, olive oil, palm oil, palm fruit oil, peanut oil, rapeseed oil, rice bran oil, safflower oil, sesame oil, soybean oil, sunflower oil, and walnut oil and combinations thereof. In yet another example, the carrier contains diethyl ether, isopropyl ether, n-propyl ether, or a combination thereof.

In another example, the carrier contains ethylene glycol, ethylene glycol monomethyl ether, ethylene glycol dimethyl ether, methylene glycol, methylene glycol monomethyl ether, methylene glycol dimethyl ether, propylene glycol, propylene glycol monomethyl ether, propylene glycol dimethyl ether, butylene glycol, butylene glycol monomethyl ether, butylene glycol dimethyl ether, or combinations thereof. In one example, the carrier contains acetone, methyl ketone, methyl benzyl ketone, methyl ethyl ketone, methyl isopropyl ketone, methyl butyl ketone, ethyl ketone, benzyl methyl ketone, or combinations thereof. In a different example, the carrier contains finely divided organic solid material or finely divided inorganic solid material. In one example, the carrier contains a dust, a granule, a powder or a salt crystal. For example, the carrier contains alumina, amorphous silica, attapulgite, calcium carbonate, calcium phosphate, clay, chalk, fumed silica, diatomaceous earth, a kaolin, magnesium carbonate, microparticulate cellulose, montmorillonite, pyrophyllite, silicic acid, sodium bicarbonate, sodium carbonate, sodium phosphate, sodium pyrophosphate, talc, vermiculite, or combinations thereof.

In another example, the carrier contains an aerosol propellant that is selected from among argon, butane, carbon dioxide, a chlorofluorocarbon, dimethyl ether, a hydrocarbon, a hydrofluorocarbon, isobutane, nitrogen, propane, and mixtures thereof. In some examples, the aerosol propellant contains difluoromethane, trifluoromethane, difluoroethane, trifluoroethane, tetrafluoroethane or octafluorocyclobutane or combinations thereof. In yet another example, the carrier contains a silicone oil that is selected from among cyclical silicones, linear or branched open chained silicones, and combinations thereof. For example, the silicone oil is selected from among volatile silicones selected from among cyclic polydimethylsiloxanes containing an average of from about 3 to about 9 silicon atoms and linear polydimethylsiloxanes containing an average of from about 3 to about 9 silicon atoms and non-volatile silicones selected from among dimethicone copolyol, cyclomethicone, polydimethylsiloxane, cyclic dimethyl polysiloxane, aminosilicones, phenylsilicones, diphenyldimethicones, phenyltrimethicones, cyclopentasiloxane, a polymer of dimethyl-siloxane with polyoxyethylene and/or polyoxypropylene, dimethicone copolyol, cetyldimethicone copolyol, cetyl dimethicone and dimethiconol and combinations thereof. In another example, the carrier contains a silicone oil selected from among polydimethylsiloxane, phenylated silicones, decamethylcyclopentasiloxane, dodecamethylcyclohexasiloxane and octamethyl-cyclotetrasiloxane, and combinations thereof.

In another example, the carrier contains a monoglyceride, a diglyceride, an acetylated monoglyceride, or a triglyceride or combinations thereof. In yet another example, the carrier contains 1-propanol, 2-propanol, 1-butanol, 2-butanol, 2-methyl-1-propanol, 1-pentanol, 2-pentanol, 3-methyl-1-butanol, 3-methyl-2-butanol, ethylene glycol, propylene glycol, 1,4-butanediol, 1,3-butanediol, 2-methyl-1,3-propanediol, 1,4-cyclohexanedimethanol, diethylene glycol, triethylene glycol, PEG-200, PEG-300, PEG-400, PEG-600, 2-methoxyethanol, 2-ethoxyethanol, 2-propoxyethanol, 2-isopropoxyethanol, 2-butoxyethanol, 1-methoxy-2-propanol, 1-ethoxy-2-propanol, 3-methoxy-1-butanol, diethylene glycol monomethyl ether, diethylene glycol monoethyl ether, diethylene glycol mono-n-propyl ether, diethylene glycol mono-isopropyl ether, diethylene glycol monobutyl ether, triethylene glycol monomethyl ether, glycerol, 3-methoxy-1,2-propanediol, or 3-ethoxy-1,2-propanediol. In one example, the carrier contains borneol, citronellol, geraniol, D-limonene, dipentene or a combination thereof. In another example, the carrier contains a cyclodextrin that is an α-cyclodextrin, β-cyclodextrin or γ-cyclodextrin or combinations thereof.

In some examples of the provided methods for killing or repelling insects, the composition containing the solavetivone, 5-epi-β-vetivone or a derivative or analog thereof of either or mixtures thereof further contains a dispersing agent selected from among a surfactant, polyvinylpyrrolidone, polyoxyethylated castor oil, polyoxyethylene sorbitan ester, alkylnaphthalene sulfonate, alkylbenzenesulfonate, polyoxyethylene, polycarboxylate, lignin sulfonate, sodium silicate, potassium silicate, methylcellulose, carboxymethyl cellulose, hydroxypropylcellulose, hydroxypropyl-methylcellulose, gum arabic, a polyacrylate, and an acrylic/maleic copolymers and combinations thereof. In some examples, the dispersing agent is a surfactant selected from among an anionic surfactant, a cationic, a non-ionic surfactant, and a zwitterionic surfactant and combinations thereof. In some examples, the surfactant is an anionic surfactant selected from among fatty soaps, alkyl sulfates, sulfated oils, ether sulfates, sulfonates, sulfosuccinates, sulfonated amides and isethionates. In other examples, the surfactant is an anionic surfactant selected from among alkyl sulfonate surfactants, a linear alkylbenzene sulfonic acid, a branched alkylbenzene sulfonic acid a $C_{12}$ to $C_{18}$ alkylsulfate, $C_{12}$-$C_{18}$ alkyl alkoxy sulfate, $C_{12}$-$C_{18}$ alkyl methyl ester sulfonate and combinations thereof. In some examples, the surfactant is a cationic surfactant selected from among an alkylamine, an alkyl diamine, an alkyl polyamine, a mono- or di-quaternary ammonium salt, a monoalkoxylated amine, a dialkoxylated amine, a monoalkoxylated quaternary ammonium salt, a dialkoxylated quaternary ammonium salt, an etheramine, an amine oxide, an alkoxylated amine oxide and a fatty imidazoline and combinations thereof. In some examples, the surfactant is a non-ionic surfactant selected from among an alkoxylated alcohol, a dialkoxylated alcohol, an alkoxylated dialkylphenol, an alkylpolyglycoside, an alkoxylated alkylphenol, an alkoxylated glycol, an alkoxylated mercaptan, an alkylamine, salt, an alkyl quaternary amine salt, a glyceryl or polyglyceryl ester of a natural fatty acid, an alkoxylated glycol ester, an alkoxylated fatty acid, an alkoxylated alkanolamide, a polyalkoxylated silicone and an N-alkyl pyrrolidone and combinations thereof. The dispersing agent can be present in an amount of between at or about 0.002% and at or about 50%, or between at or about 0.025% and at or about 25%, or between at or about 0.01% and at or about 15%, by weight, of the composition.

In some examples of the provided methods for killing or repelling insects, the composition containing the solavetivone, 5-epi-β-vetivone or a derivative or analog thereof of either or mixtures thereof further contains a viscosity modulating agent selected from among an acrylate, an acrylate copolymer, an alginate, an arabinogalactan, a carrageenan, a cellulosic polymer, a ceramide, chitan, dextran, diutan, fucelleran, fucoidan, a β-glucan, a gellan gum, guar gum, gum arabic, gum ghatti, gum tragacanth, karaya gum, laminaran, locust bean gum, a methacrylate, a methyl methacrylate, modified starch, pectin, propylene glycol alginate, psyllium gum, polyvinyl pyrrolidone, rhamsan gum, scleroglucan, starch, starch hydroxyethyl ether, starch dextrins and xanthan gum, and combinations thereof. In some examples, the viscosity modulating agent is a xanthan gum that is a low acetate xanthan gum or a high pyruvate xanthan gum. In some examples, the viscosity modulating agent is a cellulosic polymer that is selected from among bacterial cellulose, carboxymethyl cellulose, ethyl cellulose, ethylhydroxyethylcellulose, hydroxyethyl cellulose, hydroxypropyl cellulose, hydroxypropyl methylcellulose, methyl cellulose, microparticulate cellulose and sodium carboxymethyl cellulose and combinations thereof. The viscosity modulating agent can be present in an amount of between at or about 0.05% and at or about 25%, or between at or about 0.1% and at or about 10%, or between at or about 0.5% and at or about 5%, by weight, of the composition.

In some examples of the provided methods for killing or repelling insects, the composition containing the solavetivone, 5-epi-β-vetivone or a derivative or analog thereof of either or mixtures thereof further contains a gelling agent that is selected from among agar, a carbomer, carboxyvinyl polymers, dibenzylidene alditols, collagen, dextrin fatty acid esters, gelatin, hydrogenated styrene/isoprene copolymers, 12-hydroxystearic acid, κ-carrageenan, gellan gum, pectin, polyacrylic acids, styrene-ethylene/propylene block copolymers, styrene-ethylene/butylene-styrene block copolymers, sucrose fatty acid esters and a wax and combinations thereof. In some examples, the gelling agent is a wax that is selected from among candelilla wax, carnauba wax, ceresin wax, microcrystalline wax paraffin wax and polyethylene wax. The gelling agent can be present in an amount between at or about 0.01% and at or about 10%, between at or about 0.05% and at or about 7.5%, between at or about 0.1% and at or about 5%, or between at or about 0.25% and at or about 2.5%, by weight, of the composition.

In some examples of the provided methods for killing or repelling insects, the composition containing the solavetivone, 5-epi-β-vetivone or a derivative or analog thereof of either or mixtures thereof further contains an antioxidant that is selected from among ascorbyl palmitate, butylatedp-cresol, tert-butylhydroquinone, butylated hydroquinone monomethyl ether, butylhydroxyanisole, butylhydroxytoluene, propyl gallate and a tocopherol, and combinations thereof. The antioxidant can be present in an amount between at or about 0.001% and at or about 5%, between at or about 0.005% and at or about 2.5%, or between at or about 0.01% to at or about 1%, by weight, of the composition.

In some examples of the provided methods for killing or repelling insects, the composition containing the solavetivone, 5-epi-β-vetivone or a derivative or analog thereof of either or mixtures thereof further contains a preservative that is selected from among azoles, benzisothiazolin-3-one, benzalkonium quaternary compounds, benzyl alcohol, borates, 2-bromo-2-nitro-propane-1,3-diol, butylparaben, 5-chloro-2-methyl-4-isothiazolin-3-one, chlorphenesin, chloroxylenol, diazolidinyl urea, a dimethyl-benzylalkyl-ammonium chloride, ethylparaben, formaldehyde, glutaraldehyde, halogenated salicylanilides, hexachlorophene, isobutylparaben, isothiazolin-3-one, 2-methyl-4-isothiazoline-3-one, methylparaben, monochloracetamide, neomycin sulfate, o-phenylphenol and salts thereof, phenoxyethanol, propionic acid and salts thereof, propylparaben, sodium benzoate, sorbic acid and salts thereof, tebuconazole and triazoles, and combinations thereof. The preservative can be present in an amount between at or about 0.001% and at or about 5%, or between at or about 0.005% and at or about 2.5%, or between at or about 0.01% to at or about 1%, by weight, of the composition.

In some examples of the provided methods for killing or repelling insects, the composition containing the solavetivone, 5-epi-β-vetivone or a derivative or analog thereof of either or mixtures thereof further contains a colorant that is a dye or pigment. The colorant can be present in an amount between at or about 0.0001% to at or about 1%, or between at or about 0.0005% and at or about 0.5%, by weight, of the composition.

In some examples of the provided methods for killing or repelling insects, the composition containing the solavetivone, 5-epi-β-vetivone or a derivative or analog thereof of either or mixtures thereof further contains a synergist that is selected from among bis-(2,3,3,3-tetrachloropropyl)ether, dodecyl imidazole, N-(2-ethylhexyl)-bicyclo-[2,2,1]hept-5-ene-2,3-dicarboxyimide piperonyl butoxide, isobornyl thiocyanatoacetate, safroxan and sesame, and combinations thereof. The synergist can be present in an amount from at or about 1% to at or about 50%, by weight, of the composition.

In some examples of the provided methods for killing or repelling insects, the composition containing the solavetivone, 5-epi-β-vetivone or a derivative or analog thereof of either or mixtures thereof further contains a penetration agent that is selected from among silicone dioxide, petroleum distillate, light solvent naphtha and D-limonene, and combinations thereof. The penetration agent can be present in an amount of at or about 0.001% to at or about 50%, by weight, of the composition.

In some examples of the provided methods for killing or repelling insects, the composition containing the solavetivone, 5-epi-β-vetivone or a derivative or analog thereof of either or mixtures thereof is formulated as a personal care or cosmetic composition that is selected from among insect repellents, skin care products, hair care products and cleansing products. In one example, the composition is formulated as a skin care product that is selected from among skin conditioners, hand lotions, body lotions, facial lotions, skin moisturizers, skin toners, skin sanitizers, skin cleansing compositions, skin soothing and lubricating compositions, sunscreen products, anti-aging products, tanning products, self-tanning products, after-sun products, masking products and anti-wrinkle products. In another example, the composition is formulated as a hair care product that is selected from among hair conditioners, hair styling gels, hair antidandruff compositions, hair lotions, hair tonics, rinses, conditioners, hair anti-frizzing agent compositions, hair shining compositions, mousses, styling gels, hair pomade products and hair sprays. In another example, the composition is formulated as a cleansing product that is selected from among soaps, foaming bath products, hand/body/facial cleansers, astringent cleansers, anti-acne products, body shampoos, synthetic detergent bars, shower gels and shampoos.

In some examples of the provided methods for killing or repelling insects, the composition containing the solavetivone, 5-epi-β-vetivone or a derivative or analog thereof of either or mixtures thereof is formulated as a household care product that is selected from among air deodorant/freshener compositions in liquid, gel or solid form, all purpose cleaner compositions, all purpose disinfectant compositions, deodorizing sprays and powders, dish detergents, fabric sizing compositions, fabric softening compositions, fabric static control compositions, hard surface cleanser compositions, hard surface detergents, hard surface sanitizing compositions, linen and bedding spray compositions, pesticide compositions, polishing compositions, laundry detergents, rug and upholstery shampoo compositions, cleaners and deodorizers, tile, toilet and tub cleaning and disinfectant compositions, waxes and cleaning compositions for treating wood floors or furniture, and waxes and cleaning compositions for automobiles. In another example, the composition is formulated as a fabric softening composition selected from among a liquid fabric softener, a fabric softening rinse, a fabric softening sheet and a fabric softening gel.

In some examples of the provided methods for killing or repelling insects, the composition containing the solavetivone, 5-epi-β-vetivone or a derivative or analog thereof of either or mixtures thereof is formulated as an aerosol, bar, cream, gel, liquid, lotion, paste, powder, roll-on, sheet, spray, stick or tablet.

In some examples of the provided methods for killing or repelling insects, the composition containing the solavetivone, 5-epi-β-vetivone or a derivative or analog thereof of either or mixtures thereof further contains at least or about at least 0.2% to at least or about at least 5% gelling agent selected from among agar, an alginate, a carbomer, carboxyvinyl polymers, dibenzylidene alditols, carboxypolymethylene, collagen, dextrin fatty acid esters, gelatin, hydrogenated styrene/isoprene copolymers, 12-hydroxystearic acid, κ-carrageenan, gellan gum, a lower hydroxy cellulose, pectin, polyacrylic acids, styrene-ethylene/propylene block copolymers, styrene-ethylene/butylene-styrene block copolymers, sucrose fatty acid esters and a wax and combinations thereof.

In some examples of the provided methods for killing or repelling insects, the composition containing the solavetivone, 5-epi-β-vetivone or a derivative or analog thereof of either or mixtures thereof further contains an additional compound that repels and/or kills pests or insects selected from among N,N-diethyl-meta-toluamide, picaridin (2-(2-hydroxyethyl)-1-piperidinecarboxylic acid 1-methylpropyl ester), citronella oil, camphor oil, cedarwood oil, coumarin, 2-hydroxy-methylcyclohexyl acetic acid lactone, beta-alanine, 2-hydroxymethyl-cyclohexylidene acetic acid lactone, 2-hydroxy-methylcyclohexyl propionic acid lactone, p-menthane-3,8-diol, and 3-[N-butyl-N-acetyl]-aminopropionic acid ethyl ester and combinations thereof. In some examples, the additional compound that repels and/or kills pests or insects is present in an amount of at least or about at least 0.1% to at least or about at least 25%, by weight, of the composition.

In some examples of the provided methods for killing or repelling insects, the location is a human or animal infested with an pest or insect. For example, the location is a human or animal infested with an pest or insect, and deploying the composition prevents skin injury due to biting pests or insects. In some examples, the biting pest or insect is selected from among ants, bedbugs, chiggers, fleas, lice, mites, mosquitoes, scabies, and ticks. In some examples, the location is a structure infested with termites, such as a wood structure, wooden object, air supply duct, an attic, an awning, a basement, a cellar, a crawlspace, a deck, a dock, a garage, a hamper, a heating vent, a home foundation, a linen storage closet, a pool deck, roof tiles, a shipping container, a storage unit, a suitcase, a walkway and a wall space. In a particular example, the location is a wooden structure supported by a foundation, and the method includes the steps of removing the soil from around at least a portion of the structure to expose at least a portion of the foundation; providing a composition containing solavetivone, 5-epi-β-vetivone or a derivative or analog thereof; deploying the composition to the exposed foundation; and replacing the soil to cover the exposed foundation, wherein the insect or pest is repelled from the location or dies after coming in contact with the composition or vapors from the composition.

Provided herein are pest or insect repellent compositions containing a composition containing solavetivone, 5-epi-β-vetivone or a derivative or analog of either, or mixtures of any of the foregoing in a concentration sufficient to repel a pest or insect; and a delivery vehicle, whereby the pest or insect repellent is contacted with a selected location. In some examples, the delivery vehicle contains an aqueous formulation, an aerosol, a cream, a gel, a lotion, an oil, a spray, a soap, a detergent, a particulate or a substrate. In some examples, the insect repellent composition contains at least or at least about 0.1% solavetivone, 5-epi-β-vetivone or a derivative or analog thereof. For example, the solavetivone, 5-epi-β-vetivone or a derivative or analog thereof is present in an amount between at least or at least about 0.1% and at or about 99%, or between at least or at least about 0.1% and at or about 95%, or between at or about 0.1% and at or about 50%, or between at or about 0.1% and at or about 25%, or between at or about 0.1% and at or about 20%, or between at or about 0.1% and at or about 10%, by weight, of the composition.

In some examples of the pest or insect repellent compositions, the delivery vehicle is a substrate that is a paper, a cloth, a woven or nonwoven material, an infused plastic or an absorbent plastic polymer. For example, the delivery vehicle is a nonwoven material is a flexible sheet containing fibers that are adhesively or thermally bonded. In some examples, the fibers are selected from among cellulose ester, cotton, hemp, jute, linen, ramie, rayon, polyamides, polyesters polyolefins, polypropylene, polyvinyl derivatives, silk, sisal and wool and combinations thereof. In other examples, the delivery vehicle is a substrate that is an absorbent plastic polymer capable of absorbing the composition containing solavetivone, 5-epi-β-vetivone or a derivative or analog thereof. In some examples, the absorbent plastic polymer is a pet collar.

In some examples of the pest or insect repellent compositions, the delivery vehicle is formulated as a gel that contains at least or about at least 0.2% to at least or about at least 5%, by weight, of a gelling agent that is selected from among agar, a carbomer, carboxyvinyl polymers, dibenzylidene alditols, carboxypolymethylene, collagen, dextrin fatty acid esters, gelatin, hydrogenated styrene/isoprene copolymers, 12-hydroxystearic acid, κ-carrageenan, gellan gum, a lower hydroxy cellulose, pectin, polyacrylic acids, styrene-ethylene/propylene block copolymers, styrene-ethylene/butylene-styrene block copolymers, sucrose fatty acid esters and a wax and combinations thereof.

In some examples of the pest or insect repellent compositions, the compositions further contain water, an alcohol, a ketone, an ester, an ether or an oil that is present in a concentration between at or about 1% and at or about 99.7%, or between at or about 10% and at or about 80%, or between at or about 20% and at or about 70%, or between at or about 30% and at or about 60%, or between at or about 10% and at or about 40%, or between at or about 30% and at or about 70%, or between at or about 60% and at or about 90%, by weight, of the composition. In one example, the composition further contains an alcohol that is selected from among an aromatic alcohol, a $C_1$-$C_6$ monohydric alcohol, $C_2$-$C_6$ polyhydric alcohol, a polyvalent alcohol, and mixtures thereof. In another example, the composition further contains an oil that is selected from among almond oil, avocado oil, canola oil, cashew oil, cherry seed oil, cocoa butter, coconut oil, corn oil, cottonseed oil, flaxseed oil, grape seed oil, jojoba oil, macadamia nut oil, olive oil, palm oil, palm fruit oil, peanut oil, rapeseed oil, rice bran oil, safflower oil, sesame oil, soybean oil, sunflower oil, and walnut oil and combinations thereof. In another example, the composition further contains a ketone that is selected from among acetone, methyl ketone, methyl benzyl ketone, methyl ethyl ketone, methyl isopropyl ketone, methyl butyl ketone, ethyl ketone, benzyl methyl ketone, and combinations thereof.

In some examples of the pest or insect repellent compositions, the delivery vehicle is in the form of a fluid that when dispensed forms a gel in situ. In other examples, the delivery vehicle is a particulate selected from among an alumina, amorphous silica, attapulgite, calcium carbonate, calcium phosphate, a clay, chalk, diatomaceous earths, fumed silica, a kaolin, kieselguhr, magnesium carbonate, microparticulate cellulose, montmorillonite, pyrophyllite, silicic acid, sodium bicarbonate, sodium carbonate, sodium phosphate, sodium pyrophosphate, talc, and vermiculite, and combinations thereof. In further examples, the delivery vehicle is an aerosol that contains an aerosol propellant that is selected from among argon, butane, carbon dioxide, a chlorofluorocarbon, dimethyl ether, a hydrocarbon, a hydrofluorocarbon, isobutane, nitrogen, propane, and mixtures thereof. In some examples, the aerosol propellant contains difluoromethane, trifluoromethane, difluoroethane, trifluoroethane, tetrafluoroethane or octafluorocyclobutane or combinations thereof.

Provided herein are pesticide or insecticide compositions containing a composition containing solavetivone, 5-epi-β-vetivone, a derivative or analog thereof and mixtures thereof in a concentration sufficient to kill the insect or pest when adhered thereto; and a carrier that adheres to the insect or pest or penetrates the exoskeleton of the insect or pest. In some examples, the pesticide or insecticide composition contains at least or at least about 1% solavetivone, 5-epi-β-vetivone or a derivative or analog thereof. For example, the solavetivone, 5-epi-β-vetivone or a derivative or analog thereof is present in a concentration between at least or at least about 1% and at or about 99%, or between at or about 1% and at or about 50%, or between at or about 1% and at or about 25%, or between at or about 1% and at or about 20%, or between at or about 1% and at or about 10%, by weight, of the composition. In some examples, the carrier contains a particulate selected from among an alumina, amorphous silica, attapulgite, calcium carbonate, calcium phosphate, a clay, chalk, diatomaceous earths, fumed silica, a kaolin, kieselguhr, magnesium carbonate, microparticulate cellulose, montmorillonite, pyrophyllite, silicic acid, sodium bicarbonate, sodium carbonate, sodium phosphate, sodium pyrophosphate, talc, and vermiculite, and combinations thereof. In other examples, the carrier forms a viscous fluid or gel when dispensed.

In some examples of the pesticide or insecticide compositions, the carrier contains at least or about at least 0.2% to at least or about at least 5% gelling agent selected from among agar, an alginate, a carbomer, carboxyvinyl polymers, dibenzylidene alditols, carboxypolymethylene, collagen, dextrin fatty acid esters, gelatin, hydrogenated styrene/isoprene copolymers, 12-hydroxystearic acid, κ-carrageenan, gellan gum, a lower hydroxy cellulose, pectin, polyacrylic acids, styrene-ethylene/propylene block copolymers, styrene-ethylene/butylene-styrene block copolymers, sucrose fatty acid esters and a wax and combinations thereof. In other examples, the carrier contains at least or at least about 0.2% to at least or at least about 20%, by weight, of a viscosity modulating agent selected from among an acrylate, an acrylate copolymer, an alginate, an arabinogalactan, a carrageenan, a cellulosic polymer, a ceramide, chitan, dextran, diutan, fucelleran, fucoidan, a β-glucan, a gellan gum, guar gum, gum arabic, gum ghatti, gum tragacanth, karaya gum, laminaran, locust bean gum, a methacrylate, a methyl methacrylate, modified starch, pectin, propylene glycol alginate, psyllium gum, polyvinyl pyrrolidone, rhamsan gum, scleroglucan, starch, starch hydroxyethyl ether, starch dextrins and a xanthan gum and combinations thereof. In some examples, the pesticide or insecticide composition further contains a penetration agent containing silicone dioxide, petroleum distillate, light solvent naphtha or D-limonene or combinations thereof.

In any of the provided pest or insect repellent compositions or pesticide or insecticide compositions, the derivative or analog of solavetivone can be selected from among 3-hydroxysolavetivone, 3,9-dihydroxysolavetivone, 3-hydroxy-9-(3-methyl-2-butenoyloxy)solavetivone, 3-acetoxysolavetivone, 13-hydroxysolavetivone, 3-acetoxy-9-(2-methylpropionyloxy)solavetivone, 3-hydroxy-9-(3-methylbutanoyloxy)solavetivone, 3-acetoxy-9-(3-methylbutanoyloxy)solavetivone, 3-acetoxy-9-(3-methyl-2-butenoyloxy)solavetivone, 3-hydroxy-9-tigloyloxysolavetivone, 3-hydroxy-9- isobutanoyloxysolavetivone, 3-beta-acetoxysolavetivone and 3-beta-hydroxysolavetivone.

In some examples, the provided pest or insect repellent compositions or pesticide or insecticide compositions further contain a dispersing agent that is selected from among a surfactant, polyvinylpyrrolidone, polyoxyethylated castor oil, a polyoxyethylene sorbitan ester, alkylnaphthalene sulfonate, alkylbenzenesulfonate, polyoxyethylene, polycarboxylate, lignin sulfonate, sodium silicate, potassium silicate, methylcellulose, carboxymethyl cellulose, hydroxypropylcellulose, hydroxypropyl-methylcellulose, gum arabic, a polyacrylate, and an acrylic/maleic copolymers and combinations thereof. In some examples, the surfactant is selected from among an anionic surfactant, a cationic, a non-ionic surfactant, and a zwitterionic surfactant and combinations thereof. For example, the surfactant is an anionic surfactant selected from among fatty soaps, alkyl sulfates, sulfated oils, ether sulfates, sulfonates, sulfosuccinates, sulfonated amides and isethionates. In another example, the surfactant is an anionic surfactant selected from among alkyl sulfonate surfactants, a linear alkylbenzene sulfonic acid, a branched alkylbenzene sulfonic acid a $C_{12}$ to $C_{18}$ alkylsulfate, $C_{12}$-$C_{18}$ alkyl alkoxy sulfate, $C_{12}$-$C_{18}$ alkyl methyl ester sulfonate and combinations thereof. In another example, the surfactant is a cationic surfactant selected from among an alkylamine, an alkyl diamine, an alkyl polyamine, a mono- or di-quaternary ammonium salt, a monoalkoxylated amine, a dialkoxylated amine, a monoalkoxylated quaternary ammonium salt, a dialkoxylated quaternary ammonium salt, an etheramine, an amine oxide, an alkoxylated amine oxide and a fatty imidazoline and combinations thereof. In yet another example, the surfactant is a non-ionic surfactant is selected from among an alkoxylated alcohol, a dialkoxylated alcohol, an alkoxylated dialkylphenol, an alkylpolyglycoside, an alkoxylated alkylphenol, an alkoxylated glycol, an alkoxylated mercaptan, an alkylamine salt, an alkyl quaternary amine salt, a glyceryl or polyglyceryl ester of a natural fatty acid, an alkoxylated glycol ester, an alkoxylated fatty acid, an alkoxylated alkanolamide, a polyalkoxylated silicone and an N-alkyl pyrrolidone and combinations thereof. The dispersing agent can be present in a concentration of between at or about 0.002% and at or about 50%, or between at or about 0.025% and at or about 25%, or between at or about 0.01% and at or about 15%, by weight, of the composition.

In some examples, the provided pest or insect repellent compositions or pesticide or insecticide compositions further contain a viscosity modulating agent that is selected from among an acrylate, an acrylate copolymer, an alginate, an arabinogalactan, a carrageenan, a cellulosic polymer, a ceramide, chitan, dextran, diutan, fucelleran, fucoidan, a β-glucan, a gellan gum, guar gum, gum arabic, gum ghatti, gum tragacanth, karaya gum, laminaran, locust bean gum, a methacrylate, a methyl methacrylate, modified starch, pectin, propylene glycol alginate, psyllium gum, polyvinyl pyrrolidone, rhamsan gum, scleroglucan, starch, starch hydroxyethyl ether, starch dextrins and xanthan gum, and combinations thereof. In some examples, the viscosity modulating agent is a xanthan gum that is a low acetate xanthan gum or a high pyruvate xanthan gum. In other examples, the viscosity modulating agent is a cellulosic polymer that is selected from among bacterial cellulose, carboxymethyl cellulose, ethyl cellulose, ethyl-hydroxyethylcellulose, hydroxyethyl cellulose, hydroxypropyl cellulose, hydroxypropyl methylcellulose, methyl cellulose, microparticulate cellulose and sodium carboxymethyl cellulose and combinations thereof. The viscosity modulating agent can be present in a concentration of between at or about 0.05% and at or about 25%, or between at or about 0.1% and at or about 10%, or between at or about 0.5% and at or about 5%, by weight, of the composition.

In some examples, the provided pest or insect repellent compositions or pesticide or insecticide compositions further contain an antioxidant that is selected from among ascorbyl palmitate, butylated p-cresol, tert-butylhydroquinone, butylated hydroquinone monomethyl ether, butylhydroxyanisole, butylhydroxytoluene, propyl gallate and a tocopherol, and combinations thereof. The antioxidant can be present in a concentration between at or about 0.001% and at or about 5%, between at or about 0.005% and at or about 2.5%, or between at or about 0.01% to at or about 1%, by weight, of the composition.

In some examples, the provided pest or insect repellent compositions or pesticide or insecticide compositions further contain a preservative that is selected from among azoles, benzisothiazolin-3-one, benzalkonium quaternary compounds, benzyl alcohol, borates, 2-bromo-2-nitro-propane-1,3-diol, butylparaben, 5-chloro-2-methyl-4-isothiazolin-3-one, chlorphenesin, chloroxylenol, diazolidinyl urea, a dimethyl-benzylalkyl-ammonium chloride, ethylparaben, formaldehyde, glutaraldehyde, halogenated salicylanilides, hexachlorophene, isobutylparaben, isothiazolin-3-one, 2-methyl-4-isothiazoline-3-one, methylparaben, monochloracetamide, neomycin sulfate, o-phenylphenol and salts thereof, phenoxyethanol, propionic acid and salts thereof, propylparaben, sodium benzoate, sorbic acid and salts thereof, tebuconazole and triazoles, and combinations thereof. The preservative can be present in a concentration between at or about 0.001% and at or about 5%, or between at or about 0.005% and at or about 2.5%, or between at or about 0.01% to at or about 1%, by weight, of the composition.

In some examples, the provided pest or insect repellent compositions or pesticide or insecticide compositions further contain a colorant that is a dye or pigment. The colorant can be present in a concentration of at or about 0.0001% to at or about 1%, or from at or about 0.0005% to at or about 0.5%, by weight, of the composition.

In some examples, the provided pest or insect repellent compositions or pesticide or insecticide compositions further contain a synergist that is selected from among bis-(2,3,3,3-tetrachloropropyl)ether, dodecyl imidazole, N-(2-ethylhexyl)-bicyclo-[2,2,1]hept-5-ene-2,3-dicarboxyimide piperonyl butoxide, isobornyl thiocyanatoacetate, safroxan and sesame, and combinations thereof. The synergist can be present in an amount of at or about 1% to at or about 50%, by weight, of the composition.

In some examples, the provided pest or insect repellent compositions further contain a penetration agent that is selected from among silicone dioxide, petroleum distillate, light solvent naphtha and D-limonene, and combinations thereof. The penetration agent can be present in an amount of at or about 0.001% to at or about 50%, by weight, of the composition.

In some examples, the provided pest or insect repellent compositions or pesticide or insecticide compositions further contain an additional compound that repels and/or kills insects or pests selected from among N,N-diethyl-meta-toluamide (DEET), picaridin (2-(2-hydroxyethyl)-1-piperidinecarboxylic acid 1-methylpropyl ester), citronella oil, camphor oil, cedarwood oil, coumarin, 2-hydroxy-methylcyclohexyl acetic acid lactone, beta-alanine, 2-hydroxymethyl-cyclohexylidene acetic acid lactone, 2-hydroxy-methylcyclohexyl propionic acid lactone, p-menthane-3,8-diol, and 3-[N-butyl-N-acetyl]-aminopropionic acid ethyl ester and combinations thereof. The additional compound that repels and/or kills pests or insects can be present in an amount of at least or about at least 0.1% and at least or about at least 25%, by weight, of the composition.

In some examples, the provided pest or insect repellent compositions or pesticide or insecticide compositions kill a pest or insect selected from among Siphonaptera insects, such as cat flea (*Ctenocephalides felis*), dog flea (*Ctenocephalides canis*), oriental rat flea (*Xenopsylla cheopis*), human flea (*Pulex irritans*), chigoe (*Tunga penetrans*) and European rat flea (*Nosopsyllus fasciatus*); Anoplura insects, such as Head louse (*Pediculus humanus capitis*), crab louse (*Pthirus pubis*), short-nosed cattle louse (*Haematopinus eurysternus*), sheep louse (*Dalmalinia ovis*), hog louse (*Haematopinus suis*), long-nosed cattle louse (*Linognathus vituli*), cattle biting louse (*Bovicola bovis*), poultry shaft louse (*Menopon gallinae*), poultry body louse (*Menacanthus stramineus*), little blue cattle louse (*Solenopotes capillatus*), *Haematopinus* spp., *Linognathus* spp., *Pediculus* spp., *Phtirus* spp. and *Solenopotes* spp.; Acarina insects, such as bush tick (*Haemaphysalis longicornis*), *Haemaphysalis flava, Dermacentor taiwanicus*, American dog tick (*Dermacentor variabilis*), *Ixodes ovatus, Ixodes persulcatus*, black legged tick (*Ixodes scapularis*), lone star tick (*Amblyomma americanum*), *Boophilus microplus, Rhipicephalus sanguineus, Ixodes holocyclus*, western black legged tick (*Ixodes pacificus*), *Dermacentor andersoni, Amblyomma maculatum*, ear mite (*Octodectes cynotis*), *Psoroptes* spp., *Chorioptes* spp., *Otodectes* spp., *Sarcoptes* spp., *Notoedres* spp., *Knemidocoptes* spp., *Sacroptes scabiei, Demodex* spp., follicle mite (*Demodex canis*), northern fowl mite (*Ornithonyssus sylviarum*), poultry red mite (*Dermanyssus gallinae*), *Trombicula* spp., *Leptotrombidium akamushi, Ornithodorus hermsi, Ornithodorus turicata, Ornithonyssus bacoti, Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Cytodites* spp. and *Laminosioptes* spp.; Heteroptera insects, such as common bedbug (*Cimex lectularius*), tropical bedbug (*Cimex hemipterus*), *Reduvius senilis, Triatoma* spp. *Rhodnius* spp., *Panstrongylus* spp., and *Arilus critatus*; and Mallophage (Amblycera and Ischnocera) insects, such as *Trimenopon* spp., *Menopon* spp., *Trinoton* spp., *Bovicola* spp., *Werneckiella* spp., *Lepikentron* spp., *Trichodectes* spp. and *Felicola* spp. In some examples, the pest or insect is selected from among ants, bedbugs, carpet beetles, centipedes, chiggers, drain flies, dust mites, earwigs, fleas, flies, gnats, hornets, lice, millipedes, mites, mosquitoes, scabies, silverfish, spiders, stinkbugs, termites, ticks, wasps, weevils and yellow jackets.

Any of the provided pest or insect repellent compositions or pesticide or insecticide compositions can be formulated for delivery of solavetivone, 5-epi-β-vetivone or a derivative or analog thereof for a period of time selected from among at least 1 hour, 2 hours, 3 hours, 4 hours, 5 hours, 6, hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, at least 1 day, 2 days, 3 days, 4 days, 5 days, 6 days 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, at least 45 days, at least 60 days, at least 75 days, at least 90 days, at least 4 months, at least 5 months, at least 6 months, at least 7 months, at least 8 months, at least 9 months, at least 10 months, at least 11 months and at least 1 year.

Provided herein are aerosol propellant pressurized sprayable pest repellent or pesticide products containing a composition containing a sufficient concentration of solavetivone, 5-epi-β-vetivone, or a derivative or analog of either, or mixtures of any of the foregoing, wherein the concentration is sufficient to repel or kill a pest or insect; and at least at or about at least 5% to at least or about at least 75% propellant, by weight, of the composition. In some examples, the propellant contains carbon dioxide, propane, butane or a mixture thereof. In some examples, the solavetivone, 5-epi-β-vetivone or a derivative or analog thereof is present in a concentration of at least or at least about 0.5%, by weight, of the composition. For example, the solavetivone, 5-epi-β-vetivone or a derivative or analog thereof is present in a concentration from at least or at least about 0.5% to at least or at least 95%, by weight, of the composition.

Provided herein are cleansing compositions containing a composition containing a sufficient concentration of solavetivone, 5-epi-β-vetivone, a derivative or analog thereof or mixtures thereof, wherein the concentration is sufficient to repel or kill a pest or insect; and from at or about 1% to at about 80%, by weight, of the composition of a detergent component or softening active agent. In some examples, the detergent component is selected from among anionic surfactants, nonionic surfactants, zwitterionic surfactants, ampholytic surfactants and cationic surfactants and mixtures thereof. In some examples, the softening active agent is selected from among cationic surfactants, monomethyl trialkyl quaternaries, imidazolinium quaternaries, dimethyl alkyl benzyl quaternaries, dialkyl dimethyl quaternaries, methyl dialkoxy alkyl quaternaries, diamido amine-based quaternaries and dialkyl methyl benzyl quaternaries or ($C_8$-$C_{24}$) fatty acid amides and combinations thereof. In some examples, the solavetivone, 5-epi-β-vetivone or a derivative or analog thereof is present in a concentration of at least or at least about 0.5%, by weight, of the composition. For example, the solavetivone, 5-epi-β-vetivone or a derivative or analog thereof is present in a concentration from at least or at least about 0.5% to at least or at least about 99%, by weight, of the composition. The provided cleansing compositions can further contain a detergency builder component in a concentration of at or about 1% to at or about 80%, by weight, of the composition. The detergency builder component can be selected from among alkali metal carbonates, alkali metal phosphates, alkali metal phosphonates, alkali metal polyphosphates, alkali metal polyphosphonic acids, alkali metal silicates, $C_8$-$C_{18}$ alkyl monocarboxylic acids, alkali metal, ammonium or substituted ammonium salts of polycarboxylic acids and a zeolite and mixtures thereof. In some examples, the cleansing compositions are formulated as liquids, solids or powders. For example, the cleansing compositions are formulated as heavy-duty detergent powder, heavy-duty detergent liquid, dishwashing liquid, machine dishwashing detergents, institutional detergents, detergent liquids, laundry aid, pretreatment aid, after-treatment aids, presoaking product, hard surface cleaner, or carpet cleaner.

Provided herein are fabric treatment sheet products containing a woven or nonwoven sheet that is coated or impregnated with a fabric treatment composition; and a composition containing a sufficient concentration of solavetivone, 5-epi-β-vetivone, a derivative or analog thereof or mixtures thereof, wherein the concentration is sufficient to repel or kill a pest or insect. In some examples, the solavetivone, 5-epi-β-vetivone or a derivative or analog thereof is present in a concentration of at least or at least about 0.5%, by weight, of the composition. For example, the solavetivone, 5-epi-β-vetivone or a derivative or analog thereof is present in a concentration from at least or at least about 0.5% to at least or at least about 99%, by weight, of the composition. In some examples, the fabric treatment composition is a detergent composition or a fabric softening composition. For example, the fabric treatment composition is a detergent composition that contains a detergent selected from among anionic surfactants, nonionic surfactants, zwitterionic surfactants, ampholytic surfactants and cationic surfactants and mixtures thereof. In another example, the fabric treatment composition is a fabric softening composition that contains monomethyl trialkyl quaternaries, imidazolinium quaternaries, dimethyl alkyl benzyl quaternaries, dialkyl dimethyl quaternaries, methyl dialkoxy alkyl quaternaries, diamido amine-based quaternaries and dialkyl methyl benzyl quaternaries or ($C_8$-$C_{24}$) fatty acid amides or any combination thereof.

Provided herein are liquid fabric treatment compositions, containing a fabric softener or fabric conditioner; and a composition containing a sufficient concentration of solavetivone, 5-epi-β-vetivone, a derivative or analog thereof or mixtures thereof, wherein the concentration is sufficient to repel or kill a pest or insect. In some examples, the fabric softener is selected from among monomethyl trialkyl quaternaries, imidazolinium quaternaries, dimethyl alkyl benzyl quaternaries, dialkyl dimethyl quaternaries, methyl dialkoxy alkyl quaternaries, diamido amine-based quaternaries and dialkyl methyl benzyl quaternaries and ($C_8$-$C_{24}$) fatty acid amides and combinations thereof. In some examples, the fabric conditioner contains an anti-static agent, a brightening agent, a bodying agent, a soil-release agent, a wrinkle-release agent or combinations thereof. The anti-static agent can contain a tertiary amine, a quaternary amine, aluminum stearate or combinations thereof. The brightening agent can contain a hydrogen peroxide, potassium permanganate, sodium peroxide, sodium perborate, disulfonated diaminostilbene optical brightener compounds and triazole optical brightener compounds. The bodying agent can be selected from among carboxymethyl cellulose, hydroxyethylcellulose, starch, polyvinyl acetate and combinations thereof. The wrinkle release agent can contain polyvinyl acetate. In such compositions, the solavetivone, 5-epi-β-vetivone or a derivative or analog thereof is present in a concentration from at least or at least about 0.5% to at least or at least about 99%, by weight, of the composition.

Provided herein are fabric refresher spray compositions containing a composition containing a sufficient concentration of solavetivone, 5-epi-β-vetivone, a derivative or analog thereof or mixtures thereof, wherein the concentration is sufficient to repel or kill a pest or insect; and a cyclodextrin. In some examples, the solavetivone, 5-epi-β-vetivone or a derivative or analog thereof is present in a concentration from at least or at least about 0.5% to at least or at least 99%, by weight, of the composition. The fabric refresher spray compositions can further contain an ampholytic surfactant, an anionic surfactant, a cationic surfactant, a nonionic surfactant or a zwitterionic surfactant or combinations thereof.

Provided herein are moist towelette products, containing a woven or non-woven fabric or cellulosic substrate; and a composition containing a sufficient concentration of solavetivone, 5-epi-β-vetivone or a derivative or analog thereof in the form of a solution or emulsion, wherein the concentration is sufficient to repel or kill a pest or insect. In some examples, the solavetivone, 5-epi-β-vetivone or a derivative or analog thereof is present in a concentration from at least or at least about 0.5% to at least or at least about 99%, by weight, of the composition. The moist towelette products can further contain a surfactant that contains cocamidopropyl betaine, coco-glucoside or decyl glucoside or combinations thereof.

BRIEF DESCRIPTION OF THE FIGURES

FIG. 1. FIG. 1A depicts exemplary syntheses of solavetivone (2), 5-epi-β-vetivone (3) and premnaspirodiene (1) from farnesyl pyrophosphate (FPP). FIG. 1B depicts the synthesis of solavetivone (2) from premnaspirodiene (1) through the intermediate solavetivol (4) by HPO. The C5 carbon is indicated by the number 5. *Hyoscyamus muticus* premnaspirodiene synthase (HPS); *Hyoscyamus muticus* premnaspirodiene oxygenase (HPO); and 5-epi-aristolochene dihydroxylase (EAH).

DETAILED DESCRIPTION

Outline

A. Definitions
B. Overview
C. Solavetivone and 5-epi-β-vetivone
  1. Solavetivone
  2. 5-epi-β-vetivone
  3. Derivatives and analogs of solavetivone
D. Methods of production of solavetivone and 5-epi-β-vetivone
  1. Biosynthetic Production of solavetivone
    a. Synthesis of premnaspirodiene
    b. Synthesis of solavetivone
    c. Methods for production in vitro and in vivo
  2. Synthesis of 5-epi-β-vetivone from solavetivone
  3. Chemical Syntheses from organic building blocks
E. Methods of Repelling and Killing Pests
F. Compositions containing solavetivone, 5-epi-β-vetivone and/or derivatives or analogs thereof
  1. Carriers
    a. Liquid Carriers
    b. Gas Carriers
    c. Solid Carriers
  2. Additional Ingredients
    a. Anti-Oxidants
    b. Emulsifiers and Dispersing Agents
    c. Viscosity Modulating Agents
    d. Preservatives
    e. Colorant
    f. Synergists
  3. Microencapsulation
G. Formulations containing (−)-solavetivone, 5-epi-β-vetivone and/or derivatives or analogs thereof
  1. Sprays
  2. Dusts and Granules
  3. Woven or Nonwoven Substrates
  4. Aerosols
  5. Personal Care and Cosmetic Formulations
  6. Insect Repellants
  7. Insecticides and Pesticides
  8. Household Care Formulations
H. Preparation of Compositions and Formulations
I. Examples

A. DEFINITIONS

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the Internet can come and go, but equivalent information can be found by searching the internet. Reference thereto evidences the availability and public dissemination of such information.

As used herein, "pest" refers any organism, typically a small insect or parasite or "bug" or "worm," whose existence it can be desirable to control. Pests include insects and similar organisms, such as nematodes, that are detrimental, annoying or a nuisance to plants or animals, including humans and domesticated animals. Pests can include, for example, arthropod species, such as, for example, an insect, an arachnid, an arachnoid, bugs, flies and parasites. The pest can be a species belonging to an animal order, such as, for example, Acari, Anoplura, Araneae, Blattodea, Coleoptera, Collembola, Diptera, Grylloptera, Heteroptera, Homoptera, Hemiptera:Cimicidae, Hymenoptera, Isopoda, Isoptera, Lepidoptera, Mantodea, Mallophaga, Neuroptera, Odonata, Orthoptera, Psocoptera, Siphonaptera, Symphyla, Thysanura and Thysanoptera. Exemplary pests include ants, bedbugs, carpet beetles, centipedes, chiggers, drain flies, dust mites, earwigs, fleas, flies, gnats, hornets, lice, millipedes, mites, mosquitoes, roaches scabies, silverfish, spiders, stinkbugs, termites, ticks, wasps, weevils and yellow jackets.

As used herein, a "derivative" refers to chemical substance derived from another substance either directly or by modification or partial substitution, and can include differences in one atom, element or group or more than one atom, element or group.

As used herein, an "analog" with respect to chemical compounds refers to a chemical compound that has a similar structure and similar chemical properties to those of another compound, but differs from it by a single atom, element or group.

As used herein, solavetivone is a sesquiterpenoid having the following structure:

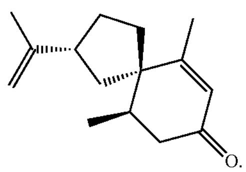 [SMILES: C=C(C)[C@@H]1CC[C@@]2(C1)C(C)=CC(=O)C[C@H]2C]

As used herein, a derivative or analog of solavetivone refers to a solavetivone that has been modified to have one or more differing atoms, elements or groups, or is a chemical compound having a similar structure and chemical property as solavetivone but having one or more differing atoms, elements or groups. For example, 3-hydroxysolavetivone has a hydroxyl group at the 3 position in place of a hydrogen at position 3 of solavetivone. Derivatives and analogs of solavetivone are known to those of skill in the art and include, but are not limited to, 3-hydroxysolavetivone, 3,9-dihydroxysolavetivone, 3-hydroxy-9-(3-methyl-2-butenoyloxy)solavetivone, 3-acetoxysolavetivone, 13-hydroxysolavetivone, 3-acetoxy-9-(2-methylpropionyloxy) solavetivone, 3-hydroxy-9-(3-methylbutanoyloxy) solavetivone, 3-acetoxy-9-(3-methyl-butanoyloxy) solavetivone, 3-acetoxy-9-(3-methyl-2-butenoyloxy) solavetivone, 3-hydroxy-9-tigloyloxysolavetivone, 3-hydroxy-9-isobutanoyloxysolavetivone, 3-beta-acetoxysolavetivone and 3-beta-hydroxysolavetivone.

As used herein, 5-epi-β-vetivone ((5S,10R)-5-epi-β-vetivone) is a sesquiterpenoid having the following structure:

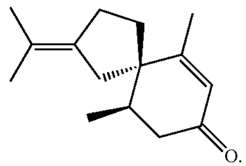 [SMILES: CC1=CC(=O)C[C@@H](C)[C@@]12CCC(=C(C)C)C2]

Reference to 5-epi-β-vetivone does not include β-vetivone (5R,10R-(−)-β-vetivone, (−)-vetivone, 5S,10S-(+)-β-vetivone or (+)-vetivone).

As used herein, a derivative or analog of 5-epi-β-vetivone refers to a 5-epi-β-vetivone that has been modified to have one or more differing atoms, elements or groups, or is a chemical compound having a similar structure and chemical property as 5-epi-β-vetivone but having one or more differing atoms, elements or groups.

As used herein, premnaspirodiene is a sesquiterpene having the following structure:

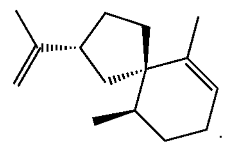

As used herein, "pest control" refers to a disruption in a target pest's status. For example, pest control includes repelling, incapacitating, deterring, eliminating, alleviating, mitigating, reducing the number of, eradicating, knockdown or killing pests.

As used herein, "insecticide" or "pesticide" refer to any compound, composition or formulation that can destroy or kill insects or pests.

As used herein, "insect repellent" or "pest repellent" refer to any compound, composition or formulation conferring on a location protection from insects or pests when compared to no treatment at all. For example, insect and pest repellants prevent, repel, reduce the number of, alleviate or mitigate insects and pests from a location.

As used herein, "repel" when used in the context of "repelling a pest or insect" means to repulse, ward off, drive back or keep away from a treated locus, such that at any given time, there are fewer pests or insects on a treated locus then on an untreated locus under the same conditions. Although a pest may land on or cross over a treated locus, the pest does not stay on the treated locus for a prolonged period of time or does not stay to probe or bite or otherwise damage the locus.

As used herein, "control" when used in the context to "control a pest or insect" means to kill, repel, expel, incapacitate, deter, eliminate, alleviate, reduce in number and/or eradicate.

As used herein, "knockdown" refers to the inability of the pest to move toward heat, indicating that the pest is sickly, but not necessarily dying.

As used herein, "moribund" refers to a pest that is unable to move towards heat at a specified time, such as about or at twenty-four hours, after treatment.

As used herein, "sufficient to kill" refers to an amount or concentration of an agent that is sufficient to kill an organism, such as a pest.

As used herein, "sufficient to repel" refers to an amount or concentration of an agent that is sufficient to repel an organism, such as a pest.

As used herein, "protection" refers to a reduction in numbers of pests, and can, e.g., be usefully determined by measuring mean complete protection time ("mean CPT") in tests in which pest behavior toward treated animals, including humans, and treated inanimate surfaces is observed.

As used herein, "mean CPT" or "mean complete protection time" refers to the mean length of time before the first landing, probing or biting (in the case of a biting pest) or crawling (in the case of a crawling pest such as a tick or chigger) on a treated surface is observed over two or more repetitions of tests. This can be measured using any method or technique known in the art (e.g., see Fradin et al. (2002) *New England Journal of Medicine* 347:13-18).

As used herein, "residual action" refers to the length of time a compound or composition exists in a particular environment and retains activity sufficient to be effective for its intended purpose.

As used herein, "treatment" means any manner in which one or more of the symptoms of a disease or disorder are ameliorated or otherwise beneficially altered. Treatment also encompasses any use of the compositions or formulations herein, such as use for treating, repelling and/or eradicating any pest.

As used herein, "prevention" means to reduce the risk of getting a disease or disorder. Prevention encompasses any use of the compositions or formulations herein, such as use for treating, repelling and/or eradicating any insect or pest thereby preventing the risk of getting a disease or disorder mediated by the pest.

As used herein, "amelioration" of the symptoms of a particular disorder by administration of a particular composition refers to any lessening, whether permanent or temporary, lasting or transient that can be attributed to or associated with administration of the composition. Amelioration encompasses reducing the effects of a pest on an animal, human or surface, such as clothing, bedding or housing materials.

As used herein, "deploying" refers to a method of administration or application of a composition, such as one containing a solavetivone, 5-epi-β-vetivone or a derivative or analog thereof. Methods for deploying include applying topically, atomizing, brushing on, coating, dipping, drenching, dripping, dusting, foaming, infusing, injecting into or onto, pouring, rolling on, scattering, spraying, spreading, sprinkling and wiping the composition onto at least a portion of the location, and combinations thereof.

As used herein, "contacting" refers to bringing two or more materials into close enough proximity such that they can interact. Contacting can be accomplished in a vessel such as a test tube or a Petri dish, or in a room or barn, or in a field.

As used herein, "in the vicinity of" refers to a two locations that are in close enough proximity that they can interact. For example, a composition can deployed in the vicinity of a location such that the composition has an effect on the pests in that location.

As used herein, a "location" or "locus" refers to a person, thing or object on which composition containing a solavetivone, 5-epi-β-vetivone or a derivative or analog thereof is applied. Locations include the surface of the body of a human or animal, such as skin, hair or fur, an article of clothing of a human, bedding, bed boards, bed slats, a mattress, box springs, furniture, carpeting, baseboards, flooring, an air supply duct, an attic, an awning, a basement, a cellar, a crawlspace, a deck, a dock, a garage, a hamper, a heating vent, a home foundation, a linen storage closet, a pool deck, roof tiles, a shipping container, a storage unit, a suitcase, a walkway and a wall space, and combinations thereof.

As used herein, a "bedding location" refers to a location associated with beds or bedding, including, bedding, bed boards, bed slats, a mattress, box springs, furniture, carpeting, baseboards and flooring, or combinations thereof.

As used herein, a "surface of a human or animal" refers to human skin, hair or skin and hair, and animal skin, hair and fur, or combinations thereof.

As used herein, an "additional compound that repels and/or kills pests or insects" refers to chemical-based insect and pest repellants, chemical pesticides and natural pesticides or pest repellants. Additional compounds that repel and/or kill pests or insects include organophosphates, such as malathion, synthetic pyrethroids, such as permethrin, carbamates, lindane, organochlorines, such as dichlorodiphenyltrichloroethane, natural and synthetic plant oils of camphor, eucalyptus, pennyroyal, pyrethrins, N,N-diethyl-meta-toluamide, picaridin (2-(2-hydroxyethyl)-1-piperidinecarboxylic acid 1-methylpropyl ester), citronella oil, cedarwood oil, coumarin, 2-hydroxy-methylcyclohexyl acetic acid lactone, beta-alanine, 2-hydroxymethyl-cyclohexylidene acetic acid lactone, 2-hydroxy-methylcyclohexyl propionic acid lactone, p-menthane-3,8-diol, and 3-[N-butyl-N-acetyl]-aminopropionic acid ethyl ester, and combinations thereof.

As used herein, "animal" is used in the broadest sense as used in the art, and encompasses vertebrates and invertebrates. Animals include, but are not limited to, amphibia, ayes, mammalian and reptilia. An animal can be a vertebrate, such as a mammal, avian or fish. An animal can be a human or a bovine, canine, caprine, cervine, cricetine, feline, galline, equine, lapine, murine, musteline and ovine. An animal can be a human or other mammalian animals include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), antelopes, buffalos, camels, cervine (e.g., deer), donkeys, rabbits, and rodents (e.g., guinea pigs, squirrels, rats, mice, gerbils, and hamsters).

As used herein, "companion animal" refers to an animal kept as a pet for companionship. Companion animals often are dogs, cats or horses, but also can include hamsters, gerbils, rabbits, guinea pigs, rats, mice, pot bellied pigs and pet birds.

As used herein, "mammal" refers to a class of higher vertebrates including man and all other animals that nourish their young with milk secreted by mammary glands and that have skin that is more or less covered with hair. Exemplary mammals include humans, monkeys, rodents, sheep, goats, pigs, dairy and beef cattle, dogs, cats, horses, rabbits, guinea pigs and ferrets.

As used herein, the term "subject" is an animal, typically a mammal or bird. Included are humans, primates, cattle, pigs, rabbits, goats, sheep, mice, rats, guinea pigs, hamsters, cats, dogs, horses, chickens, ducks, turkeys and others.

As used herein, "ectoparasite" refers to parasitic pests that live on the surface of the host. Ectoparasites include, for example, lice, ticks, mites, bed bugs, mosquitoes, horse flies and deer flies.

As used herein, "exoskeleton" refers to an external skeleton that supports and protects an animal's body.

As used herein, "bed bug" refers to one of the parasitic Heteroptera: Cimicidae insects, including the common bedbug (*Cimex lectularius*), tropical bedbug (*Cimex hemipterus*), *Leptocimex boueti*, which infests bats and humans, *Cimex pdosellus, Cimex pipistrella*, and *Haematosiphon inodora.*

As used herein, "lice" refers to insects of the order Phthiraptera, which is sometimes split into the order Anoplura, the sucking lice, and the order Mallophaga, the biting lice. All Phthiraptera are wingless external parasites of birds and mammals.

As used herein, the term "carrier" refers to any solid, liquid or gas with which a solavetivone, 5-epi-β-vetivone or derivative or analog thereof is mixed to facilitate contacting of the solavetivone, 5-epi-β-vetivone or derivative or analog thereof with a location. Carriers include, but are not limited to, any solid, liquid or gas that adheres to a pest or insect and/or any solid, liquid or gas that penetrates the exoskeleton of a pest or insect. A carrier can be used to facilitate storage, transport and/or handling of a composition or formulation.

As used herein, a "delivery vehicle" refers to a liquid, solution, emulsion, suspension, solid, powder, paste, particle or granule that is capable of delivering and contacting a terpene, such as solavetivone, 5-epi-β-vetivone and derivatives and analogs of either to the surface of a subject, such as a human or animal, or to a location such that the terpene contacts and is retained at the surface or location for a sufficient time to repel or kill a pest. The delivery vehicle provides for retention at the location for a sufficient time to at least repel a pest, such as an insect. Delivery vehicles include, but are not limited to, aqueous formulations, emulsions, aerosol formulations, creams, gels, lotions, oils, sprays, soaps, detergents, particulates and substrates that can contact and be retained on the surface of a location where pests occur.

As used herein, a "particulate" refers to a solid, powder, dust or granule that is capable of being impregnated or coated with solavetivone, 5-epi-β-vetivone or derivative or analog thereof, such that the solavetivone, 5-epi-β-vetivone or derivative or analog thereof is present on the surface or infused within the material. Particulates include, but are not limited to, alumina, amorphous silica, attapulgite, calcium carbonate, calcium phosphate, a clay, chalk, diatomaceous earths, fumed silica, a kaolin, kieselguhr, magnesium carbonate, microparticulate cellulose, montmorillonite, pyrophyllite, silicic acid, sodium bicarbonate, sodium carbonate, sodium phosphate, sodium pyrophosphate, talc, and vermiculite.

As used herein, a "substrate" refers to any material that is capable of absorbing or interacting with solavetivone, 5-epi-β-vetivone or derivative or analog thereof, such that the solavetivone, 5-epi-β-vetivone or derivative or analog thereof is present on the surface, coated with, or infused within the material. Substrates include, but are not limited to, paper, cloth, woven or nonwoven materials, infused plastic and absorbent plastic polymers.

As used herein, a "woven material" refers to any material containing weaving.

As used herein, a "nonwoven material" refers to any material that does not contain weaving. Nonwoven materials include, but are not limited to, flexible sheets containing fibers that are adhesively or thermally bonded. Fibers for use in nonwoven materials include, but are not limited to, natural fibers, synthetic fibers and blends of natural and synthetic fibers.

As used herein, an "absorbent plastic polymer" refers to any polymer capable of absorbing a solavetivone, 5-epi-β-vetivone or derivative or analog thereof. An example of an absorbent plastic polymer is a pet collar.

As used herein, an "infused plastic" refers to any plastic that capable of being infused with a solavetivone, 5-epi-β-vetivone or derivative or analog thereof.

As used herein, a "penetration agent" refers to any compound that penetrates the surface or exoskeleton of a pest or insect. Penetration agents include but are not limited to silicone dioxide, petroleum distillate, light solvent naphtha and D-limonene, or combinations thereof.

As used herein, "viscosity" refers to a physical property of a fluid that determines the internal resistance to shear forces; viscosity can be expressed in centipoise (cP).

As used herein, a "viscosity modulating agent" refers to any compound that can modify the viscosity of a composition. Viscosity modulating agents can increase or decrease the viscosity of a composition, modify the rheology of a composition, or stabilize an emulsion or foam.

As used herein, a "viscous fluid" or "gel" refers to a liquid or colloid that has a higher viscosity than a free flowing liquid.

As used herein, a "gelling agent" refers to a compound that facilitates the gelation of a liquid.

As used herein, an "aerosol propellant" refers to any liquefied or compressed gas. Aerosol propellants include, but are not limited to, argon, butane, carbon dioxide, a chlorofluorocarbon, such as dichlorodifluoromethane or dichlorotetrafluoroethane, dimethyl ether, a hydrocarbon, a hydrofluorocarbon, such as difluoromethane, trifluoromethane, difluoroethane, trifluoroethane, tetrafluoroethane, or octafluorocyclobutane, isobutane, nitrogen, propane, or mixtures thereof, butane, dimethyl ether, a fluorocarbon, such as Freon™ gas and carbon dioxide.

As used herein, a "dispersing agent" or "emulsifier" refers to any compound that can promote uniform separation of particles. Typical dispersing agents or emulsifiers are surface active agents or surfactants, polyvinylpyrrolidone, polyoxyethylated castor oil, a polyoxyethylene sorbitan ester, alkylnaphthalene sulfonate, alkylbenzenesulfonate, polyoxyethylene, polycarboxylate, lignin sulfonate, sodium silicate, potassium silicate, methylcellulose, carboxymethyl cellulose, hydroxypropylcellulose, hydroxypropyl-methylcellulose, gum arabic, polyacrylate, and acrylic/maleic copolymers, and combinations thereof.

As used herein, a "surface-active agent" or "surfactant" refers to any compound that reduces surface tension when dissolved in water or water solutions, or that reduces interfacial tension between two liquids, or between a liquid and a solid. Examples of surfactants include anionic, cationic, non-ionic and zwitterionic surfactants, including, but not limited to: (1) fatty acid esters such as glycerol esters, PEG esters, and sorbitan esters, including ethylene glycol distearate, ethylene glycol monostearate, glycerol mono and/or dioleate, PEG dioleate, PEG monolaurate, sorbitan monolaurate, sorbitan trioleate; (2) nonionic ethoxylates such as alkylphenol ethoxylates, alcohol ethoxylates, alkylamine ethoxylates, such as octylphenol ethoxylate, nonylphenol ethoxylate, alkylamine ethoxylates; (3) nonionic surfactants such as 2,4,7,9-tetramethyl-5-decyn-4,7-diol; and (4) ethylene oxide/propylene oxide copolymers.

As used herein, an "antioxidant" refers to any compound that, when added to a composition, increases the length of time the composition is exposed to the environment or decreases any negative impact oxygen or free radicals can have on a composition. Antioxidants include but are not limited to ascorbyl palmitate, butylated p-cresol, tert-butyl-hydroquinone, butylated hydroquinone monomethyl ether, butylhydroxyanisole, butylhydroxytoluene, propyl gallate, tocopherol, ascorbic acid, dibutyl-hydroxy toluene, dihydroquercetin, octyl gallate, dodecyl gallate, ethoxyquin, mixed tocopherols, octadecyl-3-(3,5-ditertiarybutyl-4-hydroxy-phenyl)propionate, pentaerythritol-tetrakis [3-(3,5-ditertiarybutyl-4-hydroxyphenyl)-propionate], 2,5-ditertiary-butyl hydroquinone, 4,4'-thiobis(3-methyl-6-tertiarybutyl phenol) and 2,2'-methylene-bis-(4-methyl-6-tertiarybutyl phenol), and combinations thereof.

As used herein, a "preservative" refers to any compound that can be included in a composition to help preserve the composition. Preservatives include but are not limited to azoles, benzisothiazolin-3-one, benzalkonium quaternary compounds, benzyl alcohol, borates, 2-bromo-2-nitro-propane-1,3-diol, butylparaben, 5-chloro-2-methyl-4-isothiazolin-3-one, chlorphenesin, chloroxylenol, diazolidinyl urea, a dimethyl-benzylalkyl-ammonium chloride, ethylparaben, formaldehyde, glutaraldehyde, halogenated salicylanilides, hexachlorophene, hexylene glycol, isobutylparaben, isothiazolin-3-one, 2-methyl-4-isothiazoline-3-one, methylchloroisothiazolinone, methylisothiazolinone, methylparaben, monochloracetamide, neomycin sulfate, o-phenylphenol and salts thereof, phenoxyethanol, propionic acid and salts thereof, propylparaben, sodium benzoate, sorbic acid and salts thereof, tebuconazole and triazoles, and combinations thereof.

As used herein, a "colorant" refers to any compound that provides a color to a composition. Colorants provide visual clues to the applier of the composition or formulation, such as to help the applier see where the compositions or formulations are being applied to a surface or locus and thereby identifying a coverage area and/or allowing an even distribution of the compositions or formulations on a surface. Colorants include but are not limited to dyes and pigments, such as titanium oxide, titanium dioxide, zinc oxide, white lead, zinc sulfide, aluminum oxide, iron oxide, silicon oxide, zirconium oxide, an azo-type colorant, a condensate-type colorant, a phthalocyanine-type colorant, a quinacridone-type colorant, an insoluble lake pigment, organic dyes, such as alizarin dyes, azo dyes or metal phthalocyanine dyes.

As used herein, a "synergist" refers to any compound that acts to increase or prolong the effects of the compositions without increasing the amount of active ingredient. Synergists include, but are not limited to, bis-(2,3,3,3-tetrachloropropyl)ether, dodecyl imidazole, N-(2-ethylhexyl)bicyclo-[2,2,1]hept-5-ene-2,3-dicarboxyimide piperonyl butoxide, isobornyl thiocyanatoacetate, safroxan and sesame, or combinations thereof.

As used herein, a "softening active agent" or "conditioning agent" refers to any compound used to soften clothes when washed or dried. One class of softening active agents includes the quaternary amines, or "quats" or "quaternaries". Exemplary quaternary amines include the monomethyl trialkyl quaternaries, imidazolinium quaternaries, dimethyl alkyl benzyl quaternaries, dialkyl dimethyl quaternaries, methyl dialkoxy alkyl quaternaries, diamido amine-based quaternaries and dialkyl methyl benzyl quaternaries.

As used herein, the term "detergency builder" refers to an agent that serves to enhance the cleaning capacity or cleansing action of detergent compounds in a cleaning composition. A detergency builder has the property of improving detergency levels in detergent compositions and permit the attainment of cleaning performance that is superior to compositions that do not include a detergency builder.

As used herein, "finely divided" refers to a powder in which the majority (>50%) of the particles therein have a particle size which is less than about 200 μm in diameter.

As used herein, a "granule" refers to porous or nonporous particles (such as crushed rock or stone) as well as agglomerated smaller particles, for example, agglomerated powder particles, that are relatively large, with a particle size which is about 200-2500 microns in diameter typically.

As used herein a "volatile silicone" refers to those silicone materials that have a measurable vapor pressure at 25° C. Such vapor pressures can be in the range from about 0.01 mmHg to about 6 mmHg. Conversely, the term "non-volatile silicone" refers to those silicone materials that do not have a measurable vapor pressure at 25° C.

As used herein, a "composition" refers to any mixture of two or more ingredients. It can be a solution, a suspension, a liquid, a powder, a solid, granulated, an aerosol, a spray, a paste, aqueous, non-aqueous or any combination thereof.

As used herein, a "formulation" refers to any composition that is formulated for a particular purpose. For example, compositions can be formulated as personal care products, cosmetic products and household care products.

As used herein, a combination refers to any association between two or more items.

As used herein, a kit is a packaged combination.

As used herein, fluid refers to any composition that can flow. Fluids thus encompass compositions that are in the form of liquids, semi-solids, pastes, solutions, aqueous mixtures, gels, lotions, creams and other such compositions.

As used herein, an acyclic pyrophosphate terpene precursor is any acyclic pyrophosphate compound that is a precursor to the production of at least one terpene, including, but not limited to, farnesyl-pyrophosphate (FPP), geranyl-pyrophosphate (GPP), and geranylgeranyl-pyrophosphate (GGPP). Acyclic pyrophosphate terpene precursors are thus substrates for terpene synthases.

As used herein, a terpene is an unsaturated hydrocarbon based on the isoprene unit ($C_5H_8$), and having a general formula $C_{5x}H_{8x}$, such as $C_{10}H_{16}$. Reference to a terpene includes acyclic, monocyclic and polycyclic terpenes. Terpenes include, but are not limited to, monoterpenes, which contain 10 carbon atoms; sesquiterpenes, which contain 15 carbon atoms; diterpenes, which contain 20 carbon atoms, and triterpenes, which contain 30 carbon atoms. Reference to a terpene also includes stereoisomers of the terpene. Terpenes include solavetivone, 5-epi-β-vetivone and derivatives and analogs thereof.

As used herein, a terpene synthase is a polypeptide capable of catalyzing the formation of one or more terpenes from a pyrophosphate terpene precursor, for example, farnesyl pyrophosphate (FPP), geranyl pyrophosphate (GPP) or geranylgeranyl pyrophosphate (GGPP).

As used herein, "*Hyoscyamus muticus* premnaspirodiene synthase," "HPS" or vetispiradiene synthase" refers to a protein or polypeptide capable of catalyzing the formation of premnaspirodiene from an acyclic pyrophosphate precursor, typically farnesyl pyrophosphate (FPP). *Hyoscyamus muticus* premnaspirodiene synthases include any known to one of skill in the art. An exemplary *Hyoscyamus muticus* premnaspirodiene synthase has a sequence of amino acids set forth in SEQ ID NO:1.

As used herein, "*Hyoscyamus muticus* premnaspirodiene oxygenase" or "HPO" refers to a protein or polypeptide capable of catalyzing the formation of solavetivone from premnaspirodiene. *Hyoscyamus muticus* premnaspirodiene oxygenases include any known to one of skill in the art. An exemplary *Hyoscyamus muticus* premnaspirodiene oxygenase has a sequence of amino acids set forth in SEQ ID NO:2.

As used herein, "5-epi-aristolochene dihydroxylase" or "EAH" refers to a protein or polypeptide capable of catalyzing the formation of solavetivone from premnaspirodiene. 5-epi-aristolochene dihydroxylases include any known to one of skill in the art. An exemplary 5-epi-aristolochene dihydroxylase has a sequence of amino acids set forth in SEQ ID NO:3.

As used herein, "nucleic acids" or "nucleic acid molecules" include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, the term "polynucleotide" means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, heterologous nucleic acid is nucleic acid that is not normally produced in vivo by the cell in which it is expressed or that is produced by the cell but is at a different locus or expressed differently or that mediates or encodes mediators that alter expression of endogenous nucleic acid, such as DNA, by affecting transcription, translation, or other regulatable biochemical processes. Heterologous nucleic acid is generally not endogenous to the cell into which it is introduced, but has been obtained from another cell or prepared synthetically. Heterologous nucleic acid can be endogenous, but is nucleic acid that is expressed from a different locus or altered in its expression. Generally, although not necessarily, such nucleic acid encodes RNA and proteins that are not normally produced by the cell or in the same way in the cell in which it is expressed. Heterologous nucleic acid, such as DNA, also can be referred to as foreign nucleic acid, such as DNA. Thus, heterologous nucleic acid or foreign nucleic acid includes a nucleic acid molecule not present in the exact orientation or position as the counterpart nucleic acid molecule, such as DNA, found in a genome. It also can refer to a nucleic acid molecule from another organism or species (i.e., exogenous).

Any nucleic acid, such as DNA, that one of skill in the art would recognize or consider as heterologous or foreign to the cell in which the nucleic acid is expressed is herein encompassed by heterologous nucleic acid; heterologous nucleic acid includes exogenously added nucleic acid that also is expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced.

As used herein, a "peptide" refers to a polypeptide that is from 2 to 40 amino acids in length.

As used herein, the amino acids that occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

In keeping with standard polypeptide nomenclature described in *J. Biol. Chem.,* 243:3557-3559 (1968), and adopted by 37 C.F.R. §§1.821-1.822, abbreviations for the amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

All amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual or non-natural amino acids, such as those referred to in 37 C.F.R. §§1.821-1.822. Furthermore, a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound containing an amino group and a carboxylic acid group that is not one of the naturally-occurring amino acids listed in Table 1. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art and can be included in a modified labdenediol diphosphate synthase polypeptides or sclareol synthase polypeptides provided herein.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, "primary sequence" refers to the sequence of amino acid residues in a polypeptide.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound. Methods for purification of the compounds to produce substantially chemically pure compounds are known to those of skill in the art. A substantially chemically pure compound, however, can be a mixture of stereoisomers. In such instances, further purification might increase the specific activity of the compound.

As used herein, isolated or purified polypeptide or protein or biologically-active portion thereof is substantially free of cellular material or other contaminating proteins from the cell of tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as proteolytic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant methods by using recombinant DNA methods refers to the use of the well known methods of molecular biology for expressing proteins encoded by cloned DNA.

As used herein, vector (or plasmid) refers to discrete DNA elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as bacterial artificial chromosomes, yeast artificial chromosomes and mammalian artificial chromosomes. Selection and use of such vehicles are well known to those of skill in the art.

As used herein, expression refers to the process by which nucleic acid is transcribed into mRNA and translated into peptides, polypeptides, or proteins. If the nucleic acid is derived from genomic DNA, expression can, if an appropriate eukaryotic host cell or organism is selected, include processing, such as splicing of the mRNA.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells. Viral vectors include, but are not limited to, adenoviral vectors, retroviral vectors and vaccinia virus vectors.

As used herein, operably or operatively linked when referring to DNA segments means that the segments are arranged so that they function in concert for their intended purposes, e.g., transcription initiates downstream of the promoter and upstream of any transcribed sequences. The promoter is usually the domain to which the transcriptional machinery binds to initiate transcription and proceeds through the coding segment to the terminator.

As used herein, the term assessing or determining includes quantitative and qualitative determination in the sense of obtaining an absolute value for the activity of a product, and also of obtaining an index, ratio, percentage, visual or other value indicative of the level of the activity. Assessment can be direct or indirect.

As used herein, the singular forms "a", "an" and "the" include plural referents unless the context clearly dictates otherwise. Thus, for example, reference to polypeptide, comprising "an amino acid replacement" includes polypeptides with one or a plurality of amino acid replacements.

As used herein, ranges and amounts can be expressed as "about" a particular value or range. About also includes the exact amount. Hence "about 5%" means "about 5%" and also "5%." Whenever a numerical range, such as 1-10 or 5% to 50%, is recited, the range encompasses the entire range bounded by the first and last recited value. For example, "an alkyl of 1 to 20 carbon atoms" means that an alkyl group can contain 1 carbon atom, 2 carbon atoms, 3 carbon atoms, etc., up to and including 20 carbon atoms. Another example includes "a formulation including 1% to 10%, by weight, oil," which means that the formulation includes by weight 1%, 1.1%, 1.2%, 1.3%, 1.4%, 1.5%, 1.6%, 1.7%, 1.8%, 1.9%, 2%, 2.1% . . . , 9.7%, 9.8%, 9.9% or 10% oil.

As used herein, "optional" or "optionally" means that the subsequently described event or circumstance does or does not occur, and that the description includes instances where said event or circumstance occurs and instances where it does not.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description is divided into the subsections that follow.

B. OVERVIEW

Pests are organisms that are detrimental to animals, including humans, domesticated animals and pets, and human concerns, such as crops, because they can serve as vectors for disease, bite or sting, cause annoyance, damage property, including causing structural damage to homes or agricultural products, and result in decreased enjoyment of indoor and outdoor environments. For example, arthropod pests, such as insects and arachnids, have been shown to transmit to humans various types of diseases, including virus, bacterial and protozoal diseases. In another example, bed bugs have become a major issue since the banning of the chemical DDT. In the past four years, bed bugs have made a major resurgence and specifically in the past eighteen months, there have been store, hotel, and business closings due to bed bug infestations.

Chemical-based insect repellents are available that can be applied to skin, clothing, or in the immediate surroundings of a person. Chemical-based insect repellents include DEET (N,N-diethyl-meta-toluamide), which is estimated to be used by one-third of the United States population, organophosphates, such as malathion (S-(1,2-dicarbethoxyethyl)-O,O-dimethyldithiophosphate or ((dimethoxy-phosphinothioyl)thio)butanedioic acid, diethyl ester (CAS No. 121-75-5), synthetic pyrethroids, such as permethrin, carbamates and organochlorines, such as DDT (dichlorodiphenyltrichloroethane) and lindane, and other organic insecticides and inorganic salts (e.g., see U.S. Pat. Nos. 2,423,284, 3,352,664, 3,396,223, 3,515,782, 4,308,279, 4,376,784, 4,948,013, 5,434,189 and 6,048,892).

Despite such wide use of chemical pesticides, there are concerns about the negative impact of DEET and other chemicals. Many of these products contain chemicals that are harmful to humans and animals, such as domesticated animals and pets, and cannot be used for direct or indirect contact. Some pesticides are known carcinogens and others are highly toxic and can be found in the bloodstream of users of such products. Chemical pesticides used on crops, such as DDT, are effective, but have also been found to have a negative effect on humans and the environment. Further, DEET has been found to be less effective in low concentrations and formulations containing effective concentrations have a strong chemical smell. Additionally, resistance to insecticides in arthropods is widespread, with at least 400 species being resistant to one or more insecticides (se, e.g., U.S. Pat. No. 5,571,901).

Natural pesticides can be safer to humans and the environment and have widespread use. Among the natural pest repellents or pesticides that are used are natural and synthetic plant oils of camphor, cedarwood, citronella, eucalyptus and pennyroyal, and the pyrethrins. Plant oils tend to be expensive to isolate in commercial quantities and usually are very volatile, evaporating quickly when applied or exposed to the elements. Additionally, there are reports that some pests are developing a resistance to them. For examples, it is reported that some bedbugs have developed a resistance to pyrethrins and pyrethroids.

There remains a need for safe and effective pesticidal compositions for killing, repelling, destroying or mitigating insects and pests, such as ants, bed bugs, carpet beetles, centipedes, chiggers, drain flies, dust mites, earwigs, fleas, flies, gnats, hornets, lice, millipedes, mites, mosquitoes, scabies, silverfish, spiders, stinkbugs, termites, ticks, wasps, weevils and yellow jackets. In addition, there remains a need for use of such compositions for repelling insects and pests, e.g., from the home, including from bedding, clothing and structures, and for effective insect and pest control, for the short term and when formulated for extended release for long-term insect pest and control.

It has been found herein that the plant phytoalexin solavetivone and the plant terpenoid 5-epi-β-vetivone as well as derivatives and analogs thereof as well as various isomers thereof are effective repellants of insects and pests, such as bed bugs, and also can kill insects and pests. Provided are methods for repelling and/or killing insects and pests by applying/deploying compositions containing solavetivone, 5-epi-β-vetivone or a derivative or analog thereof. Also provided are compositions containing solavetivone, 5-epi-β-vetivone or a derivative or analog thereof for use in repelling, killing or mitigating insects and pests. Among the compositions are those formulated for topical administration to subjects and also compositions that can be applied to locations and products, such as dryer sheets and other matrices, for delivery thereof.

C. SOLAVETIVONE AND 5-EPI-β-VETIVONE

Phytoalexins are antimicrobial substances synthesized by plants in response to pathogen infection. For example, anti-bacterial and anti-fungal substances are produced upon infection with a disease-causing bacteria or fungus. Phytoalexins include phytochemicals such as terpenoids, glycosteroids and alkaloids. One such phytoalexin terpenoid is the sesquiterpenoid solavetivone. 5-epi-β-vetivone is plant terpenoid. Solavetivone and 5-epi-β-vetivone are not constituents of vetiver oil. Further, solavetivone and 5-epi-β-vetivone differ from vetiver oil compounds by the stereochemistry at carbon C5. Solavetivone and 5-epi-β-vetivone have an S configuration at the C5 carbon whereas vetiver oil compounds have an R configuration at the same C5 carbon (see FIG. 1 compounds 2 and 3 for identification of the C5 carbon).

1. Solavetivone

Solavetivone (2, katandinone) is a sesquiterpenoid that is a potent anti-fungal and anti-bacterial phytoalexin. Solavetivone does not have an odor that is perceptible to humans.

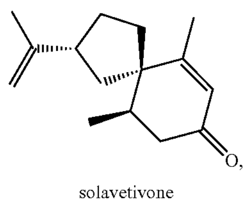

2 solavetivone

Solavetivone has been identified in various plants, including Solanaceous plants such as potato, tobacco, tomato, eggplant and pepper, and sedge. For example, solavetivone has been observed in eggplants as an antibacterial substance resistant against *Verticillium dahliae, Fusarium oxysporum* and *Pseudomonas solanacearum* (see, e.g., U.S. Pat. No. 6,492,303). Solavetivone accumulates heavily in the roots of *Solanum aethiopicum* and *Solanum torvum*, and occurs in and can be isolated from *Solanum jabrense* (see, e.g., da Silva et al. (2002) *Biochemical Systematics and Ecology* 30:1083-1085), *Nicotiana tabacum* (see, e.g., Fujimori et al. (1977) *Phytochemistry* 16:392), *Lycium chinense* (see, e.g., Sannai et al. (1980) *Phytochemistry* 21:2986-2987), *Mandragora* species (see, e.g., Hanus et al. (2005) *Phytochemistry* 66:2408-2417), *Hyoscyamus albus* (see, e.g., Miguel and Barroso (1994) *Phytochemistry* 35:371-375), flue-cured tobacco leaves (see, e.g., Nishikawaji et al. (1983) *Phytochemistry* 22:1819-1820), tobacco leaves infiltrated with *Pseudomonas lachrymans* (see, e.g., Guedes et al. (1980) *Phytochemistry* 21:2987-2988), *Nicotiana rustica* (see, e.g., Uegaki et al. (1980) *Phytochemistry* 19:1229-1230), Solanaceae (see, e.g., Stoessl et al. (1976) *Phytochemistry* 15:855-872), diseased *Solanum tuberosum* (potato) tubers (see, e.g., Coxon et al. (1974) *Tet Lett* 34:2921-2924; Alves et al. (1979) *Plant Physiol* 63:359-362), *Solanum aethiopicum* (see, e.g., Nagase et al. (2001) *Z Naturforxch C* 56:181-187) *Solanum indicum* (see, e.g., Syu et al. (2001) *J Nat Prod* 64:1232-1233), *Cyperus rotundus* (see, e.g., Priya and Padmakumari (2012) *J Chromatogr B Analyt Technol Biomed Life Sci* 904:22-28) and *Solanum abutiloides* (see, e.g., Yokose et al. (2004) *Biosci Biotechnol Biochem* 68:2640-2642).

Solavetivone can be obtained from natural sources. For example, solavetivone can be isolated from culture medium of hairy roots of *Hyoscyamus albus* or *Capsicum annuum* suspension cell cultures upon treatment with methyl jasmonate, copper sulfate or cyclodextrins (see, e.g., Kuroyanagi et al. (1998) *J Nat Prod* 61:1516-1519; Sabater-Jara et al. (2010) *J Plant Physiol* 167:1273-1281) or recovered from *Hyoscyamus muticus* hair root cultures by integrated product extraction (see, e.g., Corry et al. (1993) *Biotechnol Bioeng* 42:503-508). Solavetivone can also be isolated from *Nicotiana tabacum* plants treated with ergosterol, a steroid from fungal membranes (see, e.g., Tugizimana et al. (2012) Molecules 17:1698-1715). In addition, solavetivone can be generated by chemical synthesis, including total synthesis from chemical building blocks or biosynthetically from the vetispirane-type sesquiterpene premnaspirodiene (1, see, FIG. 1), as described in further detail in Section D below.

2. 5-Epi-β-Vetivone 5-epi-β-vetivone (3, (5S,10R)-5-epi-beta-vetivone) is a plant sesquiterpenoid having a vetivert, woody, grapefruit aroma.

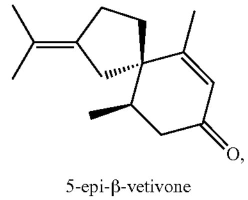

3

5-epi-β-vetivone

3. Derivatives and Analogs of Solavetivone

Derivatives of solavetivone include, but are not limited to, 3-hydroxysolavetivone, 3,9-dihydroxysolavetivone, 3-hydroxy-9-(3-methyl-2-butenoyloxy)solavetivone, 3-acetoxysolavetivone, 13-hydroxysolavetivone, 3-acetoxy-9-(2-methylpropionyloxy)solavetivone, 3-hydroxy-9-(3-methylbutanoyloxy)solavetivone, 3-acetoxy-9-(3-methylbutanoyloxy)solavetivone, 3-acetoxy-9-(3-methyl-2-butenoyloxy)solavetivone, 3-hydroxy-9-tigloyloxysolavetivone, 3-hydroxy-9-isobutanoyloxysolavetivone, 3-beta-acetoxysolavetivone and 3-beta-hydroxysolavetivone (see, e.g., Kawauchi et al. (2010) *Chem Pharm Bull* 58:934-938; Kuroyanagi et al. (1998) *J Nat Prod* 61:1516-1519; Nagase et al. (2001) *Z Naturforxch C* 56:181-187; Yokose et al. (2004) *Biosci Biotechnol Biochem* 68:2640-2642). Such derivatives of solavetivone can be generated by chemical synthesis, including total synthesis from chemical building blocks.

D. METHODS OF PRODUCTION OF SOLAVETIVONE AND 5-EPI-BETA-VETIVONE

Solavetivone and 5-epi-β-vetivone can be produced biosynthetically from farnesyl pyrophosphate by cyclization catalyzed by the terpene synthase *Hyoscyamus muticus* premnaspirodiene synthase followed by oxidation catalyzed by a hydroxylase, such as *Hyoscyamus muticus* premnaspirodiene oxygenase, or chemically by total synthesis by any method known to one of skill in the art. Typically, solavetivone is produced biosynthetically in host cells, such as yeast cells, and 5-epi-β-vetivone is generated from acid-catalyzed isomerization of solavetivone.

1. Biosynthetic Production of Solavetivone

Solavetivone can be synthesized biosynthetically in vitro or in vivo from the acyclic pyrophosphate precursor farnesyl pyrophosphate (FPP) as shown in FIG. 1. In the first step, FPP is cyclized to form premnaspirodiene. Subsequently, premnaspirodiene can be oxidized biosynthetically or chemically to form solavetivone.

a. Synthesis of Premnaspirodiene

Premnaspirodiene can be generated biosynthetically from the farnesyl diphosphate by the terpene synthase *Hyoscyamus muticus* premnaspirodiene synthase (*Hyoscyamus* premnaspirodiene synthase (HPS) or vetispiradiene synthase; Genbank Accession No. U20187; SEQ ID NO:1).

*Hyoscyamus* premnaspirodiene synthase is a terpene synthase that catalyzes the cyclization FPP into premnaspirodiene (see, e.g., Back and Chappell (1995) *J Biol Chem* 270:7375-7381; Takahashi et al. (2007) *Biotechnology and Bioengineering* 97:170-181; see, also U.S. Pat. No. 7,622,614). Premnaspirodiene can be isolated or used directly to generate solavetivone in vivo.

b. Synthesis of Solavetivone

Solavetivone can be generated by the oxidation of premnaspirodiene via either biosynthetic and chemical syntheses. Biosynthetically, premnaspirodiene can be oxidized to solavetivone by oxidation with a hydroxylase or cytochrome P450 oxygenase. In one example, premnaspirodiene can be oxidized to solavetivone by the sesquiterpene hydroxylase 5-epi-aristolochene dihydroxylase (EAH; SEQ ID NO:3) (see, e.g. Greenhagen et al. (2003) *Arch Biochem Biophys* 409:385-394). In another example, premnaspirodiene is oxidized to the terpene alcohol solavetivol (4) and then to solavetivone by the cytochrome P450 oxidase *Hyoscyamus muticus* premnaspirodiene oxygenase (HPO; SEQ ID NO:2) (see, e.g. FIG. 1B; Takahashi et al. (2007) *J Biol Chem* 282:31744-31754; International Patent Publ. No. WO2006079020; and U.S. Pat. No. 7,622,614). Solavetivone can be isolated by extraction with an organic solvent and/or column chromatography.

Chemically, premnaspirodiene can be converted to solavetivone by allylic oxidation (see, e.g., U.S. Pat. No. 7,622,614). The allylic oxidation can be carried out using metal oxidants, including, but not limited to, chromium, copper, rhodium, cobalt, manganese, or vanadium, such as $CrO_3$-pyridine complex, chromium trioxide and 3,5-dimethylpyrazole, chromic acid ($CrO_2Cl_2$) and 3,5-dimethylpyrazole, pyridinium chlorochromate (PCC), pyridinium dichromate (PDC), sodium chromate, sodium dichromate in acetic acid, pyridinium fluorochromate, 3,5-dimethylpyrazolium fluorochromate(VI), copper(I) bromide, copper(I) iodide, $Cu(OAc)_2$ and t-BuOOH, dirhodium catalysts such as dirhodium tetrakiscaprolactamate ($Rh_2(cap)_4$), $Rh_2(OAc)_4$, dirhodium tetrakisperfluorobutanoate $Rh_2(pfb)_4$), $Co(OAc)_2$ and t-BuOOH, $Mn(OAc)_2$ and t-BuOOH, and $V(OAc)_2$ and t-BuOOH. In one example, the allylic oxidation can be achieved by reaction with $CrO_2Cl_2$ in the presence of an organic solvent, such as t-butanol, ethyl ether, dichloromethane or hexane (see, e.g., Hwu and Wetzel (1992) *J Org Chem* 57:922-928). In another example, allylic oxidation can be performed using $CrO_2Cl_2$ in the presence of 3,5-dimethylpyrazole as a catalyst. In yet another example, oxidation is performed using t-butylhydroperoxide and sodium chlorite in a solvent mixture of acetonitrile, water and t-butanol. Solavetivone can be isolated and/or purified from reaction mixtures by thin-layer chromatography, column chromatography, gas chromatography, countercurrent distribution or extraction with an organic solvent c. Methods for Production In Vitro and In Vivo Biosynthetic production can be performed in vitro using purified enzymes, or in vivo in host cells that overexpress the enzymes. For example, premnaspirodiene can be formed in vitro from FPP using *Hyoscyamus muticus* premnaspirodiene synthase that has been expressed and purified from any suitable host cell/expression system. Likewise, solavetivone can be formed in vitro from premnaspirodiene using *Hyoscyamus muticus* premnaspirodiene oxygenase (HPO) or 5-epi-aristolochene dihydroxylase (EAH) that has been expressed and purified from any suitable host cell/expression system.

Such enzymes can be produced by any methods known in the art for protein production including in vitro and in vivo methods such as, for example, the introduction of nucleic acid molecules encoding the enzymes into a host cell or host plant for in vivo production or expression from nucleic acid molecules encoding the enzymes in vitro. Expression hosts include prokaryotic and eukaryotic organisms such as *E. coli*, yeast, plants, insect cells, mammalian cells, including human cell lines and transgenic animals. Expression hosts can differ in their protein production levels as well as the types of post-translational modifications that are on the expressed proteins. The choice of expression host can be made based on these and other factors, such as regulatory and safety considerations, production costs and the need and methods for purification.

Expression in eukaryotic hosts can include expression in yeast such as those from the *Saccharomyces* genus (e.g. *Saccharomyces cerevisiae*) and *Pichia* genus (e.g. *Pichia pastoris*), insect cells such as *Drosophila* cells and lepidopteran cells, plants and plant cells such as citrus, tobacco, corn, rice, algae, and lemna. Eukaryotic cells for expression also include mammalian cells lines such as Chinese hamster ovary (CHO) cells or baby hamster kidney (BHK) cells. Eukaryotic expression hosts also include production in transgenic animals, for example, including production in serum, milk and eggs.

Many expression vectors are available and known to those of skill in the art. The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells. The enzymes also can be utilized or expressed as protein fusions. For example, a fusion can be generated to add additional functionality to a polypeptide. Examples of fusion proteins include, but are not limited to, fusions of a signal sequence, a tag such as for localization, e.g. a $his_6$ tag or a myc tag, or a tag for purification, for example, a GST fusion, GFP fusion or CBP fusion, and a sequence for directing protein secretion and/or membrane association.

Purification of enzymes depends on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary the proteins can be extracted and further purified using standard methods in the art. Premnaspirodiene and/or solavetivone can be isolated by extraction with an organic solvent or column chromatography.

Typically, solavetivone is produced in vivo in host cells that overexpress *Hyoscyamus muticus* premnaspirodiene synthase and/or *Hyoscyamus muticus* premnaspirodiene oxygenase or 5-epi-aristolochene dihydroxylase. Such host cells can be transfected with a dual expression vector, such as pCDF-Duet (Novagen) or pACYC-Duet (Novagen), containing genes encoding for HPS, and for an oxidase or hydroxylase, such as HPO or EAH. Such vectors allow co-expression of two target genes via two multiple cloning sites. Alternatively, host cells can be transfected simultaneously or sequentially with two vectors, one containing a gene encoding for HPS, and the other containing a gene encoding for HPO or EAH.

Host cells suitable for in vivo expression include those that overexpress the acyclic pyrophosphate precursor FPP. For example, suitable host cells include those that produce FPP as part of the mevalonate-dependent isoprenoid biosynthetic pathway (e.g. fungi, including yeast cells, and animal cells) or the mevalonate-independent isoprenoid biosynthetic pathway (e.g. bacteria and higher plants) or, alternatively, any host cell that has been modified to produce FPP, such as a host cell transformed with a farnesyl pyrophosphate synthase. Exemplary of such cells are yeast cells. For example, yeast cells that have been modified to produce less squalene synthase or less active squalene synthase (e.g. erg9 mutants; see e.g. U.S. Pat. Nos. 6,531,303, 6,689,593, 7,838,279 and 7,842,497) are useful for in vivo production of solavetivone as described herein. Reduced squalene synthase activity results in accumulation of FPP in the host cell at higher levels compared to wild type yeast cells, thus allowing for increased yields of premnaspirodiene and solavetivone. Exemplary modified yeast cells include, but are not limited to, modified *Saccharomyces cerevisiae* strains YPH499 (MATa, ura3-52, lys2-801, ade2-101, trp1-Δ63, his3-Δ200, leu2-Δ1), WAT11 (MATa, ade2-1, his3-11,-15; leu2-3,-112, ura3-1, canR, cyr+; containing chromosomally integrated Arabidopsis NADPH-dependent P450 reductase ATR1; see Pompon et al. (1995) *Toxicol Lett* 82-83:815-822; Ro et al. (2005) *Proc Natl Acad Sci USA* 102:8060-8065); and BY4741 (MATa, his3Δ1, leu2Δ0, met15Δ0, ura3Δ0; ATCC #201388). The host cells can be cultured using any suitable method well known in the art.

A variety of fermentation methodologies can be utilized for the production of premnaspirodiene and/or solavetivone from yeast cells expressing the enzymes. For example, large scale production can be effected by either batch or continuous fermentation. A classical batch fermentation is a closed system where the composition of the medium is set at the beginning of the fermentation and not subject to artificial alterations during the fermentation. Thus, at the beginning of the fermentation the medium is inoculated with the desired microorganism or microorganisms and fermentation is permitted to occur without further addition of nutrients. Typically, the concentration of the carbon source in a batch fermentation is limited, and factors such as pH and oxygen concentration are controlled. In batch systems the metabolite and biomass compositions of the system change constantly up to the time the fermentation is stopped. Within batch cultures cells typically modulate through a static lag phase to a high growth log phase and finally to a stationary phase where growth rate is diminished or halted. If untreated, cells in the stationary phase will eventually die.

A variation on the standard batch system is the Fed-Batch system, which is similar to a typical batch system with the exception that nutrients are added as the fermentation progresses. Fed-Batch systems are useful when catabolite repression tends to inhibit the metabolism of the cells and where it is desirable to have limited amounts of substrate in the medium. Also, the ability to feed nutrients will often result in higher cell densities in Fed-Batch fermentation processes compared to Batch fermentation processes. Factors such as pH, dissolved oxygen, nutrient concentrations, and the partial pressure of waste gases such as $CO_2$ are generally measured and controlled in Fed-Batch fermentations.

Production of the premnaspirodiene and/or solavetivone also can be accomplished with continuous fermentation. Continuous fermentation is an open system where a defined fermentation medium is added continuously to a bioreactor and an equal amount of conditioned medium is removed simultaneously for processing. This system generally maintains the cultures at a constant high density where cells are primarily in their log phase of growth. Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems aim to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art.

Following cell culture, the cell culture medium then can be harvested to obtain the produced premnaspirodiene and/or solavetivone. Premnaspirodiene and/or solavetivone can be isolated by extraction with organic solvent or column chromatography.

2. Synthesis of 5-Epi-β-Vetivone from Solavetivone

5-Epi-β-vetivone can be synthesized by acid-catalyzed isomerization of solavetivone, as described in U.S. Pat. No. 7,622,614. Acidic isomerization reagents include, but are not limited to, mineral acids, organic protonic acids and Lewis acids. For example, the acidic isomerization reagent can be selected from among, but not limited to, phosphoric acid, sulfuric acid, perchloric acid, hydrohalide acids, such as hydrogen chloride, hydrogen bromide and hydrogen iodide, heteropolyacids, such as $H_3[P(W_3O_{10})_4]$, carboxylic acids, sulfonic acid, trifluoroacetic acid, acetic acid and methylsulfonic acid, or mixtures thereof, such as a mixture of acetic acid and sulfuric acid. Acids and acid mixtures suitable for use in the isomerization reaction are known to one of skill in the art. In some examples, a solid phase acidic isomerization reagent is used, such as, for example, montmorillonite clay, acidic resins, Dowex® 50, Amberlyst® IR-15 and Naflon® perfluorinated resin. Other acids suitable for use as a reagent for the isomerization of solavetivone include, but are not limited to, acidic aluminum oxide, trifluoroboronetherate, tin chloride and titanium tetrachloride. An appropriate range of reaction time and reaction temperature is necessary in order to produce 5-epi-β-vetivone. A reaction time that is too short will result in low yield of 5-epi-β-vetivone, since not all of the premnaspirodiene will be converted to the desired end-product, 5-epi-β-vetivone. A reaction time that is too long will drive the reaction toward production of a mixture of the 2,6 diene and 1,6 diene isomers. Typically, the reaction time is between at or about 15 minutes and at or about 120 minutes, such as between at or about 40 minutes and at or about 60 minutes, and the reaction temperature is between at or about 25° C. and at or about 150° C., such as between at or about 75° C. and at or about 105° C. (see, e.g., U.S. Pat. No. 7,622,614). 5-epi-β-vetivone can be isolated and/or purified from the reaction mixtures by thin-layer chromatography, column chromatography, gas chromatography, countercurrent distribution or extraction with an organic solvent.

3. Chemical Syntheses from Organic Building Blocks

Solavetivone and 5-epi-β-vetivone can be synthesized chemically by any method known to one of skill in the art. Solavetivone can be generated synthetically, for example, by silicon-promoted ring contraction (see, e.g., Hwu and Wetzel (1992) *J Org Chem* 57:922-928); total synthesis from (R)-carvone (see, e.g., Srikrishna et al. (2005) *Tet Lett* 46:7373-7376); total synthesis using an enantioselective copper-catalyzed conjugate addition of $Me_3Al$ to a cyclohexa-2,5-dienone intermediate (see, e.g., Takemoto et al. (1996) *Chem Commun* 14:1655-1656; Takemoto et al. (1997) Tetrahedron 53:606-616); total synthesis from a spiro ketone precursor (see, e.g., Yamada et al. (1977) *J Chem Soc Chem Commun* 554-555); spiro-annelation and regio- and stereo-selective reduction of a spiro-dienone (see, e.g., Iwata et al. (1981) *J Chem Soc Chem Commun* 463-465); synthesis from a bicyclo-octenediol (see, e.g., Murai et al. (1982) *J Chem Soc Chem Commun* 32-33) and stereoselective formation by π-cyclization from 3,5-dimethylanisole (see, e.g., Murai et al. (1981) *Tet Lett* 22:1033-1036). Total synthesis of 5-epi-β-vetivone using an enantioselective copper-catalyzed conjugate addition of $Me_3Al$ to a cyclohexa-2,5-dienone intermediate is described in Takemoto et al. ((1997) *Tetrahedron* 53:606-616).

Solavetivone and 5-epi-β-vetivone can be isolated and/or purified from reaction mixtures by thin-layer chromatography, column chromatography, gas chromatography, countercurrent distribution or extraction with an organic solvent.

E. METHODS OF REPELLING AND KILLING PESTS

Provided herein are methods of repelling and/or killing pests, such as insects, by contacting the pests with solavetivone, 5-epi-β-vetivone or a derivative or analog thereof. It is shown herein that solavetivone, 5-epi-β-vetivone or a derivative or analog thereof have pesticide and pest repellant activity, such as, but not limited to, the capacity or activity to incapacitate, deter, eliminate, alleviate, mitigate, reduce the number of, eradicate or kill pests, including insects.

Methods provided herein include contacting pests, such as insects, with solavetivone, 5-epi-β-vetivone or a derivative or analog thereof, or a mixture thereof, whereby the pests are repelled, incapacitated, deterred, eliminated, alleviated, mitigated, reduced in number, eradicated or killed when the pests come into contact with the composition or formulation, or vapors of the composition or formulation. In such methods, the pests and solavetivone, 5-epi-β-vetivone or a derivative or analog thereof need only be in close enough proximity that they can interact. For example, the solavetivone, 5-epi-β-vetivone or a derivative or analog thereof can be deployed in the vicinity of the pests, whereby the solavetivone, 5-epi-β-vetivone or a derivative or analog thereof has an effect on the pests, e.g., the pests, such as insects, are repelled, incapacitated, deterred, eliminated, alleviated, mitigated, reduced in number, eradicated or killed. The amount of solavetivone, 5-epi-β-vetivone or derivative or analog thereof required to repel and/or kill a pest, such as an insect, can be determined empirically and depends on the targeted pest and the manner in which it is deployed or applied and the locus or location of application.

Methods provided herein also include providing a composition or formulation containing a solavetivone, 5-epi-β-vetivone or a derivative or analog thereof to a location and deploying the composition or formulation at the location in an amount sufficient to repel, incapacitate, deter, eliminate, alleviate, mitigate, reduce the number of, eradicate or kill pests, whereby the pests are repelled, incapacitated, deterred, eliminated, alleviated, mitigated, reduced in number, eradicated or killed when the pests come into contact with the composition or formulation, or vapors of the composition or formulation.

The deploying step can include any method by which the pest, such as an insect, is contacted with solavetivone, 5-epi-β-vetivone or a derivative or analog thereof, such as by atomizing, brushing on, coating, dipping, drenching, dripping, dusting, foaming, infusing, injecting into or onto, pouring, rolling on, scattering, spraying, spreading, sprinkling, washing with or wiping the composition or formulation onto at least a portion of the location. The amount of solavetivone, 5-epi-β-vetivone or derivative or analog thereof required to repel and/or kill a pest can be determined empirically and depends on the targeted pest and the manner in which it is deployed and the locus of application. For some pests, including insects, a composition or formulation, such as those described herein, containing from at least or at least about 0.1% to at least or at least about 100%, or from at least or at least about 0.1% to at least or at least about 95%, such as between at or about 0.1% and at or about 50%, such as, for example, between at or about 0.1% to at or about 50%, or at or about 0.1% to at or about 25%, or at or about 0.1% to at or about 20%, or at or about 0.1% to at or about 15%, or at or about 0.1% to at or about 10%, or at or about 0.1% to at or about 5%, or at or about 0.5% to at or about 95%, or at or about 0.5% to at or about 50%, or at or about 0.5% to at or about 25%, or at or about 0.5% to at or about 20%, or at or about 0.5% to at or about 15%, or at or about 0.5% to at or about 10%, or at or about 0.5% to at or about 5%, or at or about 1% to at or about 95%, or at or about 1% to at or about 50%, or at or about 1% to at or about 25%, or at or about 1% to at or about 20%, or at or about 1% to at or about 15%, or at or about 1% to at or about 10%, or at or about 1% to at or about 5%, or at or about 5% to at or about 95%, or at or about 5% to at or about 50%, or at or about 5% to at or about 25%, or at or about 5% to at or about 20%, or at or about 5% to at or about 15%, or at or about 5% to at or about 10%, or at or about 10% to at or about 95%, or at or about 10% to at or about 50%, or at or about 10% to at or about 25%, or at or about 10% to at or about 20%, or at or about 10% to at or about 15%, or at or about 15% to at or about 50%, or at or about 15% to at or about 25%, or at or about 15% to at or about 20%, or at or about 20% to at or about 50%, or at or about 20% to at or about 25%, or at or about 25% to at or about 50%, or at or about 50% to at or about 95%, or at or about 50% to at or about 100%, solavetivone, 5-epi-β-vetivone or derivative or analog thereof, by weight, of the composition or formulation, is a pest repelling/killing amount. In some examples, a pest repellent contains at least or about at least 0.1% solavetivone, 5-epi-β-vetivone or derivative or analog thereof, by weight, of the composition or formulation. In other examples, a pesticide contains at least or about at least 1% solavetivone, 5-epi-β-vetivone or derivative or analog thereof, by weight, of the composition or formulation. Various modifications of the method can be made, such as modifying the amount of solavetivone, 5-epi-β-vetivone or derivative or analog thereof in the composition or formulation.

In the methods provided herein to repel, incapacitate, deter, eliminate, alleviate, mitigate, reduce the number of, eradicate or kill an insect or pest, the pest can be any targeted pest, including, but not limited to, Siphonaptera insects, such as cat flea (*Ctenocephalides felis*), dog flea (*Ctenocephalides canis*), oriental rat flea (*Xenopsylla cheopis*), human flea (*Pulex irritans*), chigoe (*Tunga penetrans*) and European rat flea (*Nosopsyllus fasciatus*); Anoplura insects, such as head louse (*Pediculus humanus capitis*), crab louse (*Pthirus pubis*), short-nosed cattle louse (*Haematopinus eurysternus*), sheep louse (*Dalmalinia ovis*), hog louse (*Haematopinus suis*), long-nosed cattle louse (*Linognathus vituli*), cattle biting louse (*Bovicola bovis*), poultry shaft louse (*Menopon gallinae*), poultry body louse (*Menacanthus stramineus*), little blue cattle louse (*Solenopotes capillatus*), *Haematopinus* spp., *Linognathus* spp., *Pediculus* spp., *Phtirus* spp. and *Solenopotes* spp.; Acarina insects, such as bush tick (*Haemaphysalis longicornis*), *Haemaphysalis flava, Dermacentor taiwanicus*, American dog tick (*Dermacentor variabilis*), *Ixodes ovatus, Ixodes persulcatus*, black legged tick (*Ixodes scapularis*), lone star tick (*Amblyomma americanum*), *Boophilus microplus, Rhipicephalus sanguineus, Ixodes holocyclus*, western black legged tick (*Ixodes pacificus*), *Dermacentor andersoni, Amblyomma maculatum*, ear mite (*Octodectes cynotis*), *Psoroptes* spp., *Chorioptes* spp., *Otodectes* spp., *Sarcoptes* spp., *Notoedres* spp., *Knemidocoptes* spp., *Sacroptes scabiei, Demodex* spp., follicle mite (*Demodex canis*), northern fowl mite (*Ornithonyssus sylviarum*), poultry red mite (*Dermanyssus gallinae*), *Trombicula* spp., *Leptotrombidium akamushi, Ornithodorus hermsi, Ornithodorus turicata, Ornithonyssus bacoti, Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Cytodites* spp. and *Laminosioptes* spp.; Heteroptera insects, such as common bedbug (*Cimex lectularius*), tropical bedbug (*Cimex hemipterus*), *Reduvius senilis, Triatoma* spp. *Rhodnius* spp., *Panstrongylus* spp., and *Arilus critatus*; and Mallophage (Amblycera and Ischnocera) insects, such as *Trimenopon* spp., *Menopon* spp., *Trinoton* spp., *Bovicola* spp., *Werneckiella* spp., *Lepikentron* spp., *Trichodectes* spp. and *Felicola* spp. In particular, provided are methods to repel and/or kill an insect selected from among ants, bed bugs, carpet beetles, centipedes, chiggers, drain flies, dust mites, earwigs, fleas, flies, gnats, hornets, lice, millipedes, mites, mosquitoes, roaches, scabies, silverfish, spiders, stinkbugs, termites, ticks, wasps, weevils and yellow jackets. Ants include, for example, Argentine ants, black ants, carpenter ants, fire ants, odorous house ants, pavement ants and pharaoh ants. Lice include, for example, head lice, body lice, pubic lice and nits thereof.

In the methods provided herein, the solavetivone, 5-epi-β-vetivone or a derivative or analog thereof, or compositions or formulations containing solavetivone, 5-epi-β-vetivone or a derivative or analog thereof, can be applied to a locus, such as a subject, for a time sufficient to repel/kill the pests. The amount of time to kill a pest is dependent on the targeted pest, but generally application to the infested area can be for 8 hours or less, such as for at least or at least about 1, 2, 3, 4, 5, 6, 7 or 8 hours. In some methods, the solavetivone, 5-epi-β-vetivone or a derivative or analog thereof, or compositions or formulations thereof, is applied for at least about 30 minutes or less, such as for about 20 minutes, or 15 minutes, or 10 minutes or 5 minutes or less. In some methods, the solavetivone, 5-epi-β-vetivone or a derivative or analog thereof, or compositions or formulations thereof, can be applied more than once, if required. In some methods, the solavetivone, 5-epi-β-vetivone or a derivative or analog thereof, or compositions or formulations thereof, can be applied periodically or intermittently, such as, as a preventative, such as every week, every two weeks, every month or every other month. The solavetivone, 5-epi-β-vetivone or a derivative or analog thereof, or compositions or formulations thereof, can be applied to a location, such as a surface, as a single application or can be applied to a location, such as a surface, two or more times in one day or over the course of several days. The solavetivone, 5-epi-β-vetivone or a derivative or analog thereof, or compositions or formulations thereof, can be formulated for delivery of solavetivone, 5-epi-β-vetivone or derivative or analog thereof for at least or at least about 1, 2, 3, 4, 5, 6, 7, 8, 9, 10, 12, 14, 16, 18, 20, 22 or more hours, including 1 day, or at least or at least about 2 days, or at least or at least about 3 days, or at least or at least about 4 days, or at least or at least about 5 days, or at least or at least about 6 days, at least or at least about 7 days, or at least or at least about 8 days, or at least or at least about 9 days, or at least or at least about 10 days, or at least or at least about 11 days, or at least or at least about 12 days, at least or at least about 13 days, for at least or at least about 14 days, or at least or at least about 15 days, or at least or at least about 16 days, or at least or at least about 17 days, or at least or at least about 18 days, or at least or at least about 19 days, at least or at least about 20 days, or at least or at least about 21 days, or at least or at least about 22 days, or at least or at least about 23 days, or at least or at least about 24 days, or at least or at least about 25 days, at least or at least about 26 days, or at least or at least about 27 days, or at least or at least about 28 days, or at least or at least about 29 days, or at least or at least about 30 days, or at least or at least about 31 days, or at least or at least about 45 days, or at least or at least about 60 days or at least or at least about 75 days or at least or at least about 90 days.

The methods herein can apply compositions containing solavetivone, 5-epi-β-vetivone or a derivative or analog thereof that can be formulated to release solavetivone, 5-epi-β-vetivone or derivative or analog thereof over a given length of time, depending on the application area. For example, in some applications, the compositions provided herein used in the methods to repel and/or kill pests, such as insects, can be formulated for delivery of solavetivone, 5-epi-β-vetivone or derivative or analog thereof for an extended period of time, such as for at least at or about 1 hour, or at least at or about 2 hours, or at least at or about 3 hours, or at least at or about 4 hours, or at least at or about 5 hours, or at least at or about 6, hours, or at least at or about 7 hours, or at least at or about 8 hours, or at least at or about 9 hours, or at least at or about 10 hours, or at least at or about 11 hours, or at least at or about 12 hours, or at least at or about 13 hours, or at least at or about 14 hours, or at least at or about 15 hours, or at least at or about 16 hours, or at least at or about 17 hours, or at least at or about 18 hours, or at least at or about 19 hours, or at least at or about 20 hours, or at least at or about 21 hours, or at least at or about 22 hours, or at least at or about 23 hours, or at least at or about 1 day, or at least at or about 2 days, or at least at or about 3 days, or at least at or about 4 days, or at least at or about 5 days, or at least at or about 6 days, at least at or about 7 days, or at least at or about 8 days, or at least at or about 9 days, or at least at or about 10 days, or at least at or about 11 days, or at least at or about 12 days, at least at or about 13 days, for at least at or about 14 days, or at least at or about 15 days, or at least at or about 16 days, or at least at or about 17 days, or at least at or about 18 days, or at least at or about 19 days, at least at or about 20 days, or at least at or about 21 days, or at least at or about 22 days, or at least at or about 23 days, or at least at or about 24 days, or at least at or about 25 days, at least at or about 26 days, or at least at or about 27 days, or at least at or about 28 days, or at least at or about 29 days, or at least at or about 30 days, or at least at or about 31 days, or at least at or about 45 days, or at least at or about 60 days, or at least at or about 75 days, or at least at or about 90 days, or at least at or about 4 months, or at least at or about 5 months, or at least at or about 6 months, or at least at or about 7 months, or at least at or about 8 months, or at least at or about 9 months, or at least at or about 10 months, or at least at or about 11 months or at least at or about 1 year.

In the methods provided herein, the solavetivone, 5-epi-β-vetivone or a derivative or analog thereof, or compositions or formulations thereof provided herein, can be applied to any location or locus, such as a surface of a subject or object. In some methods, the solavetivone, 5-epi-β-vetivone or a derivative or analog thereof, or compositions or formulations thereof, are applied to a surface of the body of a subject, such as a human or animal. The animal can be a companion animal, such as a dog, cat, horse or rabbit or other animal kept by a human as a pet, or a domesticated or farm animal, such as a cow, cattle, bison, pig, horse, sheep, goat, turkey or chicken. The animal can be a bovine, canine, caprine, cervine, cricetine, feline, galline, equine, lapine, murine, musteline or ovine. In some methods, the solavetivone, 5-epi-β-vetivone or a derivative or analog thereof, or compositions or formulations thereof provided herein, are applied to an article of clothing of a human, or to a bedding material, such as sheets, linens, blankets or pillows. In some methods, the compositions or formulations containing a solavetivone, 5-epi-β-vetivone or a derivative or analog thereof are deployed by laundering an article of clothing of a human with a detergent and/or fabric softener formulation. In some methods, the compositions or formulations containing a solavetivone, 5-epi-β-vetivone or a derivative or analog thereof are deployed by drying an article of clothing of a human with fabric softener formulation provided herein. The fabric softener used in the methods can be provided in the form of a liquid, a gel or a flexible woven or nonwoven sheet.

In some methods, the location, e.g., surface, to which the solavetivone, 5-epi-β-vetivone or a derivative or analog thereof, or compositions or formulations thereof provided herein are deployed is skin, hair or fur or an animal. The compositions or formulations containing a solavetivone, 5-epi-β-vetivone or a derivative or analog thereof can deployed by applying topically to the skin, hair or fur, and the composition can be provided as an aerosol, a solution, an emulsion, an oil, a lotion, a soap, a spray, or a gel. In some methods, the composition containing a solavetivone, 5-epi-β-vetivone or a derivative or analog thereof is provided in a formulation selected from among skin conditioners, hand/body/facial lotions, skin moisturizers, skin toners, skin sanitizers, skin cleansing compositions, skin soothing and lubricating compositions, sunscreen products, anti-aging products, tanning products, self-tanning products, after-sun products, masking products, anti-wrinkle products, hair conditioners, hair styling gels, hair anti-dandruff compositions, hair growth promoter compositions, hair lotions, hair tonics, rinses, conditioners, hair colorant compositions, hair anti-frizzing agent compositions, hair shining compositions, mousses, styling gels, hair pomade products and hair sprays, soaps, foaming bath products, hand/body/facial cleansers, astringent cleansers, anti-acne products, body shampoos, synthetic detergent bars, shower gels and shampoos.

In a particular method provided herein, the solavetivone, 5-epi-β-vetivone or a derivative or analog thereof, or compositions or formulations thereof provided herein target pests, including insects, such as bed bugs, that have invaded a bedding location. In such methods, one or more of the compositions or formulations provided herein are deployed onto bedding (sheets, blankets, linen, pillows), bed boards, bed slats, a mattress, box springs, furniture, carpeting, baseboards or flooring or a combination thereof. The compositions or formulations can be deployed using any appropriate method, such as by atomizing, brushing on, coating, dipping, drenching, dripping, dusting, foaming, infusing, injecting into or onto, pouring, rolling on, scattering, spraying, spreading, sprinkling or wiping. For example, in some methods deploying the composition or formulation includes spraying the composition or formulation on to the surface of bedding, such as a sheet, linen, blanket or pillow, bed boards, bed slats, a mattress, box springs, furniture, carpeting, baseboards or flooring, or a combination thereof. In some methods, the compositions or formulations are injected into the interior of the targeted locus, such as the interior of a pillow, mattress, box springs, furniture, carpeting, baseboards or flooring, or a combination thereof.

The locus selected for deploying the solavetivone, 5-epi-β-vetivone or a derivative or analog thereof, or compositions or formulations thereof provided herein can be determined based on the pest targeted to be repelled or killed. For example, when the pest is a termite, a location for deploying a composition or formulation provided herein can include any wood structure, wooden object or wall space. For most pests, treatment of any one or more of the following locations can be effective to repel or kill the pest: an air supply duct, an attic, an awning, a basement, a cellar, a crawlspace, a deck, a dock, a garage, a hamper, a heating vent, a home foundation, a linen storage closet, a pool deck, roof tiles, a shipping container, a storage unit, a suitcase, a walkway and a wall space. In the methods provided, the solavetivone, 5-epi-β-vetivone or a derivative or analog thereof, or compositions or formulations thereof provided herein can be deployed by any technique known in the art, such as by atomizing, coating, dipping, drenching, dripping, dusting, foaming, infusing, injecting into or onto, pouring, rolling on, scattering, spraying, spreading, sprinkling or wiping the composition or formulation onto or into at least a portion of the location. When the locus to be treated is a surface, the solavetivone, 5-epi-β-vetivone or a derivative or analog thereof, or compositions or formulations thereof provided herein can be applied by spraying, wiping or dusting the surface. In some methods, the composition is deployed by providing it in a form of an absorbent substrate (such as a woven or nonwoven fabric or cellulosic material) or gel and positioning it in the location.

Among the methods provided herein are methods of repelling bedbugs. These methods include contacting the bedbugs with solavetivone, 5-epi-β-vetivone or derivative or analog thereof, such as by deploying a compositions or formulations, such as those described herein, including for example, those that contain from at least or about 0.1% to up to at or about 100% of solavetivone, 5-epi-β-vetivone or a derivative or analog thereof, or mixtures thereof. For example, the methods include contacting bedbugs or areas likely to inhabited by bedbugs with solavetivone, 5-epi-β-vetivone or a derivative or analog thereof, or compositions or formulations thereof, such as any described herein, including any containing from at least or at least about 0.1% to at or about 10%, or greater than at or about 10%, or greater than at or about 15%, or greater than at or about 20%, or greater than at or about 25%, or greater than at or about 50% solavetivone, 5-epi-β-vetivone or derivative or analog thereof; whereby bedbugs are repelled when contacted with the composition or formulation solavetivone, 5-epi-β-vetivone or derivative or analog thereof, or vapors from the composition or formulation solavetivone, 5-epi-β-vetivone or derivative or analog thereof.

In the methods provided herein, the composition or formulation containing a solavetivone, 5-epi-β-vetivone or derivative or analog thereof can be deployed by applying it topically to an article of clothing of a human; or applying it topically to skin or hair of a human; or applying it topically to skin or fur of an animal. In the methods provided, the animal can be any animal, such as a bovine, canine, caprine, cervine, cricetine, feline, galline, equine, lapine, murine, musteline and ovine. The animal can be a human or a companion animal. In the methods provided, the composition or formulation containing a solavetivone, 5-epi-β-vetivone or derivative or analog thereof provided herein can be deployed by laundering an article of clothing of a human with a detergent or fabric softener or both formulated to contain the composition; or by drying an article of clothing of a human with a fabric softener formulated to contain the composition. The composition can be deployed by applying to bedding (sheets, blankets, linens, pillows), bed boards, bed slats, a mattress, box springs, furniture, carpeting, baseboards or flooring, or a combination thereof. The composition can be deployed by spraying the composition on to the surface of bedding, bed boards, bed slats, a mattress, box springs, furniture or carpeting; or injecting the composition into the pillow, mattress, box springs, furniture or carpeting or a combination thereof; or deploying an absorbent substrate or gel containing the composition in the vicinity of bed boards, bed slats, a mattress, box springs, furniture or carpeting so that vapors from the composition come into contact with a surface of the bed boards, bed slats, a mattress, box springs, furniture or carpeting; or injecting the composition into a wall space.

Also provided are methods of preventing skin injury due to biting pests, such as biting insects, where the methods include providing a composition or formulation containing solavetivone, 5-epi-β-vetivone or derivative or analog thereof, such as any described herein. For example, a composition or formulation that contains at least or at least about 0.1% to at or about 10%, or greater than at or about 10%, or greater than at or about 15%, or greater than at or about 20%, or greater than at or about 25%, or greater than at or about 50% solavetivone, 5-epi-β-vetivone or derivative or analog thereof, by weight, of the composition or formulation; and applying the composition or formulation to a location, such as a surface, whereby the pest is repelled from the location when it comes into contact with the composition or with vapors from the composition or formulation. The composition or formulation containing a solavetivone, 5-epi-β-vetivone or derivative or analog thereof can be applied to the surface by atomizing, coating, dipping, drenching, dripping, dusting, foaming, infusing, injecting into or onto, pouring, rolling on, scattering, spraying, spreading, sprinkling or wiping an amount of the composition or formulation onto the surface. In some methods the location is a surface that is bedding, e.g., sheets, linens, blankets, pillows, or clothing or a mattress. In some methods, the composition or formulation can be applied by washing the clothing or bedding with a composition provided herein that is provided as a detergent or fabric softener formulation or both or by drying the clothing or bedding with a fabric softener formulation. In some methods, the composition can be applied by atomizing, coating, dipping, drenching, dripping, dusting, foaming, infusing, injecting into or onto, pouring, rolling on, scattering, spraying, spreading, sprinkling or wiping the composition or formulation onto the surface.

The composition or formulation containing a solavetivone, 5-epi-β-vetivone or derivative or analog thereof can be provided in a form selected from among skin conditioners, hand/body/facial lotions, skin moisturizers, skin toners, skin sanitizers, skin cleansing compositions, skin soothing and lubricating compositions, sunscreen products, anti-aging products, tanning products, self-tanning products, after-sun products, masking products, anti-wrinkle products, hair conditioners, hair styling gels, hair anti-dandruff compositions, hair growth promoter compositions, hair lotions, hair tonics, rinses, conditioners, hair colorant compositions, hair anti-frizzing agent compositions, hair shining compositions, mousses, styling gels, hair pomade products and hair sprays, soaps, foaming bath products, hand/body/facial cleansers, astringent cleansers, anti-acne products, body shampoos, synthetic detergent bars, shower gels and shampoos. Particular pests that are to be repelled and/or killed include ants, bedbugs, chiggers, fleas, lice, mites, mosquitoes, roaches, scabies, and ticks.

Also provided are method for killing a pest, such as an insect, where the methods include providing a pesticide, e.g., insecticide, formulation containing a composition provided herein that contains at least or at least about 1% to at least or at least about 100%, such as up to or about or at 10%, or greater than 10%, or greater than 15%, or greater than 20%, or greater than 25%, or greater than 50% solavetivone, 5-epi-β-vetivone or derivative or analog thereof by weight of the composition; and applying the composition to the pest, whereby the pest is killed.

Also provided are methods of treating a structure infested with pests, e.g., insects, such as termites, where the methods include deploying a composition provided herein that includes solavetivone, 5-epi-β-vetivone or derivative or analog thereof to the infested structure, whereby the composition kills or repels the termites. In some methods, the concentration of the solavetivone, 5-epi-β-vetivone or derivative or analog thereof is between at least or at least about 0.1% and at or about 10%, or greater than 10%, or greater than 15%, or greater than 20%, or greater than 25%, or greater than 50%, by weight, of the composition. Some methods include as a step removing the soil from around at least a portion of the structure to expose at least a portion of the foundation; applying to the exposed foundation any one or more of the compositions provided herein; and replacing to soil to cover the exposed foundation; wherein the composition forms a barrier to deter migration of termites into the structure.

Also provided are methods for treating a subject infested with a pest or insect, where the methods include providing any one or more of the compositions or formulations provided herein that contains at least or at least about 0.1% to at or about 10%, or greater than 10%, or greater than 15%, or greater than 20%, or greater than 25%, or greater than 50% solavetivone, 5-epi-β-vetivone or derivative or analog thereof, by weight, of the composition; and applying the composition or formulation to a surface of the subject, wherein the insect or pest is repelled from the surface or killed when it comes into contact with the composition or formulation, or with vapors from the composition or formulation. The subject can be an animal, such as a human or a companion animal. The composition can be applied to the skin, hair or fur to kill or repel chiggers, fleas, lice, mites, mosquitoes, roaches and scabies.

The methods herein can result in at or about 90%, 95% or 100% knockdown on contact or within at or about 5, 15, 30 or 60 minutes of contact. For some insects or pests, the pesticidal compositions or formulations provided herein can result in at or about or at least 75%, 80%, 85%, 90%, 95% or 100% mortality of the insect or pest. In some applications, the mortality occurs within at or about 1 hour of application, or within at or about 2 hours, 3 hours, 4 hours, 5 hours, 6 hours, 7 hours, 8 hours, 8 hours, 10 hours, 11 hours, 12 hours, 13 hours, 14 hours, 15 hours, 16 hours, 17 hours, 18 hours, 19 hours, 20 hours, 21 hours, 22 hours, 23 hours or 24 hours of application.

F. COMPOSITIONS CONTAINING SOLAVETIVONE, 5-EPI-β-VETIVONE AND/OR DERIVATIVES OR ANALOGS THEREOF

Provided herein are pest repellent compositions, including insect repellent compositions, containing solavetivone or 5-epi-β-vetivone in a suitable carrier. The compositions can be administered/applied in methods for repelling, incapacitating, deterring, eliminating, alleviating, mitigating, reducing the number of, eradicating, knockdown or killing pests, e.g., insects. In some examples, the compositions contain derivatives or analogs of solavetivone or 5-epi-β-vetivone, including, but not limited to, 3-hydroxysolavetivone, 3,9-dihydroxysolavetivone, 3-hydroxy-9-(3-methyl-2-butenoyloxy)solavetivone, 3-acetoxysolavetivone, 13-hydroxysolavetivone, 3-acetoxy-9-(2-methylpropionyloxy) solavetivone, 3-hydroxy-9-(3-methylbutanoyloxy) solavetivone, 3-acetoxy-9-(3-methyl-butanoyloxy) solavetivone, 3-acetoxy-9-(3-methyl-2-butenoyloxy)solavetivone, 3-hydroxy-9-tigloyloxysolavetivone, 3-hydroxy-9-isobutanoyloxysolavetivone, 3-beta-acetoxysolavetivone and 3-beta-hydroxysolavetivone. The provided compositions contain solavetivone, 5-epi-β-vetivone or a derivative or analog thereof in an effective amount, e.g. in an amount sufficient to repel, incapacitate, deter, eliminate, alleviate, mitigate, reduce the number of, eradicate or kill pests, including insects. The provided compositions are suitable for application to an animal, such as human skin, or to inanimate surfaces, such as clothing or bed sheets. Suitable compositions typically include the active ingredient, e.g., solavetivone, 5-epi-β-vetivone or a derivative or analog thereof, and a carrier and can be formulated as a lotion, gel, cream, aerosol or spray, or can be included on a silacaceous clay, talc or granule, or in woven or nonwoven substrates, such as dryer sheets. The compositions can also contain additional components or ingredients, such as anti-oxidants, emulsifiers, viscosity modulating agents, preservatives, colorants and synergists, or combinations thereof. In some examples, the active ingredient in the compositions, e.g., the solavetivone, 5-epi-β-vetivone or derivative or analog thereof, is encapsulated or microencapsulated. The provided compositions can be formulated into a variety of personal, household and home care formulations, including but not limited to, sprays, dusts and granules, woven or nonwoven substrates, aerosols, personal care and cosmetic formulations, pest repellants, insect repellants, insecticides and pesticides, and household care formulations.

The amount of solavetivone, 5-epi-β-vetivone or derivative or analog thereof included in the provided compositions can vary so long as the compositions are effective in repelling, incapacitating, deterring, eliminating, alleviating, mitigating, reducing the number of, eradicating or killing pests, e.g., insects. In some examples, the amount of solavetivone, 5-epi-β-vetivone or derivative or analog thereof is between at or about at least 0.1% and at or about 10%, 15%, 20% or more, by weight, of the composition. In other examples, the amount of solavetivone, 5-epi-β-vetivone or derivative or analog thereof is increased in order to provide faster or longer control, such as knockdown, repelling or killing of a pest, including an insect. For example, the compositions can contain higher amounts of solavetivone, 5-epi-β-vetivone or derivative or analog thereof, for example, at or about 10% or greater than at or about 10%, such as at least or about 15%, at or about 20%, at or about 25%, or at or about 50% solavetivone, or greater than at or about 50% 5-epi-β-vetivone or derivative or analog thereof, by weight, of the composition. Higher amounts of active ingredient, such as solavetivone, 5-epi-β-vetivone or derivative or analog thereof, can be included in order to prolong the residual action of the composition or increase the effect thereof.

The provided compositions are effective for controlling pests, including insects, over a given length of time, depending on the desired application and area. For example, the compositions provided herein can be formulated for delivery of solavetivone, 5-epi-β-vetivone or a derivative or analog thereof for an extended period of time, such as for at least or about 1 hour to at or about 30 days, such as for at or about 1 hour to at or about 3 weeks, or at or about 1 hour to at or about 2 weeks, or at or about 1 hour to at or about 1 week, or at or about 1 hour to at or about 4 days, or at or about 6 hours to at or about 30 days, such as for at or about 6 hours to at or about 3 weeks, or at or about 6 hours to at or about 2 weeks, or at or about 6 hours to at or about 1 week, or at or about 6 hours to at or about 4 days, or at or about 12 hours to at or about 4 weeks, or at or about 12 hours to at or about 3 weeks, or at or about 12 hours to at or about 2 weeks, or at or about 12 hours to at or about 1 week, or at or about 12 hours to at or about 4 days, or at or about 12 hours to at or about 2 days, or at or about 12 hours to at or about 24 hours, or at or about 24 hours to at or about 4 weeks, or at or about 24 hours to at or about 3 weeks, or at or about 24 hours to at or about 2 weeks, or at or about 24 hours to at or about 1 week, or at or about 24 hours to at or about 4 days, or at or about 24 hours to at or about 2 days, or between at or about 1 day to at or about 3 days, or between at or about 2 days and at or about 4 days, or between at or about 2 days and at or about 7 days, or between at or about 1 week and at or about 4 weeks, or between at or about 1 week and at or about 3 weeks, or between at or about 1 week and at or about 2 weeks, or for longer periods of time, such as for at least at least at or about 31 days, or at least at or about 45 days, or at least at or about 60 days or at least at or about 75 days or at least at or about 90 days, or at least at or about 4 months, or at least at or about 5 months or at least at or about 6 months or at least at or about 7 months, or at least at or about 8 months, or at least at or about 9 months or at least at or about 10 months or at least at or about 11 months or at least at or about 1 year.

For example, the provided compositions are effective at repelling, incapacitating, deterring, eliminating, alleviating, mitigating, reducing the number of, eradicating or killing pests, e.g., insects, for at least at or about 30 minutes, or at least at or about 45 minutes, or at least at or about 1 hour, or at least at or about 2 hours, or at least at or about 3 hours, or at least at or about 4 hours, or at least at or about 5 hours, or at least at or about 6 hours, or at least at or about 7 hours, or at least at or about 8 hours, or at least at or about 9 hours, or at least at or about 10 hours, or at least at or about 11 hours, or at least at or about 12 hours, or at least at or about 13 hours, or at least at or about 14 hours, or at least at or about 15 hours, or at least at or about 16 hours, or at least at or about 17 hours, or at least at or about 18 hours, or at least at or about 19 hours, or at least at or about 20 hours, or at least at or about 21 hours, or at least at or about 22 hours, or at least at or about 23 hours, or at least at or about 1 day, or at least at or about 2 days, or at least at or about 3 days, or at least at or about 4 days, or at least at or about 5 days, or at least at or about 6 days, at least at or about 7 days, or at least at or about 8 days, or at least at or about 9 days, or at least at or about 10 days, or at least at or about 11 days, or at least at or about 12 days, at least at or about 13 days, for at least at or about 14 days, or at least at or about 15 days, or at least at or about 16 days, or at least at or about 17 days, or at least at or about 18 days, or at least at or about 19 days, at least at or about 20 days, or at least at or about 21 days, or at least at or about 22 days, or at least at or about 23 days, or at least at or about 24 days, or at least at or about 25 days, at least at or about 26 days, or at least at or about 27 days, or at least at or about 28 days, or at least at or about 29 days, or at least at or about 30 days, or longer.

Provided herein are compositions containing an active ingredient, e.g., solavetivone, 5-epi-β-vetivone or a derivative or analog thereof, and a carrier suitable for application to a subject or to a location or matrix for application to a subject or location. The solavetivone, 5-epi-β-vetivone or derivative or analog of each can be included in an amount between at or about at least 0.1% to at or about 99.9%, such as between at or about 0.1% and at or about 50%, such as, for example, between at or about 0.1% to at or about 50%, or at or about 0.1% to at or about 25%, or at or about 0.1% to at or about 20%, or at or about 0.1% to at or about 15%, or at or about 0.1% to at or about 10%, or at or about 0.1% to at or about 5%, or at or about 0.5% to at or about 50%, or at or about 0.5% to at or about 25%, or at or about 0.5% to at or about 20%, or at or about 0.5% to at or about 15%, or at or about 0.5% to at or about 10%, or at or about 0.5% to at or about 5%, or at or about 1% to at or about 50%, or at or about 1% to at or about 25%, or at or about 1% to at or about 20%, or at or about 1% to at or about 15%, or at or about 1% to at or about 10%, or at or about 1% to at or about 5%, or at or about 5% to at or about 50%, or at or about 5% to at or about 25%, or at or about 5% to at or about 20%, or at or about 5% to at or about 15%, or at or about 5% to at or about 10%, or at or about 10% to at or about 50%, or at or about 10% to at or about 25%, or at or about 10% to at or about 20%, or at or about 10% to at or about 15%, or at or about 15% to at or about 50%, or at or about 15% to at or about 25%, or at or about 15% to at or about 20%, or at or about 20% to at or about 50%, or at or about 20% to at or about 25%, or at or about 25% to at or about 50%, or at or about 50% to at or about 95%, or at least or at least about 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 99% or 99.9% solavetivone, 5-epi-β-vetivone or derivative or analog thereof, by weight, of the composition.

In some examples, the compositions containing solavetivone, 5-epi-β-vetivone or a derivative or analog thereof include an additional active compound that repels and or kills pests, e.g., insects, such as N,N-diethyl-meta-toluamide (DEET), picaridin (2-(2-hydroxyethyl)-1-piperidinecarboxylic acid 1-methylpropyl ester), citronella oil, camphor oil, cedarwood oil, coumarin, 2-hydroxy-methylcyclohexyl acetic acid lactone, beta-alanine, 2-hydroxymethyl-cyclohexylidene acetic acid lactone, 2-hydroxy-methylcyclohexyl propionic acid lactone, p-menthane-3,8-diol, and 3-[N-butyl-N-acetyl]-aminopropionic acid ethyl ester, and combinations thereof. The additional compound can be included in an amount of from at or about 0.1% to at or about 25%, by weight, typically at least 1% to 10%, 15%, 20%, 25%, by weight, of the composition.

The action of the compositions containing a solavetivone, 5-epi-β-vetivone or derivative or analog thereof provided herein can be modulated by selection of the carrier and/or addition of other components/ingredients. For example, when the carrier includes or is a solvent, a solvent having a particular vapor pressure or a combination of solvents having differing vapor pressures can be used to modify the evaporative rate or vaporization rate of the active agent from the composition. In other examples, the compositions contain other components that modulate the residual action of the solavetivone, 5-epi-β-vetivone or derivative or analog thereof. For example, a surfactant with which the active ingredient, e.g., the solavetivone or 5-epi-β-vetivone, can interact can be included in the composition, which can reduce the rate of evaporation and thereby increase the residual action of the composition. Polymers and thickeners and other viscosity modulating agents also can be included in the composition to modulate the viscosity of the composition, and thereby slow the release of the solavetivone, 5-epi-β-vetivone or derivatives or analogs thereof from the composition or otherwise prolong the time that the insect/pest is exposed to the composition or vapors from the composition.

1. Carriers

The compositions provided herein containing a solavetivone, 5-epi-β-vetivone or derivative or analog thereof include a carrier. In general, any material that can be used as a carrier for a volatile essential oil is suitable as a carrier in the compositions and formulations provided herein. The carrier generally is mixed with the solavetivone, 5-epi-β-vetivone or derivative or analog thereof and generally is selected to facilitate the application of the composition to a targeted locus, such as a subject or location, or to facilitate storage, transport and/or handling of the composition. The carrier can be in the form of solid and/or liquid and/or gas, such as a propellant.

For an insect repellent to be effective, the evaporation rate of the active ingredient from the host's skin or the treated surface or locus or article must be sufficiently high to provide a vapor density that has the desired effect on the target insects or pests. There is a balance that should be considered between evaporation rate and the desired duration of the insect repellent effect. If the evaporation rate is too high, the solavetivone, 5-epi-β-vetivone or derivative or analog thereof will be depleted from the surface rapidly, causing a loss in efficacy. There are a number of factors that can modulate evaporation rate, such as the ambient temperature, the temperature of the treated surface, and the presence or absence of air movement. These factors should be taken into consideration when formulating a product, but generally are beyond the direct control of the formulator. The compositions provided herein can be formulated to have a surface evaporation rate of at least a minimum effective evaporation rate, and generally can have a minimum effective evaporation rate that lasts at least four hours. In some compositions, particularly for application to a skin surface, the compositions can provide a minimum effective evaporation rate that lasts at least 0.5, 1, 2, 3, 4, 5, 6, 7, 8, 9, 10, 11, 12, 13, 14, 15, 16, 17, 18, 19, 20, 21, 22, 23 or 24 hours or more.

One skilled in the art can determine an optimal concentration of carrier to be included in the composition or formulation. The carrier can be a fluid, which can include liquids, gases or solids, such as finely divided particulates. One skilled in the art can select the appropriate form of particular dosage preparations for specific application made therefrom, such as solutions, emulsions, suspensions, powders, pastes, and granules which are thus ready for use. The carrier can be up to 99.9%, by weight, of the composition. In some examples, the composition can include at least at or about 10% carrier. In other examples, the composition can include carrier in any amount between at or about 0.1% and at or about 99.9%, by weight, of the composition. For example, the composition can include carrier in an amount of between at or about 0.1% to at or about 50%, by weight, between at or about 0.1% to at or about 30%, by weight, between at or about 1% to at or about 80%, by weight, between at or about 1% to at or about 50%, by weight, between at or about 1% to at or about 30%, by weight, between at or about 10% to at or about 80%, by weight, between at or about 20% to at or about 70%, by weight, between at or about 30% to at or about 60%, by weight, between at or about 10% to at or about 40%, by weight, between at or about 30% and at or about 70%, by weight, or between at or about 60% to at or about 90%, by weight, or between at or about 60% to at or about 99.9%, by weight, of the composition.

a. Liquid Carriers

In some examples, the compositions and formulations provided herein include a liquid carrier. Exemplary liquid carriers include alcohols, alkanes, alkenes, aqueous solutions, cycloalkanes, esters, ethers, glycols, ketones, oils, organic solvents, silicones or silicone oils, and combinations thereof. In some applications, the liquid carrier contains up to at or about 99.9% by weight of the composition. For example, the compositions contain at least at or at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% liquid carrier, by weight, of the composition.

In some examples, the carrier includes an alcohol. Exemplary alcohols that can be included in the compositions and formulations provided herein include, but are not limited to, aromatic alcohols, a $C_1$-$C_8$ monohydric alcohols, such as methanol, ethanol, propanol, isopropanol, butanol, sec-butanol and tert-butanol, $C_2$-$C_6$ polyhydric alcohols, polyvalent alcohols, such as glycerol, and mixtures thereof. In some examples, the carrier is a glyceride, that is a monoglyceride, a diglyceride, an acetylated monoglyceride, or a triglyceride or a combination thereof.

In some examples, the carrier is an alcohol that is a 1-propanol, 2-propanol, 1-butanol, 2-butanol, 2-methyl-1-propanol, 1-pentanol, 2-pentanol, 3-methyl-1-butanol, 3-methyl-2-butanol, ethylene glycol, propylene glycol, 1,4-butanediol, 1,3-butanediol, 2-methyl-1,3-propanediol, 1,4-cyclohexanedimethanol, diethylene glycol, triethylene glycol, PEG-200, PEG-300, PEG-400, PEG-600, 2-methoxyethanol, 2-ethoxyethanol, 2-propoxyethanol, 2-isopropoxyethanol, 2-butoxyethanol, 1-methoxy-2-propanol, 1-ethoxy-2-propanol, 3-methoxy-1-butanol, diethylene glycol monomethyl ether, diethylene glycol monoethyl ether, diethylene glycol mono-n-propyl ether, diethylene glycol mono-isopropyl ether, diethylene glycol monobutyl ether, triethylene glycol monomethyl ether, glycerol, 3-methoxy-1,2-propanediol, or 3-ethoxy-1,2-propanediol. In other examples, the carrier can be a borneol, citronellol, geraniol, D-limonene, dipentene or a combination thereof.

For some pests, the carrier should contain little to no isopropanol. It has been determined that, for killing or repelling some pests, e.g., insects, compositions and formulations that do not contain isopropanol are advantageous. Thus, in some applications, the amount of isopropanol in the composition or formulation does not exceed at or about 5%, or is at or about 4% or less, or is at or about 3% or less, or is at or about 2% or less, or is at or about 1% or less, and in some compositions and formulations isopropanol is not included. In some applications, the total amount of isopropanol in the compositions or formulations is at or about 5% or less, or at or about 1% or less.

In some examples, the carrier also includes a $C_1$-$C_{10}$ alkane, a $C_1$-$C_{10}$ alkene and/or a $C_1$-$C_8$ cycloalkane. In other examples, the carrier includes an ester. Exemplary esters that can be included in the compositions and formulations as a carrier include, but are not limited to, acetate, benzoate esters, butyrate, isobutyrate, caproate, isocaproate, hexanoate, heptanoate, octanoate, phenylacetate, propionate, isopropionate, valerate and isovalerate. In yet other examples, the carrier includes an ether. Exemplary ethers that can be included in the compositions and formulations as a carrier include, but are not limited to, diethyl ether, isopropyl ether and n-propyl ether, and combinations thereof.

In some examples, the carrier includes a glycol. Exemplary glycols that can be included in the compositions and formulations as a carrier include, but are not limited to, butylene glycol, butylene glycol monomethyl ether, butylene glycol dimethyl ether, butylene glycol monoethyl ether, butylene glycol diethylether, ethylene glycol, ethylene glycol monomethyl ether, ethylene glycol dimethyl ether, ethylene glycol monoethyl ether, ethylene glycol diethylether, diethylene glycol, methylene glycol, methylene glycol monomethyl ether, methylene glycol dimethyl ether, propylene glycol, propylene glycol monomethyl ether, propylene glycol dimethyl ether, propylene glycol monoethyl ether, propylene glycol diethyl ether, pentylene glycol and hexylene glycol, and combinations thereof.

In some examples, the carrier includes a ketone. Exemplary ketones that can be included in the compositions and formulations as a carrier include, but are not limited to, acetone, acetophenone, methyl ketone, benzyl methyl ketone, cyclohexanone, ethyl ketone, 3-methylacetophenone, methyl ethyl ketone, methyl propyl ketone, methyl isopropyl ketone, methyl butyl ketone, 4-phenylcyclohexanone, and combinations thereof.

The carrier also can include an oil. Exemplary oils that can be included in the compositions and formulations as a carrier include, but are not limited to, short-chain fatty acid triglycerides, silicone oils, petroleum fractions or hydrocarbons such as heavy aromatic naphtha solvents, light aromatic naphtha solvents, hydro-treated light petroleum distillates, paraffinic solvents, mineral oil, alkylbenzenes, paraffinic oils, and vegetable/plant oils and their derivatives, such as almond oil, avocado oil, canola oil, cashew oil, cherry seed oil, cocoa butter, coconut oil, corn oil, cottonseed oil, flaxseed oil, grape seed oil, jojoba oil, macadamia nut oil, olive oil, palm oil, palm fruit oil, peanut oil, rapeseed oil, rice bran oil, safflower oil, sesame oil, soybean oil, sunflower oil, and walnut oil, and alkylated vegetable oils and alkyl esters of fatty acids, such as methyloleate, and combinations thereof.

In some examples, the carrier includes a silicone or a silicone oil. Exemplary silicones or silicone oils that can be included in the compositions and formulations as a carrier include, but are not limited to, cyclical silicones, linear, branched open chained silicones volatile silicones, such as dimethicone copolyol, cyclomethicone, polydimethylsiloxane, cyclic dimethyl polysiloxane, aminosilicones, phenylsilicones, diphenyldimethicones, phenyltrimethicones, cyclopentasiloxane, a polymer of dimethyl-siloxane with polyoxyethylene and/or polyoxypropylene, dimethicone copolyol, cetyldimethicone copolyol, cetyl dimethicone, cetyl dimethiconecopolyol and dimethiconol, and non-volatile silicones, such as cyclic polydimethylsiloxanes containing an average of from about 3 to about 9 silicon atoms and linear polydimethylsiloxanes containing an average of from about 3 to about 9 silicon atoms, polydimethylsiloxane, phenylated silicones, decamethylcyclopentasiloxane, dodecamethylcyclohexasiloxane and octamethyl-cyclotetrasiloxane and cyclosiloxane substituents selected from among hexamethyl cyclotrisiloxane, octamethyl cyclotetrasiloxane, decamethyl cyclopentasiloxane, dodecamethyl cyclohexasiloxane, tetradecamethyl cycloheptasiloxane, hexadecamethyl cyclooctasiloxane, tetramethyl cyclotetrasiloxane, pentamethyl cyclopentasiloxane, pentamethyl cyclotetrasiloxane, hexamethyl cyclotetrasiloxane, heptamethyl cyclotetrasiloxane, hexamethyl cyclopenta-siloxane, octamethyl cyclopentasiloxane, heptamethyl cyclopentasiloxane, nonamethyl cyclopentasiloxane, cyclomethicone, trisiloxane, volatile dimethicones, polyalkylsiloxanes, polydialkylsiloxanes, methyl trimethicone, cyclopolysiloxanes, and mixtures thereof.

The oil carriers can be used to slow down early evaporation of the solavetivone, 5-epi-β-vetivone or derivatives or analogs thereof from the composition, thereby leaving more solavetivone, 5-epi-β-vetivone or derivatives or analogs thereof available for later evaporation and release into the vicinity of application. Incorporation of an oil in a composition in sufficient amounts to slow the migration of the solavetivone, 5-epi-β-vetivone or derivatives or analogs thereof out of the composition when applied can increase the composition's length of effectiveness by, for example 25% to 50%, over comparable non-entrapped products. When a composition includes too much oil as a carrier, however, it can be perceived as feeling greasy.

Liquid carriers also can provide water repellency and thereby extend the effectiveness of the composition on a targeted locus, such as human skin. Some liquid carriers, in particular some vegetable oils, can help to prevent skin irritation, and/or soothe and condition skin. Factors to consider when selecting a carrier(s) for the compositions and formulations provided herein include commercial availability, cost, repellency, evaporation rate, odor, and stability. Some carriers can themselves have repellent properties.

b. Gas Carriers

In some applications, the carrier in the compositions and formulations is or includes a gas. Generally, the gas is provided in the form of a propellant that can be a liquid when contained in a container under pressure, and converts to a gas upon removal of the pressure. For example, halogenated or unhalogenated gaseous aliphatic hydrocarbons and mixtures thereof can be liquefied at 20° C. by use of an excess pressure of at least 0.5 atmosphere. Exemplary gas carriers for use in the compositions and formulations include, but are not limited to, aerosol propellants, such as argon, butane, carbon dioxide, a chlorofluorocarbon, such as dichlorodifluoromethane or dichlorotetrafluoroethane, dimethyl ether, a hydrocarbon, a hydrofluorocarbon, such as difluoromethane, trifluoromethane, difluoroethane, trifluoroethane, tetrafluoroethane, or octafluorocyclobutane, isobutane, nitrogen, propane, or mixtures thereof, butane, dimethyl ether, a fluorocarbon, such as Freon™ gas and carbon dioxide. The amount of gas carrier included in the compositions and formulations can vary, and can be selected based on any one of several criteria, including the physical behavior of the propellant, on the type of nozzle or device selected to deploy the composition, and on the volume of the pressure vessel used. The proportion of gas carrier in the compositions and formulations can vary from between at or about 10% to at or about 90%, by weight, of the composition.

c. Solid Carriers

The carrier in the compositions and formulations also can be dispersible finely divided solid carriers, such as solid carriers having a particle size of less than about 200 microns, 100 microns, or generally less than 50 microns. Examples of solid carriers include, but are not limited to, finely divided organic solid material or finely divided inorganic solid material, for example, alumina, amorphous silica, attapulgite, calcium carbonate, calcium phosphate, clay, chalk, i.e., calcium carbonate, bentonite, fumed silica, clays, diatomaceous earth, fullers earth, kaolin, magnesium carbonate, microparticulate cellulose, montmorillonite, pyrophyllite, silicic acid, sodium bicarbonate, sodium carbonate, sodium phosphate, sodium pyrophosphate, talc, vermiculite, hydrated aluminum silicate, quartz, silica (amorphous or fumed), silicates, and smectite clay.

The carriers also can be granules of naturally occurring materials or substrates such as crushed rock or stone (calcite, marble, pumice), shredded paper or paper fibers, plant materials, such as ground corn cobs, peanut shells, saw dust or synthetic materials, such as nylon fibers. Granules can be porous or nonporous or a combination thereof. The granule particles can be of any desired size, which can be determined according to the targeted end use of the product. Generally, granules have a mean diameter of less than 5000 microns, and often are in the range of between 500 microns and 2500 microns. When granules are a part of the carrier system, the compositions and formulations containing solavetivone, 5-epi-β-vetivone or derivatives or analogs thereof can be applied to a surface of a nonporous granule or on the surface and/or interior of a porous granule. When a solid carrier system is used, the compositions and formulations can include components that can assist the compositions and/or formulations to adhere to the solid carrier. Such components can include, for example, any viscosity modulating agent. In some applications, a film forming agent, such as gum arabic, polyvinyl acetate, propylene glycol alginate or cellulosic material, is included in the compositions or formulations to adhere the compositions or formulations to the particulate carrier.

2. Additional Ingredients

In some applications, the compositions and formulations provided herein include additional ingredients, such as antioxidants, dispersing agents, emulsifiers, viscosity modulating agents, preservatives, colorants and synergists, or combinations thereof.

a. Antioxidants

An antioxidant can be included in the compositions and formulations provided herein to increase the length of time the deployed compositions or formulations can be exposed to the environment or to decrease any negative impact oxygen or free radical thereof can have on the compositions or formulations. Exemplary antioxidants that can be included in the compositions and formulations provided herein include, but are not limited to, ascorbyl palmitate, butylated p-cresol, tert-butylhydroquinone, butylated hydroquinone monomethyl ether, butylhydroxyanisole, butylhydroxytoluene, propyl gallate, tocopherol, ascorbic acid, dibutyl-hydroxy toluene, dihydroquercetin, octyl gallate, dodecyl gallate, ethoxyquin, mixed tocopherols, octadecyl-3-(3,5-ditertiarybutyl-4-hydroxy-phenyl)propionate, pentaerythritol-tetrakis [3-3,5-ditertiarybutyl-4-hydroxyphenyl)-propionate], 2,5-ditertiary-butyl hydroquinone, 4,4'-thiobis(3-methyl-6-tertiarybutyl phenol) and 2,2'-methylene-bis-(4-methyl-6-tertiarybutyl phenol), and combinations thereof. Typically, an antioxidant can be included in the provided compositions and formulations in a protective amount, typically the lowest effective amount, such as, but are not limited to, between at or about 0.001% to at or about 5%, between at or about 0.005% to at or about 2.5%, or between at or about 0.01% to at or about 1%, by weight, of the composition.

b. Emulsifiers and Dispersing Agents

In some applications, the compositions and formulations provided herein can include an emulsifier and/or dispersing agent. The emulsifier and/or dispersing agent can serve any one or more functions in the compositions and formulations. For example, an emulsifier and/or dispersing agent can help to stabilize an emulsion formed between hydrophobic and hydrophilic components of the application. An emulsifier and/or dispersing agent also can serve as a wetting agent, to enable the compositions and formulations to more easily coat a substrate or targeted locus. An emulsifier and/or dispersing agent also can serve as an auxiliary to form a foam. Typically, a dispersing agent or emulsifier can be included in the provided compositions and formulations in an amount between at or about 0.002% to at or about 50%, by weight, of the composition, such as, for example, between at or about 0.025% to at or about 25%, or between at or about 0.01% to at or about 15%, by weight, of the composition.

Dispersing agents that can be included in the compositions and formulations include, for example, surfactant, polyvinylpyrrolidone, polyoxyethylated castor oil, a polyoxyethylene sorbitan ester, alkylnaphthalene sulfonate, alkylbenzenesulfonate, polyoxyethylene, polycarboxylate, lignin sulfonate, sodium silicate, potassium silicate, methylcellulose, carboxymethyl cellulose, hydroxypropylcellulose, hydroxypropyl-methylcellulose, gum arabic, a polyacrylate, and an acrylic/maleic copolymers and combinations thereof.

Emulsifiers that can be included in the compositions and formulations include, for example, ionic, non-ionic, zwitterionic and/or anionic surfactants. In some examples, the emulsifier is a surfactant that is anionic, such as sodium lauryl sulfate (USP) and its derivatives, alkyl sulfonate surfactants, a linear alkylbenzene sulfonic acid, a branched alkylbenzene sulfonic acid a $C_{12}$ to $C_{18}$ alkylsulfate, $C_{12}$-$C_{18}$ alkyl alkoxy sulfate, $C_{12}$-$C_{18}$ alkyl methyl ester sulfonate, fatty soaps, alkyl sulfates, sulfated oils, ether sulfates, sulfonates, sulfosuccinates, sulfonated amides and isethionates; a zwitterionic surfactant; cationic surfactant, such as an alkylamine, an alkyl diamine, an alkyl polyamine, a mono- or di-quaternary ammonium salt, a monoalkoxylated amine, a dialkoxylated amine, a monoalkoxylated quaternary ammonium salt, a dialkoxylated quaternary ammonium salt, an etheramine, an amine oxide, an alkoxylated amine oxide and a fatty imidazoline, quaternary ammonium halides (such as cetyl pyridinium chloride); or a non-ionic surfactant, such as linear fatty alcohol ethoxylates or their polyoxyethylene condensation products (such as Spans and Tweens), alkyl arylpolyglycol ethers, polyethylene oxide esters of fatty acids, polyglycerol esters of fatty acids, polyoxyethylene sorbitan monolaurate, polyoxyethylene sorbitan mono- or tri-stearate, polyoxyethylene sorbitan monooleate, propylene glycol mono and diesters of fats and fatty acids, aryl sulfonates, sorbitan monostearate, poloxamer and its derivatives, medium chain triglyceride, caprylocaproyl macrogolglycerides, diethyleneglycol monoethyl ether, PEG-6 olive oil, PEG-6 peanut oil, PEG-6 hydrogenated palm kernel oil, propylene glycol dicaprylate/dicaprate, polysorbate, sorbitan esters, polyethoxylated castor oil, PEG-60 hydrogenated castor oil, PEG-40 hydrogenated castor oil, sodium lauryl glutamate, disodium cocoamphodiacetate, Polyoxyl 23 lauryl ester, an alkoxylated alcohol, a dialkoxylated alcohol, an alkoxylated dialkylphenol, an alkylpolyglycoside, an alkoxylated alkylphenol, an alkoxylated glycol, an alkoxylated mercaptan, an alkylamine salt, an alkyl quaternary amine salt, a glyceryl or polyglyceryl ester of a natural fatty acid, an alkoxylated glycol ester, an alkoxylated fatty acid, an alkoxylated alkanolamide, a polyalkoxylated silicone and an N-alkyl pyrrolidone, and combinations thereof.

c. Viscosity Modulating Agents

In some applications, the compositions and formulations provided herein can include a viscosity modulating agent. Viscosity modulating agents, such as polymers and thickeners, can be included in the compositions and/or formulation for any number of reasons. A viscosity modulating agent can help to stabilize a composition or formulation during shipping and storage by preventing separation of the composition, or be slowing or preventing coalescence of dispersed particle or oil droplets. A viscosity modulating agent can help to stabilize an emulsion or as an auxiliary to form or stabilize a foam. A viscosity modulating agent also can modify the rheology of the composition and/or formulation, thereby facilitating application to a targeted locus. For example, a viscosity modulating agent can be selected such that the composition and/or formulation, when dispensed from a spraying device, produces even or uniform droplets with little overspray. In applications where the composition and/or formulation is to be applied to a locus by brushing or dipping, a viscosity modulating agent can be selected so that the composition adheres to the surface of the locus and coats the surface. The viscosity modulating agent also can modify the release profile of the composition and thereby slow the release of the solavetivone, 5-epi-β-vetivone or derivatives or analogs thereof from the compositions and/or formulations.

Any viscosity modulating agent known in the art can be selected, based on the properties desired in the final compositions and formulations. Some polymers have an intrinsic viscosity that they impart to a composition or formulation based on the concentration of the viscosity modulating agent included in the composition or formulation. Lower molecular weight polymers generally tend to have lower viscosity contributing ability at lower concentrations, meaning that a higher percentage of viscosity modulating agent is required to achieve a higher viscosity in the final composition or formulation. The skilled artisan can select the type of viscosity modulating agent, its molecular weight and the percentage to include in the composition based on the chemistry and rheology of the viscosity modulating agent. For example, at or about 20% or more gum arabic or similar compound can be used to provide film forming and viscosity modifying effects, while as little as 0.2% xanthan gum can provide similar viscosities and stabilizing effects.

Exemplary viscosity modulating agents that can be included in the compositions and formulations provided herein include, but are not limited to, an acrylate, an acrylate copolymer, an alginate, an arabino-galactan, a carrageenan, a cellulosic polymer, such as bacterial cellulose, carboxymethyl cellulose, ethyl cellulose, ethyl-hydroxyethylcellulose, hydroxyethyl cellulose, hydroxypropyl cellulose, hydroxypropyl methylcellulose, methyl cellulose, microparticulate cellulose and sodium carboxymethyl cellulose and combinations thereof, a ceramide, chitan, dextran, diutan, fucelleran, fucoidan, a β-glucan, a gellan gum (native or low acetate), guar gum, gum arabic, gum ghatti, gum tragacanth, karaya gum, laminaran, locust bean gum, a methacrylate, a methyl methacrylate, modified starch, pectin, propylene glycol alginate, psyllium gum, polyvinyl pyrrolidone, rhamsan gum, scleroglucan (including clarified scleroglucan), starch, starch hydroxyethyl ether, starch dextrins and a xanthan gum, such as a clarified or low acetate or high pyruvate xanthan gum, and combinations thereof.

The amount of viscosity modulating agent included in the compositions or formulations can be selected based on the desired viscosity of the compositions or formulations. For example, a free flowing composition or formulation can require very low amounts of viscosity modulating agents, while a composition or formulation in the form of a non-flowing viscous gel can require significantly higher amounts of viscosity modulating agents. Generally, the viscosity modulating agent can be included in an amount of between at or about 0.05% and at or about 25%, or between at or about 0.1% and at or about 10%, or between at or about 0.5% and at or about 5%, by weight, of the composition.

Under some circumstances or conditions of use, it can be desirable to reduce the rate of evaporation of solavetivone, 5-epi-β-vetivone or derivatives or analogs thereof. Any one of a number of different strategies can be used to reduce the evaporation rate of solavetivone, 5-epi-β-vetivone or derivatives or analogs thereof if so desired. As discussed above, the provided solavetivone or 5-epi-β-vetivone compositions can include a viscosity modulating agent to thicken the composition, thereby requiring the solavetivone or 5-epi-β-vetivone to migrate through the composition to the surface and then through the surface before it can evaporate. In another example, the compositions can be prepared in the form of an emulsion, either an oil-in-water emulsion or water-in-oil emulsion. Interactions of the solavetivone, 5-epi-β-vetivone or derivatives or analogs thereof with surfactants in the emulsions or physical separation of the oil particles can result in a slower release of the solavetivone, 5-epi-β-vetivone or derivatives or analogs thereof from the composition as compared to a composition in the form of a liquid. Alternatively, an adhesive agent can be used to assist in adhering the compositions containing solavetivone, 5-epi-β-vetivone or derivatives or analogs thereof to the surface of a solid carrier. Interactions of the solavetivone, 5-epi-β-vetivone or derivatives or analogs thereof with the adhesive agent can result in a slower release of the solavetivone, 5-epi-β-vetivone or derivatives or analogs thereof from the composition as compared to a composition without any adhesive agents. Any adhesive agent known in the art can be used to assist in adhering the composition or formulation to the surface of a solid carrier, including, but not limited to, for example, waxes, film-former and other polymers, such as alginate, carboxymethyl cellulose, gum arabic, shellac, methyl cellulose, pectin, polyvinyl alcohol, propylene glycol, rhamsan gum, welan gum and xanthan gum.

d. Preservatives

In some applications, the compositions and formulations provided herein can include a preservative. Any preservative known in the art can be included in the compositions. Exemplary preservatives for use in the provided compositions and formulations include, but are not limited to, azoles, benzisothiazolin-3-one, benzalkonium quaternary compounds, benzyl alcohol, borates, 2-bromo-2-nitro-propane-1,3-diol, butylparaben, 5-chloro-2-methyl-4-isothiazolin-3-one, chlorphenesin, chloroxylenol, diazolidinyl urea, a dimethyl-benzylalkyl-ammonium chloride, ethylparaben, formaldehyde, glutaraldehyde, halogenated salicylanilides, hexachlorophene, hexylene glycol, isobutylparaben, isothiazolin-3-one, 2-methyl-4-isothiazoline-3-one, methylchloroisothiazolinone, methylisothiazolinone, methylparaben, monochloracetamide, neomycin sulfate, o-phenylphenol and salts thereof, phenoxyethanol, propionic acid and salts thereof, propylparaben, sodium benzoate, sorbic acid and salts thereof, tebuconazole and triazoles, and combinations thereof. Some preservatives are more potent or effective than others, as is known in the art. When in the compositions or formulations, the preservative can be included in an amount of between at or about 0.001% to at or about 5%, by weight, of the composition. For example, the preservative can be included in the compositions or formulations in an amount between at or about 0.005% to at or about 2.5%, by weight, of the composition or in an amount between at or about 0.01% to at or about 1%, by weight, of the composition.

e. Colorant

In some applications, the compositions or formulations provided herein can include a colorant. The colorant can provide additional visual cues to the applier of the compositions or formulations, such as to help the applier see where the compositions or formulations are being applied to a surface or locus and thereby identifying a coverage are and/or allowing an even distribution of the compositions or formulations on a surface. Any colorant known in the art can be included in the compositions provided herein. Exemplary colorants for use in the provided compositions and formulations include, but are not limited to, dyes and pigments, such as titanium oxide, titanium dioxide, zinc oxide, white lead, zinc sulfide, aluminum oxide, iron oxide, silicon oxide, zirconium oxide, an azo-type colorant, a condensate-type colorant, a phthalocyanine-type colorant, a quinacridone-type colorant, an insoluble lake pigment, organic dyes, such as alizarin dyes, azo dyes or metal phthalocyanine dyes.

When present in the compositions or formulations, the colorant can be included at any concentration necessary to impart the desired or targeted color to the composition. In general, the colorant can be included in an amount of between at or at least about 0.0001% to at or about 1%, by weight, of the composition. In some applications, the colorant is included in an amount between at or about 0.0005% to at or about 0.5%, by weight, of the composition.

f. Synergists

In some examples, the provided compositions contain synergists that act to increase or prolong the effects of the compositions without increasing the amount of active ingredient. Examples of suitable synergists for use in the compositions include, but are not limited to, bis-(2,3,3,3-tetrachloropropyl)ether, dodecyl imidazole, N-(2-ethylhexyl) bicyclo-[2,2,1]hept-5-ene-2,3-dicarboxyimide piperonyl butoxide, isobornyl thiocyanatoacetate, safroxan and sesame, or combinations thereof. In general, the synergist can be included in an amount of between at or at least about 0.1% to at or about 99%, or between at or at least about 3% to at or about 97%, or between at or at least about 10% to at or about 90%, at or at least about 1% to at or about 50%, by weight, of the composition.

3. Microencapsulation

In some examples, the compositions or formulations provided herein include an encapsulated or microencapsulated active ingredient, such as an encapsulated or microencapsulated solavetivone, 5-epi-β-vetivone or derivatives or analogs, thereby altering the release of the active ingredient from the composition. Microencapsulation is well known in the art and is used to control the release rates of many essential oils, such as in fabric softener and deodorant formulations. For example, release of the active ingredient can be modulated or controlled by, for example, surrounding the active ingredient, such as solavetivone, 5-epi-β-vetivone or derivatives or analogs thereof; in a film-forming material to form micron or sub-micron capsules containing the solavetivone, 5-epi-β-vetivone or derivatives or analogs thereof. After contact with a substrate, such as human skin or a targeted locus, the capsules begin to break down and release the encapsulated solavetivone, 5-epi-β-vetivone or derivatives or analogs thereof. The process can continue as new intact microcapsules are broken down to release a new amount of solavetivone, 5-epi-β-vetivone or derivatives or analogs thereof, replenishing the solavetivone, 5-epi-β-vetivone or derivative or analog thereof that may have been displaced or evaporated from the vicinity of application.

Microencapsulation is well known in the art and encapsulation can be accomplished using any known method. Microcapsules can be prepared using a range of conventional methods known to those skilled in the art for making shell capsules, such as interfacial polymerization and polycondensation. See, e.g., MICROENCAPSULATION: Methods and Industrial Applications (Benita and Simon, eds., Marcel Dekker, Inc. 1996); Lee et al. (2002) *J. Microencapsulation* 19(5):559-569; U.S. Pat. Nos. 3,516,941, 4,520,142, 4,528,226, 4,681,806, 4,145,184 and 7,838,037; GB Patent No. 2,073,132; and International Patent Pub. No. WO 99/17871. It is recognized, however, that many variations with regard to materials and process steps are possible. Non-limiting examples of materials suitable for making the shell of the microcapsule include urea-formaldehyde, melamine-formaldehyde, phenol-formaldehyde, alginate, gelatin, gelatin/gum arabic blend, gellan gum, polyurethane and polyamides, or combinations thereof.

The microcapsules can be of any desired size, and the dimensions of the particles can be selected depending on the final use of the composition. For example, the microcapsules can have a mean diameter in the range from at or about at least 1 micron to at or about 100 microns, for example, from at or about 5 microns to at or about 80 microns, from at or about 10 microns to at or about 75 microns, or from at or about 15 microns to about 50 microns. The particle size distribution can be narrow, broad or multimodal. The average shell thickness can vary, and can be from at or about 0.02 microns to at or about 5 microns, for example, from at or about 0.02 micron to at or about 1 micron.

G. FORMULATIONS CONTAINING SOLAVETIVONE, 5-EPI-B-VETIVONE AND/OR DERIVATIVES OR ANALOGS THEREOF

The provided compositions containing a solavetivone, 5-epi-β-vetivone or derivative or analog thereof and a carrier can be formulated as a lotion, gel, cream, aerosol or spray, or can be included on a silacaceous clay, talc or granule, or in woven or nonwoven substrates. For example, the provided compositions can be formulated into a variety of personal, household and home care formulations, such as for application to animals, including humans, domesticated animals and pets, bedding, clothing, carpeting and wooden structures. Such formulations include but are not limited to, sprays, dusts and granules, woven or nonwoven substrates, aerosols, personal care and cosmetic formulations, insect repellants, insecticides and pesticides, and household care formulations.

The carrier and additional components/ingredients of each composition can be modified to suit each particular formulation or purpose. For example, formulations designed for controlling drain flies can be formulated to contain surfactants and/or viscosity modifying agents so that the composition can be dispensed into a drain pipe, clinging to the pipe walls as it flows, thereby killing any adult or immature drain flies with which it comes into contact, and for providing an extended release of the composition for residual killing and repelling effects.

1. Sprays

The compositions provided herein containing a solavetivone, 5-epi-β-vetivone or derivative or analog thereof can contain a liquid carrier and be formulated for delivery using a pump spray. In some applications, the composition includes a carrier containing an alcohol, ether, ester, ketone, aldehyde, oil or water or combinations thereof to provide a solution of low viscosity that can be dispensed using a pump spray. For example, a composition containing from at or about or at least about 0.1% to at or about 10%, or greater than 10%, or greater than 15%, or greater than 20% active ingredient, e.g., solavetivone, 5-epi-β-vetivone or derivative or analog thereof, and from at or about 50% to at or about 99.9% carrier, such as an alcohol, ether, ester, ketone, aldehyde, oil or water or combinations thereof, by weight, of the composition can be used as a spray for topical application to surfaces, such as bedding, clothing and carpeting.

In some examples, other carriers can be included in the composition. For example, an exemplary composition contains from at or about 0.1% to at or about 10%, or greater than 10% solavetivone, 5-epi-β-vetivone or derivative or analog thereof, by weight, of the composition, and the balance of the composition contains a carrier selected from among water, an alcohol, an aldehyde, an alkane, an alkene, an amide, an amine, a diglyceride, an ester, an ether, a glycol ether, a fat, a fatty acid, a glycol ester, a ketone, lanolin, mineral oil, a silicone or silicone oil, paraffin oil, a monoglyceride, a polyethylene glycol, petrolatum, a propylene carbonate, tall oils, a terpene hydrocarbon, a terpene alcohol, a triglyceride, finely divided organic solid material, finely divided inorganic solid materials and mixtures thereof.

The sprays can be formulated to include viscosity modifiers so that the composition adheres to the target location or the targeted insect and/or pest. The composition also can include a penetration agent when the spray is intended for application directly onto the insect or pest, such as for sprays directed to controlling ants, ticks, fleas, roaches, wasps, hornets, bed bugs or mites. Penetration agents are known to one of skill in the art. Any penetration agents known in the art can be included. Exemplary penetration agents include, but are not limited to, silicone dioxide, petroleum distillate, light solvent naphtha and D-limonene, or combinations thereof. In general, the penetration agent can be included in an amount of between at or at least about 0.001% to at or about 50%, such as at or at least about 0.1% to at or about 50%, or at or at least about 1% to at or about 10%, by weight, of the composition.

2. Dusts and Granules

The compositions provided herein can contain a solid carrier and be formulated as dusts or granules. Compositions including a solid carrier can be used when application to large area is desired, or when application in a dry form is desired or required. Solid carrier compositions are free-flowing and can be applied by methods known in the art, including spraying and spreading. Exemplary solid carrier compositions can include solavetivone, 5-epi-β-vetivone or derivative or analog thereof applied directly to the surface of the solid carrier, or by making a pre-blend of the active ingredient in a liquid carrier and coating the solid carrier with the active ingredient pre-blend using any method known in the art, such as blending, mixing, or using a coating apparatus (see U.S. Pat. Nos. 5,043,090 and 5,413,795). The solid carrier can be less that 50 microns and in the form of a dust or powder, or can be larger, in the form of granules. The granules can be porous or non-porous. Generally, any amount of solavetivone, 5-epi-β-vetivone or derivative or analog thereof can be adsorbed onto and/or into the granules. For example, formulations containing from at least or about at least 0.1% to at or about 10%, or greater than 10%, or greater than 15%, or greater than 20% or greater than 25% solavetivone, 5-epi-β-vetivone or derivative or analog thereof, by weight, of the composition can be prepared. An exemplary composition contains 15% solavetivone, 5-epi-β-vetivone or derivative or analog thereof and 85% preformed granular attapulgite. The dusts or granules can be dispensed in areas infested with an insect or pest, or in areas suspected of harboring the insect or pest. For example, dusts or granules can be sprinkled over ant trails or under kitchen sinks where roaches had been observed. The dusts or granules attach to the pest or insect when it comes into contact with the dust or granule. The dusts can include waxes or viscosity modifying agents in order to increase the adhesion of the particles to the pest or insect.

3. Woven or Nonwoven Substrates

The compositions provided herein also can be deployed on a solid surface other than a dust or granule. For example, the compositions containing a solavetivone, 5-epi-β-vetivone or derivative or analog thereof provided herein can be used to coat an absorbent or non-absorbent cellulosic, woven or non-woven fabric. Exemplary of such formulations are fabric softener dryer sheets, which are well known in the art (see, e.g., U.S. Pat. Nos. 6,574,883, 6,875,732, 6,930,082, and 7,989,413). Non-woven material typically can be formed of natural fibers such as cellulosic, plant-based, polylactic acid material, or synthetic fibers such as polyester, nylon, polypropylene, polytrimethylene terephthalate and polyethylene terephthalate, or, blends of such natural and synthetic fibers. The fibers can be formed in a sheet, typically by hydro-entanglement or needle-entanglement. In some examples, the woven or nonwoven sheet is a fabric treatment sheet.

The compositions containing solavetivone, 5-epi-β-vetivone or derivative or analog thereof when applied to an absorbent or non-absorbent cellulosic, woven or non-woven fabric can be used in the dryer to deliver the solavetivone, 5-epi-β-vetivone or derivative or analog thereof to clothing and bedding. The treated sheets also can be used to topically apply the compositions provided herein containing solavetivone, 5-epi-β-vetivone or derivative or analog thereof to a surface by wiping the surface with the treated sheet. For example, the surface can be skin, hair or fur of an animal, or can be a hard surface, such as a counter, floor, baseboard or headboard. In some examples, the formulation is a moist towelette. In such formulations, the composition can include surfactants. The treated sheets also can be used to directly dispense the solavetivone, 5-epi-β-vetivone or derivative or analog thereof to a locus, by placing the sheet containing the solavetivone, 5-epi-β-vetivone or derivative or analog thereof composition in the locus. The amount of solavetivone, 5-epi-β-vetivone or derivative or analog thereof applied to or contained on or within the treated absorbent or non-absorbent cellulosic, woven or non-woven fabric can be between at least or at least about 0.1% to at or about 10%, or greater than 10%, or greater than 15%, or greater than 20%, or greater than 25% based on the total weight of the treated fabric.

4. Aerosols

The compositions provided herein can contain a gas carrier, such as a gas propellant, and be formulated for use in aerosol devices. Aerosol devices are known in the art (see, e.g., U.S. Pat. Nos. 3,915,343, 3,884,828, 3,970,584, 4,062,937 and 6,415,992). Most aerosol products contain the active ingredient, e.g., solavetivone, 5-epi-β-vetivone or derivative or analog thereof, and the propellant. Examples of suitable gas propellants include propane, n-butane, isobutane, ethylene, dimethyl ether, nitrogen, nitrous oxide and carbon dioxide, and mixtures thereof. In one example, a composition contains at least or at least about 0.1% to at or about 10%, or greater than 10%, or greater than 15%, or greater than 20% solavetivone, 5-epi-β-vetivone or derivative or analog thereof, by weight, of the composition, optionally at or about 10% to at or about 20% carrier, such as an alcohol, ester, ether, aldehyde or ketone, and the balance gas propellant.

5. Personal Care and Cosmetic Formulations

The compositions provided herein also can be included in a personal care or cosmetic composition. For example, a composition containing a mixture of solavetivone and 5-epi-β-vetivone or derivative or analog of one or both, such as at a ratio of at least or as most as any of 25:1, 20:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8. 1:9, 1:10, 1:11, 1:12, 1:13, 1:14, 1:15, 1:20 or 1:25 mixture of solavetivone, 5-epi-β-vetivone or derivative or analog thereof to a carrier, such as an alcohol, aldehyde, ketone, ester, oil or ether, or combinations thereof, can be prepared and added to a standard personal care or cosmetic formulation to deliver the solavetivone, 5-epi-β-vetivone or derivative or analog thereof. Representative formulations to which the solavetivone, 5-epi-β-vetivone or derivative or analog thereof can be added include insect repellents, skin care products, hair care products, and cleansing products. Exemplary skin care products include, but are not limited to, skin conditioners, hand/body/facial lotions, skin moisturizers, skin toners, skin sanitizers, skin cleansing compositions, skin soothing and lubricating compositions, sunscreen products, anti-aging products, tanning products, self-tanning products, after-sun products, masking products and anti-wrinkle products. Exemplary hair care products include, but are not limited to, hair conditioners, hair styling gels, hair anti-dandruff compositions, hair growth promoter compositions, hair lotions, hair tonics, rinses, conditioners, hair colorant compositions, hair anti-frizzing agent compositions, hair shining compositions, mousses, styling gels, hair pomade products and hair sprays. Exemplary cleansing products include, but are not limited to, soaps, foaming bath products, hand/body/facial cleansers, astringent cleansers, anti-acne products, body shampoos, synthetic detergent bars, shower gels and shampoos. For example, a shampoo can be prepared using 80% Just the Basics Shampoo (which contains water, sodium laureth sulfate, cocamide MEA, cocamidopropyl betaine, glycerin, tocopheryl acetate, panthenol, sodium methyl cocoyl taurate, PEG-7 glyceryl cocoate, polyquaternium-10, PPG-12-buteth-16, polyquaternium-7, citric acid, sodium chloride, methylchloroisothiazolinone, methylisothiazolinone, disodium EDTA, tetrasodium EDTA, and fragrance), 10% solavetivone, 5-epi-β-vetivone or derivative or analog thereof, 5% ethyl alcohol and 5% isopropyl alcohol. A similar shampoo can be prepared using 80% Just the Basics Shampoo, 15% solavetivone, 5-epi-β-vetivone or derivative or analog thereof and 5% acetone. Another similar shampoo can be prepared using 75% Just the Basics Shampoo, 20% solavetivone, 5-epi-β-vetivone or derivative or analog thereof and 5% acetone.

The compositions provided herein containing a solavetivone, 5-epi-β-vetivone or derivative or analog thereof can be formulated as a topical formulations for applying to a surface, including skin or hair. The formulation can be provided in any form suitable for topical application, such as an emulsion, a solution or suspension. Exemplary formulation forms include, but are not limited to, aerosols, creams, emulsions, foams, gels, lotions, ointments, pastes, solutions, sprays, suspensions, or any other formulations suitable for topical administration, or combinations thereof. Formulation of personal care products for topical application is well known in the art (see U.S. Pat. No. 5,472,686; and Flick, "Cosmetic and Toiletry Formulations Volume 8 (Cosmetic & Toiletry Formulations)," Noyes Publications (2001)).

An effective amount of solavetivone, 5-epi-β-vetivone or derivative or analog thereof to include in a topical personal care formulation for killing or repelling pests, including insects, can be in the range of at least or at least about 0.1% to at or about 10 or greater than 10%, or greater than 15%, or greater than 20%, or greater than 25%, or greater than 50%, by weight, of the personal care formulation.

6. Pest and Insect Repellents

The compositions provided herein containing solavetivone, 5-epi-β-vetivone or derivative or analog thereof can be pest repellent, e.g., insect repellant, formulations that contain the active ingredient in the range of at least or at least about 0.1% to at or about 10%, or greater than 10%, or greater than 15%, or greater than 20%, or greater than 25%, or greater than 50%, by weight, of the insect or pest repellant formulation. For example, a pest repellant formulation can contain at least or at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%, by weight, of the pest repellant formulation. In some examples, the insect and pest repellent formulations contain the active ingredient in the range of at least or at least about 0.5%, by weight, of the composition, such as at least or at least about 0.5% to at or about 10%, or greater, by weight, of the composition. The formulation can be provided as a liquid, aerosol, cream, gel, lotion, oil, spray, soap, detergent, particulate or a substrate, such as a saturated woven or nonwoven cloth or infused plastic or absorbent plastic polymer, such as is often used for a pet collar. An exemplary formulation contains 0.5% solavetivone, 0.1% butylated hydroxytoluene (BHT) and 99.4% acetone. Another exemplary formulation contains 0.5% 5-epi-β-vetivone, 0.1% butylated hydroxytoluene (BHT) and 99.4% acetone.

In some applications, the solavetivone, 5-epi-β-vetivone or derivative or analog thereof can be mixed with a carrier prior to incorporating the composition into the formulation or onto or into a woven or nonwoven substrate. The ratio of solavetivone, 5-epi-β-vetivone or derivative or analog thereof to carrier can vary, between, for example, at a ratio of at least or as most as any of 25:1 to 1:25, such as 25:1, 20:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8. 1:9, 1:10, 1:11, 1:12, 1:13, 1:14, 1:15, 1:20 or 1:25 or ranges between such ratios. When present, a nonwoven substrate can be a flexible sheet that includes fibers, which can be adhesively or thermally bonded. The fibers can be of any material, such as cellulose, cellulose ester, cotton, hemp, jute, linen, ramie, rayon, polyamides, polyesters polyolefins, polypropylene, polyvinyl derivatives, silk, sisal and wool and combinations thereof.

In some applications, the pest repellent composition includes a viscous or solid gel that can be used for topical application (such as in the form of a stick or paste) or for release of the solavetivone, 5-epi-β-vetivone or derivative or analog thereof into a targeted locus. The viscous fluid or gel can be made by, e.g., incorporating a gelling agent, such as an agar, carbomer, carboxyvinyl polymers, dibenzylidene alditols, carboxypoly-methylene, collagen, dextrin fatty acid esters, gelatin, hydrogenated styrene/isoprene copolymers, 12-hydroxystearic acid, κ-carrageenan, gellan gum, a lower hydroxy cellulose, pectin, polyacrylic acids, styrene-ethylene/propylene block copolymers, styrene-ethylene/butylene-styrene block copolymers, sucrose fatty acid esters or wax, such as candelilla wax, carnauba wax, ceresin wax, microcrystalline wax paraffin wax and polyethylene wax, or combinations thereof, into a solvent, such as water, an alcohol, a ketone, an ester, an ether or an oil. Typically, a gelling agent is included in a formulation or composition in an amount between at least or at least about 0.01% and at or about 10%, between at or about 0.05% and at or about 7.5%, between at or about 0.1% and at or about 5%, between at or about 0.2% and at or about 5%, or between at or about 0.25% and at or about 2.5%, by weight, of the composition. In one example, a composition contains 2% carrageenan, 15% solavetivone, 5-epi-β-vetivone or derivative or analog thereof, 5% acetone, 0.5% propylparaben, 0.5% potassium chloride and 77% water.

In some applications, the formulation can be prepared so that it forms a gel in situ. For example, sodium alginate can be used as a gelling agent and concurrent with or after application of the formulation, a solution of calcium chloride can be applied to the alginate-containing formulation, which will convert the sodium alginate into calcium alginate and thereby gel the formulation. Gelling agents that can exhibit delayed gelation are known in the art, including, but not limited to, agar, an alginate, a carbomer, carboxyvinyl polymers, dibenzylidene alditols, carboxypolymethylene, collagen, dextrin fatty acid esters, gelatin, hydrogenated styrene/isoprene copolymers, 12-hydroxystearic acid, κ-carrageenan, gellan gum, a lower hydroxy cellulose, pectin, polyacrylic acids, styrene-ethylene/propylene block copolymers, styrene-ethylene/butylene-styrene block copolymers, sucrose fatty acid esters and a wax and combinations thereof. Typically, a fluid that when dispensed forms a gel in situ is included in a formulation or composition in an amount between at least or at least about 0.01% and at or about 10%, between at or about 0.05% and at or about 7.5%, between at or about 0.1% and at or about 5%, between at or about 0.2% and at or about 5%, or between at or about 0.25% and at or about 2.5%, by weight, of the composition.

The pest repellent also can be provided as a particulate or powder. In such formulations, a portion or all of the carrier is a finely divided solid, such as an alumina, amorphous silica, attapulgite, calcium carbonate, calcium phosphate, clay, chalk, diatomaceous earths, fumed silica, a kaolin, kieselguhr, magnesium carbonate, microparticulate cellulose, montmorillonite, pyrophyllite, silicic acid, sodium bicarbonate, sodium carbonate, sodium phosphate, sodium pyrophosphate, talc, and vermiculite, and combinations thereof. These formulations can be applied by spraying, sprinkling or dusting.

The pest repellent also can be provided as an aerosol propellant pressurized spray. In such formulations, a propellant is included in an amount between at least or about at least 5% to at least or about at least 75%, by weight, of the composition. Propellants include, for example, carbon dioxide, propane, butane or a mixtures thereof.

The pest repellent, e.g., insect repellent, formulation provided herein also can include, in addition to the solavetivone, 5-epi-β-vetivone or derivative or analog thereof, an additional compound that repels insects. Examples of active compounds that repel insects are N,N-diethyl-meta-toluamide (DEET), picaridin (2-(2-hydroxyethyl)-1-piperidinecarboxylic acid 1-methylpropyl ester), citronella oil, camphor oil, cedarwood oil, coumarin, 2-hydroxymethylcyclohexyl acetic acid lactone, beta-alanine, 2-hydroxymethyl-cyclohexylidene acetic acid lactone, 2-hydroxy-methylcyclohexyl propionic acid lactone, p-menthane-3,8-diol, and 3-[N-butyl-N-acetyl]-aminopropionic acid ethyl ester, and combinations thereof. The additional compound can be included in an amount of from at least or at least about 0.1% to at or about 25%, by weight, of the composition. In some applications, the active ingredient is DEET at a concentration of from at or about 2.5% to at or about 25%, by weight, of the composition. Other compositions including DEET can have varying amount of DEET, such as DEET at a concentration of from at or about 2.5% to at or about 5%, or from at or about 5% to at or about 15%, or from at or about 10% to at or about 20%, by weight, of the composition.

The pest repellent can be provided as a packaged product. For example, the package can include a container holding any of the compositions provided herein containing solavetivone, 5-epi-β-vetivone or derivative or analog thereof, or an absorbent sheet impregnated a composition provided herein. The pest repellent can be provided as an aerosol propellant pressurized spray, which contains any one of the compositions provided herein and at least at or about 5% to 90% propellant, by weight, of the composition. Any propellant commonly used in the art for preparation or aerosol sprays can be included in the compositions. For example, the propellant can include carbon dioxide, nitrous oxide, propane or butane, or a mixture thereof.

7. Pesticides or Insecticides

The compositions provided herein containing a solavetivone, 5-epi-β-vetivone or derivative or analog thereof can be formulated as a pesticide, e.g., insecticide, for administration directly to a surface of a pest, e.g., insect. The pesticide formulations generally are formulated so that they have sufficient viscosity to adhere to the insect or pest or to include ingredients that can assist the formulation in penetrating the exoskeleton of the insect or pest. In such formulations, an amount of a composition provided herein is included to provide an amount of solavetivone, 5-epi-β-vetivone or derivative or analog thereof is of at least or at least about 1% to at or about 10%, or greater than 15%, or greater than 20%, or greater than 25%, or greater than 50%, by weight, of the composition. For example, a pesticide can contain at least or at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9% or 100%, by weight, of the pesticide formulation. The carrier can be a liquid or a solid. For example, when a solid particulate is selected, the carrier can include an alumina, amorphous silica, attapulgite, calcium carbonate, calcium phosphate, a clay, chalk, diatomaceous earths, fumed silica, a kaolin, kieselguhr, magnesium carbonate, microparticulate cellulose, montmorillonite, pyrophyllite, silicic acid, sodium bicarbonate, sodium carbonate, sodium phosphate, sodium pyrophosphate, talc, or vermiculite, or any combination thereof. In some examples, such carriers assist the insecticide or pesticide to adhere to the insect or pest.

The pesticide formulation also can be designed to include an adhesion agent so that it forms a viscous fluid or gel when dispensed onto the insect or pest. For example, the carrier of the composition provided herein can contain an adhesion agent that includes between at or about 0.2% to at or about 5% gelling agent, such as agar, an alginate, a carbomer, carboxyvinyl polymers, dibenzylidene alditols, carboxypolymethylene, collagen, dextrin fatty acid esters, gelatin, hydrogenated styrene/isoprene copolymers, 12-hydroxystearic acid, κ-carrageenan, gellan gum, a lower hydroxy cellulose, pectin, polyacrylic acids, styrene-ethylene/propylene block copolymers, styrene-ethylene/butylene-styrene block copolymers, sucrose fatty acid esters and a wax, or combinations thereof. The adhesion agent can include at or about 0.2% to at or about 20% of a viscosity modulating agent described in Section E.2.c above. In some applications, the compositions can include penetration agents that help to penetrate the exoskeleton of the insect or pest. Exemplary penetration agents include, but are not limited to, silicone dioxide, petroleum distillate, light solvent naphtha or D-limonene, or combinations thereof. Silicone dioxide causes small abrasions on the body of any insect or pest that comes into contact with the powder, thus allowing the compositions to penetrate the exoskeleton. Petroleum distillate, light solvent naphtha and D-limonene are solvents that can help dissolve any wax or cuticle on the exoskeleton, thereby allowing better adhesion of an aqueous-based formulation as well as better penetration through the exoskeleton. In general, the penetration agent can be included in an amount of between at or at least about 0.001% to at or about 50%, by weight, of the composition.

An insecticide or pesticide formulation also can be provided as an aerosol propellant pressurized spray. In such formulations, a propellant is included in an amount between at least or about at least 5% to at least or about at least 75%, by weight, of the composition. Propellants include, for example, carbon dioxide, propane, butane or a mixtures thereof.

8. Household Care Formulations

The compositions provided herein containing a solavetivone, 5-epi-β-vetivone or derivative or analog thereof can be formulated as a household care composition. For example, a composition containing a mixture of a carrier and solavetivone, 5-epi-β-vetivone or derivative or analog thereof, at a ratio of solavetivone, 5-epi-β-vetivone or derivative or analog thereof to carrier of a ratio of at least or as most as any of 25:1, 20:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8. 1:9, 1:10, 1:11, 1:12, 1:13, 1:14, 1:15, 1:20 or 1:25, can be prepared and added to a household care composition. The carrier can be a liquid or a solid, such as any described in Section E.1. above. In some examples of the household care products including a composition containing solavetivone, 5-epi-β-vetivone or derivative or analog thereof provided herein, the final amount of solavetivone, 5-epi-β-vetivone or derivative or analog thereof in the product is at least or about at least 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95% or 100%, by weight, solavetivone, 5-epi-β-vetivone or derivative or analog thereof.

Exemplary household care products include air deodorant/freshener compositions in liquid, gel or solid form, all purpose cleaner compositions, all purpose disinfectant compositions, deodorizing sprays and powders, dish detergents, fabric sizing compositions, fabric softening compositions, fabric static control compositions, hard surface cleanser compositions, hard surface detergents, hard surface sanitizing compositions, linen and bedding spray compositions, pesticide compositions, polishing compositions, laundry detergents, rug and upholstery shampoo compositions, cleaners and deodorizers, tile, toilet and tub cleaning and disinfectant compositions, waxes and cleaning compositions for treating wood floors or furniture, and waxes and cleaning compositions for automobiles. The formulations can be in any form, such as an aerosol, a bar, a cream, a gel, a liquid, a lotion, a paste, a powder, a roll-on, a sheet, a spray, a stick and a tablet form.

Particular household care products into which the compositions provided herein containing solavetivone, 5-epi-β-vetivone or derivative or analog thereof can be included include laundry products, such as, but not limited to, cleansing compositions, such as laundry detergents and fabric softening compositions. Such laundry products are well known in the art (see, e.g., U.S. Pat. Nos. 2,954,347; 2,954,348; 3,707,503; 3,892,680; 3,929,663; 3,936,538; 4,009,114; 4,304,680; 4,566,980; 4,581,385; 5,425,891; 7,354,892; 7,387,992; 7,648,953; 7,863,236; 7,910,534; 7,910,538; 7,928,050; 7,951,768; and 7,994,112). The compositions provided herein containing solavetivone, 5-epi-β-vetivone or derivative or analog thereof can be included in such laundry product so that the final formulation contains from at least or at least about 0.1% to at or about 10%, or greater than 10%, or greater than 15%, or greater than 20%, or greater than 25%, or greater than 50% solavetivone, 5-epi-β-vetivone or derivative or analog thereof, by weight, of the composition, and a detergent component or a fabric softening active agent.

Also provided are fabric treatment sheets that contain a woven or nonwoven sheet coated or impregnated with a composition provided herein and additionally a detergent composition. Detergent compounds include, but are not limited to, anionic surfactants, nonionic surfactants, zwitterionic surfactants, ampholytic surfactants and cationic surfactants and mixtures thereof. Many laundry detergents are non-phosphated and can contain synthetic anionic surfactants, such as lauryl benzene sulfonic acid, alpha-olefin sulfonate, sodium lauryl sulfate, sodium lauryl ethoxylated sulfate, other alkyl benzene sulfonates, alcohol ether sulfates, and alcohol ethoxylates, polyacrylate and silicates. A detergent compound can be included in the compositions in an amount between at least or at least about 1% to at about 80%, by weight, of the composition. Cleansing compositions can additionally include a detergency builder that enhances the cleaning capacity or cleansing action of detergent compounds in a cleaning composition or improves detergency levels in detergent compositions and permits the attainment of cleaning performance that is superior to compositions that do not include a detergency builder. Detergency builders include, but are not limited to, alkali metal carbonates, alkali metal phosphates, alkali metal phosphonates, alkali metal polyphosphates, alkali metal polyphosphonic acids, alkali metal silicates, $C_8$-$C_{18}$ alkyl monocarboxylic acids, alkali metal, ammonium or substituted ammonium salts of polycarboxylic acids and a zeolite, and mixtures thereof.

Fabric softener formulations usually include one or more classes of softening or conditioning agents. Softening or conditioning agents are well known in the art (e.g., see U.S. Pat. Nos. 6,521,589 and 6,180,594), such as triethanolamine quaternary, diethanolamine quaternary, ACCOSOFT cationic surfactants (Stepan Chemical), or dimethyl ditallow ammonium chloride. One class of cationic softening or conditioning agents includes the quaternary amines (or "quats" or "quaternaries"). Exemplary quaternary amines that can be included in the formulations include, but are not limited to, monomethyl trialkyl quaternaries, imidazolinium quaternaries, dimethyl alkyl benzyl quaternaries, dialkyl dimethyl quaternaries, methyl dialkoxy alkyl quaternaries, diamido amine-based quaternaries and dialkyl methyl benzyl quaternaries or ($C_8$-$C_{24}$) fatty acid amides or any combination thereof. These materials function to condition the dried fabrics and to reduce static cling and lint adherence, as well as to improve sheen and/or hand-feel. The softening active agent can be included in an amount of from at least or at least about 1% to at or about 80%, by weight, of the product, or from at least or at least about 5% to at or about 40%, by weight, of the product, or from at or about 10% to at or about 30%, or from at or about 5% to at or about 15%, by weight, of the product. Also provided are fabric treatment sheets that contain a woven or nonwoven sheet coated or impregnated with a composition provided herein and additionally a fabric treatment composition that contains a softening or conditioning agent. Also provided are fabric treatment compositions containing a composition provided herein and a fabric softener or fabric conditioner.

The laundry products formulations provided herein can include other ingredients, such as an anti-static agent, a brightening agent, a bodying agent, a soil-release agent, a wrinkle-release agent or a combination thereof. Examples of anti-static agents include a tertiary amine, a quaternary amine or aluminum stearate, or a combination thereof. Examples of brightening agents include hydrogen peroxide, potassium permanganate, sodium peroxide, sodium perborate, disulfonated diaminostilbene optical brightener compounds and triazole optical brightener compounds. Examples of bodying agents include carboxymethyl cellulose, hydroxyethyl-cellulose, starch and polyvinyl acetate, and combinations thereof. An example of a soil-release agent is polyacrylic polyvinyl alcohol compositions (see, e.g., U.S. Pat. No. 3,377,249). An example of a wrinkle release agent is polyvinyl acetate. The compositions can be provided as liquids, gels or on a woven or nonwoven sheet, and can be formulated for use in the washer or dryer. Such sheets can contain detergent selected from among anionic surfactants, nonionic surfactants, zwitterionic surfactants, ampholytic surfactants and cationic surfactants and mixtures thereof, alone or in combination with a softening agent.

Another exemplary formulation is a fabric refresher spray composition, which can contain a concentration of solavetivone, 5-epi-β-vetivone or derivative or analog thereof of from at least or at least about 0.1% to at or about 10%, or greater than 10%, or greater than 15%, or greater than 20%, or greater than 25%, or greater than 50%, by weight, of the composition. An exemplary formulation contains 11% solavetivone, 5-epi-β-vetivone or derivative or analog thereof, 0.1% butylated hydroxytoluene (BHT) and 88.9% ethanol. The composition can be modified by reducing the amount of carrier, such as ethanol, to accommodate the addition of other ingredients. For example, the composition can include a carrier that is a cyclodextrin, such as alpha, beta, and gamma cyclodextrin, particularly beta-cyclodextrin. When sprayed on a fabric, the cyclodextrins can release an entrapped solavetivone, 5-epi-β-vetivone or derivative or analog thereof over time, thereby providing a delayed release of the solavetivone, 5-epi-β-vetivone or derivative or analog thereof. Surfactants, such as an ampholytic surfactant, an anionic surfactant, a cationic surfactant, a nonionic surfactant or a zwitterionic surfactant or a combination thereof, also can be included in the formulation, for example, to enhance the wettability of the composition.

Another exemplary formulation is a moist towelette product that contains a woven or nonwoven flexible substrate that has been treated with a composition provided herein, such that the towelette contains solavetivone, 5-epi-β-vetivone or derivative or analog thereof in an amount of from at least or at least about 0.1% to at or about 10%, or greater than 10%, or greater than 15%, or greater than 20%, or greater than 25%, or greater than 50%, by weight, of the composition. If formulated as a cleansing towelette, surfactants can be included in the composition. Generally, non-irritating surfactants are used, since the solution applied on the surface using the towelette can remain in place if is not immediately washed off. Exemplary non-irritating surfactants include cocamidopropyl betaine, coco-glucoside and decyl glucoside or combinations thereof.

H. PREPARATION OF COMPOSITIONS AND FORMULATIONS

The compositions provided herein containing solavetivone, 5-epi-β-vetivone or derivative or analog thereof can be produced using methods known to the skilled artisan. For example, in compositions in which all of the ingredient are liquids and have similar polarities such that when combined they readily form a solution or dispersion, the compositions can be prepared by mixing the components together, such as using a paddle mixer or lightning mixer.

In some applications, one or more of the components of the composition can be solid at room temperature but melts at elevated temperatures to form a liquid. In cases where one of the components needs to be heated in order to incorporate them into the composition, the ingredients to be heated generally can be segregated from the nootkatone or derivative or analog thereof, which is volatile. For example, an ingredient to be heated can be mixed in a jacketed vessel while heating until liquified, and then the carrier and any optional components can be incorporated with constant mixing. The temperature of the resulting mixture then can be reduced to room temperature or slightly higher (such as 25° C.) and the solavetivone, 5-epi-β-vetivone or derivative or analog thereof added with constant mixing until incorporated.

In some applications, the compositions are provided as a water-in-oil emulsion or an oil-in-water emulsion. Machines and apparatuses for making emulsions are known in the art. Examples of such equipment include colloid mills, sprocket dispersers and other embodiments of dynamic mixers, high-pressure homogenizers, pumps with downstream nozzles, valves, membranes or other narrow slit geometries, static mixers, in-line mixers using rotor-stator blades (Ultra-Turrax, inline dissolver), micro-mixing systems and ultrasonic emulsifiers.

The formulations provided herein containing solavetivone, 5-epi-β-vetivone or derivative or analog thereof can be prepared in any known manner known in the art, for instance by blending the compositions with conventional liquid carriers and/or dispersible solid carriers. Dispersing and/or emulsifying agents, such as surface active agents, can be included to facilitate formulation, and if used, the amount of dispersing and/or emulsifying agents used is dictated by the nature of the composition and the ability of the agent to facilitate the dispersion of the components in the formulation. The compositions provided herein can be formulated for topical administration to a subject, or for administration to a surface or a locus to be treated.

I. EXAMPLES

The following examples are included for illustrative purposes only and are not intended to limit the scope of the invention.

Example 1

Solavetivone as a Repellent for Bed Bugs

A formulation, containing 0.5% solavetivone and 0.1% butylated hydroxytoluene (BHT) in acetone was tested for efficacy for repelling adult bed bugs (*Cimex lectularius*).

A. Bed Bug Repellency of 0.5% Solavetivone in Acetone

Treatment chambers were created by cutting a circular hole in the bottom of 9-cm Petri dishes. A fine mesh nylon cloth was then glued to Petri dishes, covering the holes. The chambers were formed using the inverted Petri dishes with the screened bottoms serving as the tops and the lids forming the base of the chambers. The lids were secured with rubber bands.

Five semi-circular pieces of filter paper, with a diameter of 9 cm were arranged so that they were evenly spaced on a sheet of aluminum foil. One (1) mL of 0.5% solavetivone solution, stored at ambient temperature and humidity, was applied to the filter papers. Five untreated semi-circular pieces were marked with the letter "c", for control, on both sides in pencil or solvent resistant ink. One solavetivone-treated filter paper and one untreated filter paper were placed with the flat sides against each other, creating a full circle, in the lids of five 9-cm Petri dishes, serving as the treatment chambers described above, such that the entire surface of the lid was covered. Prior to addition of the bed bugs, the filter papers were confirmed to be completely dry and free of any residual acetone odor. Ten (10) bed bugs, having received a blood meal no more than 7 days before, were placed onto the untreated piece of paper and covered with the ventilated base of the Petri dish. The containers of each replicate were then kept at ambient laboratory temperature and humidity for the duration of the study. The distribution of the bed bugs on the treated and untreated filter papers was recorded at 0.5, 1, 1.5, 2, and 24 hours after being placed in the containers. Observations were made in darkness with the aid of a red lens flashlight. Gloves and a dust mask were worn by the observer to reduce detection of the bed bugs and to minimize disturbance caused by the observer. Five additional treatment chambers were created as described above, except the treated filter paper was soaked with acetone with 0.1% BHT (control treatment), instead of the 0.5% solavetivone solution. Bed bug distribution in the control chambers were recorded as described for the treatment condition.

The solavetivone treatment repellency was calculated from the following equation: $R=[(C-T)/C]*100$, where R is the % repellency, C is the fraction of bed bugs on the acetone-treated filter papers, and T is the fraction of bed bugs on the solavetivone-treated filter papers. Results indicating the efficacy of 0.5% solavetivone for repelling bed bugs is set forth in Table 2 below. The results show that 0.5% solavetivone is sufficient to repel bed bugs for at least 24 hours following treatment.

TABLE 2

Bedbug repellency solavetivone at 0.5% and acetone stabilized with 0.1% BHT, Day 1

| | Control | | | Treatment | | | Repellancy | |
|---|---|---|---|---|---|---|---|---|
| Time (hr) | # Bed Bugs | Acetone | Blank | # Bed Bugs | Solavetivone | Untreated | Control Repellancy | Solavetivone Repellancy |
| 0.5 | 50 | 28 | 22 | 50 | 4 | 50 | 44.0% | 92.0% |
| 1.0 | 50 | 28 | 22 | 50 | 5 | 50 | 44.0% | 90.0% |
| 1.5 | 50 | 33 | 17 | 50 | 4 | 50 | 34.0% | 92.0% |
| 2.0 | 50 | 33 | 17 | 50 | 2 | 50 | 34.0% | 96.0% |
| 24.0 | 50 | 21 | 29 | 50 | 1 | 50 | 58.0% | 98.0% |
| Averages | 50 | 28.6 | 21.4 | 50 | 3.2 | 50.0 | 42.8% | 93.6% |
| t-test acetone control versus blank | | | | | | | 0.1778 | |
| t-test solavetivone versus acetone control | | | | | | | 0.0002 | |

B. Extended Bed Bug Repellency of 0.5% Solavetivone in Acetone

The bed bug (*Cimex lectularius*) treatment chambers described in part A above were used to test the duration of 0.5% solavetivone in acetone repellent effects. At the end of 24 hours, the old bed bugs were removed from each Petri dish and 10 new bed bugs were added to each dish, for a total of 50 bed bugs. The distribution of the new set of bed bugs was recorded at 0.5, 1, 1.5, 2, and 24 hours after their introduction to the chamber (Day 2). Observations were made and repellency was calculated as described in Section A above. The results are shown in Table 3 below. The results show that 0.5% solavetivone is sufficient to repel bed bugs for at least 48 hours following treatment.

TABLE 3

Bedbug repellency solavetivone at 0.5% and acetone stabilized with 0.1% BHT, Day 2

| | Control | | | Treatment | | | Repellancy | |
|---|---|---|---|---|---|---|---|---|
| Time (hr) | # Bed Bugs | Acetone | Blank | # Bed Bugs | Solavetivone | Untreated | Control Repellancy | Solavetivone Repellancy |
| 0.5 | 50 | 20 | 30 | 50 | 2 | 43 | 60.0% | 96.0% |
| 1.0 | 50 | 23 | 27 | 50 | 2 | 44 | 54.0% | 96.0% |
| 1.5 | 50 | 30 | 20 | 50 | 6 | 47 | 40.0% | 88.0% |
| 2.0 | 50 | 29 | 21 | 50 | 5 | 49 | 42.0% | 90.0% |
| 24.0 | 50 | 22 | 28 | 50 | 5 | 46 | 56.0% | 90.0% |
| Averages | 50 | 24.8 | 25.2 | 50 | 4.0 | 45.8 | 50.4% | 92.0% |
| t-test acetone control versus blank | | | | | | | 0.9246 | |
| t-test solavetivone versus acetone control | | | | | | | 0.0001 | |

Example 2

5-Epi-β-Vetivone as a Repellent for Bed Bugs

A formulation, containing 0.5% 5-epi-β-vetivone and 0.1% butylated hydroxytoluene (BHT) in acetone was tested for efficacy for repelling adult bed bugs (*Cimex lectularius*).

A. Bed Bug Repellency of 0.5% 5-Epi-β-Vetivone in Acetone

Treatment chambers were prepared as described in Example 1A. Five semi-circular pieces of filter paper, with a diameter of 9 cm were arranged so that they were evenly spaced on a sheet of aluminum foil. One (1) mL of 0.5% 5-epi-β-vetivone solution, stored at ambient temperature and humidity, was applied to the filter papers. Five untreated semi-circular pieces were marked with the letter "c", for control, on both sides in pencil or solvent resistant ink. One 5-epi-β-vetivone-treated filter paper and one untreated filter paper were placed with the flat sides against each other, creating a full circle, in the lids of five 9-cm Petri dishes, serving as the treatment chambers described above, such that the entire surface of the lid was covered. Prior to addition of the bed bugs, the filter papers were confirmed to be completely dry and free of any residual acetone odor. Ten (10) bed bugs, having received a blood meal no more than 7 days before, were placed onto the untreated piece of paper and covered with the ventilated base of the Petri dish. The containers of each replicate were then kept at ambient laboratory temperature and humidity for the duration of the study. The distribution of the bed bugs on the treated and untreated filter papers was recorded at 0.5, 1, 1.5, 2, and 24 hours after being placed in the containers. Observations were made in darkness with the aid of a red lens flashlight. Gloves and a dust mask were worn by the observer to reduce detection of the bed bugs and to minimize disturbance caused by the observer. Five additional treatment chambers were created as described above, except the treated filter paper was soaked with acetone with 0.1% BHT (control treatment), instead of the 0.5% 5-epi-β-vetivone solution. Bed bug distribution in the control chambers were recorded as described for the treatment condition.

The 5-epi-β-vetivone treatment repellency was calculated from the following equation: R=[(C−T)/C]*100, where R is the % repellency, C is the fraction of bed bugs on the isopropanol-treated filter papers, and T is the fraction of bed bugs on the 5-epi-β-vetivone-treated filter papers. Results indicating the efficacy of 0.5% 5-epi-β-vetivone for repelling bed bugs is set forth in Table 4 below. The results show that 0.5% 5-epi-β-vetivone is sufficient to repel bed bugs for at least 24 hours following treatment.

TABLE 4

Bedbug repellency 5-epi-β-vetivone at 0.5% and acetone stabilized with 0.1% BHT, Day 1

| | Control | | | Treatment | | | Repellancy | |
|---|---|---|---|---|---|---|---|---|
| Time (hr) | # Bed Bugs | Acetone | Blank | # Bed Bugs | 5-epi-β-vetivone | Untreated | Control Repellancy | 5-epi-β-vetivone Repellancy |
| 0.5 | 50 | 28 | 22 | 50 | 6 | 44 | 44.0% | 88.0% |
| 1.0 | 50 | 28 | 22 | 50 | 3 | 47 | 44.0% | 94.0% |
| 1.5 | 50 | 33 | 17 | 50 | 1 | 49 | 34.0% | 98.0% |
| 2.0 | 50 | 33 | 17 | 50 | 2 | 48 | 34.0% | 96.0% |
| 24.0 | 50 | 21 | 29 | 50 | 0 | 50 | 58.0% | 100.0% |
| Averages | 50 | 28.6 | 21.4 | 50 | 2.4 | 47.6 | 42.8% | 95.2% |
| t-test acetone control versus blank | | | | | | | 0.1778 | |
| t-test 5-epi-β-vetivone versus acetone control | | | | | | | 0.0003 | |

B. Extended Bed Bug Repellency of 0.5% 5-Epi-β-Vetivone in Acetone

The bed bug (*Cimex lectularius*) treatment chambers described in part A above were used to test the duration of 0.5% 5-epi-β-vetivone in acetone repellent effects. At the end of 24 hours, the old bed bugs were removed from each Petri dish and 10 new bed bugs were added to each dish, for a total of 50 bed bugs. The distribution of the new set of bed bugs was recorded at 0.5, 1, 1.5, 2, and 24 hours after their introduction to the chamber (Day 2). Observations were made and repellency was calculated as described in Section A above. The results are shown in Table 5 below. The results show that 0.5% 5-epi-β-vetivone is sufficient to repel bed bugs for at least 48 hours following treatment.

TABLE 5

Bedbug repellency 5-epi-β-vetivone at 0.5% and acetone stabilized with 0.1% BHT, Day 2

| | Control | | | Treatment | | | Repellancy | |
|---|---|---|---|---|---|---|---|---|
| Time (hr) | # Bed Bugs | Acetone | Blank | # Bed Bugs | 5-epi-β-vetivone | Untreated | Control Repellancy | 5-epi-β-vetivone Repellancy |
| 0.5 | 50 | 20 | 30 | 50 | 4 | 46 | 60.0% | 92.0% |
| 1.0 | 50 | 23 | 27 | 50 | 3 | 47 | 54.0% | 94.0% |
| 1.5 | 50 | 30 | 20 | 50 | 3 | 47 | 40.0% | 94.0% |
| 2.0 | 50 | 29 | 21 | 50 | 4 | 46 | 42.0% | 92.0% |
| 24.0 | 50 | 22 | 28 | 50 | 2 | 48 | 56.0% | 96.0% |
| Averages | 50 | 24.8 | 25.2 | 50 | 3.2 | 46.8 | 50.4% | 93.6% |
| t-test acetone control versus blank | | | | | | | 0.9246 | |
| t-test 5-epi-β-vetivone versus acetone control | | | | | | | 0.0004 | |

Since modifications will be apparent to those of skill in this art, it is intended that this invention be limited only by the scope of the appended claims.

The invention claimed is:

1. A method for repelling or killing pests, comprising:

contacting a pest with solavetivone, 5-epi-β-vetivone ((5S,10R)-5-epi-β-vetivone)) or a derivative of either solavetivone or 5-epi-β-vetivone, or mixtures of any of the foregoing, whereby the pest is repelled or killed, wherein:

the derivative is a modified or partially substituted solavetivone or 5-epi-β-vetivone that retains pest repelling or killing activity;

the pest is an arthropod.

2. The method of claim 1 comprising:

providing an amount of a composition comprising solavetivone, 5-epi-β-vetivone or a derivative of either solavetivone or 5-epi-β-vetivone, or mixtures thereof to a location in which the pest occurs, wherein the amount is sufficient to repel or kill the pest; and deploying the composition at the location, whereby the pest is repelled from the location or dies after coming in contact with the composition.

3. The method of claim 1, wherein the solavetivone, 5-epi-β-vetivone or a derivative thereof is present in an amount of at least about 0.1%, by weight, of the composition.

4. The method of claim 1, wherein the derivative is 3-hydroxysolavetivone, 3,9-dihydroxysolavetivone, 3-hydroxy-9-(3-methyl-2-butenoyloxy)solavetivone, 3-acetoxysolavetivone, 13-hydroxysolavetivone, 3-acetoxy-9-(2-methylpropionyloxy)solavetivone, 3-hydroxy-9-(3-methylbutanoyloxy)solavetivone, 3-acetoxy-9-(3-methylbutanoyloxy)-solavetivone, 3-acetoxy-9-(3-methyl-2-butenoyloxy)solavetivone, 3-hydroxy-9-tigloyloxysolavetivone, 3-hydroxy-9-isobutanoyloxysolavetivone, 3-beta-acetoxysolavetivone or 3-beta-hydroxysolavetivone.

5. The method of claim 2, wherein the deploying step comprises applying topically, atomizing, brushing on, coating, dipping, drenching, dripping, dusting, foaming, infusing, injecting into or onto, pouring, rolling on, scattering, spraying, spreading, sprinkling or wiping the composition onto at least a portion of the location.

6. The method of claim 2, wherein the location is surface of a human or animal body.

7. The method of claim 2, wherein the composition is deployed by spraying or applying topically to an article of clothing of a human.

8. The method of claim 2, wherein the composition is provided as an aerosol, a solution, an emulsion or an oil.

9. The method of claim 8, wherein the composition is a lotion, a soap, a spray or a gel.

10. The method of claim 2, wherein the location is a bedding location.

11. The method of claim 2, wherein the composition is formulated to form a viscous fluid or gel when dispensed and applied to the pest.

12. The method of claim 1, wherein the pest is ants, bedbugs, carpet beetles, centipedes, chiggers, drain flies, dust mites, earwigs, fleas, flies, gnats, hornets, lice, millipedes, mites, mosquitoes, scabies, silverfish, spiders, stinkbugs, termites, ticks, wasps, weevils or yellow jackets.

13. The method of claim 1, wherein the composition contacted with locus of the pest for a period of time that is at least 1 hour, 2 hours, 3 hours, 4 hours, 5 hours, 6, hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, at least 1 day, 2 days, 3 days, 4 days, 5 days, 6 days 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, at least 45 days, at least 60 days, at least 75 days, at least 90 days, at least 4 months, at least 5 months, at least 6 months, at least 7 months, at least 8 months, at least 9 months, at least 10 months, at least 11 months or at least 1 year.

14. The method of claim 2, wherein the composition further comprises a carrier that is present in an amount between at least about 0.1% and least about 99.9%, or between at least about 10% and at least about 80%, or between at least about 20% and at least about 70%, or between at least about 30% and at least about 60%, or between at least about 10% and at least about 40%, or between at least about 30% and at least about 70%, or between at least about 60% and at least about 90%, by weight, of the composition.

15. The method of claim 14, wherein the carrier is water, an alcohol, an aldehyde, an alkane, an alkene, an amide, an amine, a diglyceride, an ester, an ether, a glycol ether, a fat, a fatty acid, a glycol ester, a ketone, lanolin, mineral oil, a monoglyceride, paraffin oil, a polyethylene glycol, petrolatum, a propylene carbonate, silicone, tall oils, a terpene hydrocarbon, a terpene alcohol, a triglyceride, finely divided organic solid material, finely divided inorganic solid materials, or mixtures thereof.

16. The method of claim 2, wherein the composition further comprises a dispersing agent.

17. The method of claim 16, wherein the dispersing agent is a surfactant, polyvinylpyrrolidone, polyoxyethylated castor oil, a polyoxyethylene sorbitan ester, alkylnaphthalene sulfonate, alkylbenzenesulfonate, polyoxyethylene, polycarboxylate, lignin sulfonate, sodium silicate, potassium silicate, methylcellulose, carboxymethyl cellulose, hydroxypropylcellulose, hydroxypropyl-methylcellulose, gum arabic, a polyacrylate, and an acrylic/maleic copolymers, or combinations thereof.

18. The method of claim 16, wherein the dispersing agent is present in an amount of between at or about 0.002% and at or about 50%, or between at or about 0.025% and at or about 25%, or between at or about 0.01% and at or about 15%, by weight, of the composition.

19. The method of claim 2, wherein the composition further comprises a viscosity modulating agent.

20. The method of claim 19, wherein the viscosity modulating agent is an acrylate, an acrylate copolymer, an alginate, an arabinogalactan, a carrageenan, a cellulosic polymer, a ceramide, chitan, dextran, diutan, fucelleran, fucoidan, a β-glucan, a gellan gum, guar gum, gum arabic, gum ghatti, gum tragacanth, karaya gum, laminaran, locust bean gum, a methacrylate, a methyl methacrylate, modified starch, pectin, propylene glycol alginate, psyllium gum, polyvinyl pyrrolidone, rhamsan gum, scleroglucan, starch, starch hydroxyethyl ether, starch dextrins and xanthan gum, or combinations thereof.

21. The method of claim 19, wherein the viscosity modulating agent is present in an amount of between at or about 0.05% and at or about 25%, or between at or about 0.1% and at or about 10%, or between at or about 0.5% and at or about 5%, by weight, of the composition.

22. The method of claim 2, wherein the composition further comprises a gelling agent.

23. The method of claim 22, wherein the gelling agent is agar, a carbomer, carboxyvinyl polymers, dibenzylidene alditols, collagen, dextrin fatty acid esters, gelatin, hydrogenated styrene/isoprene copolymers, 12-hydroxystearic acid, κ-carrageenan, gellan gum, pectin, polyacrylic acids, styrene-ethylene/propylene block copolymers, styrene-ethylene/butylene-styrene block copolymers, sucrose fatty acid esters or a wax, or combinations thereof.

24. The method of claim 22, wherein the gelling agent is present in an amount between at or about 0.01% and at or about 10%, between at or about 0.05% and at or about 7.5%, between at or about 0.1% and at or about 5%, or between at or about 0.25% and at or about 2.5%, by weight, of the composition.

25. The method of claim 2, wherein the composition further comprises an antioxidant.

26. The method of claim 25, wherein the antioxidant is ascorbyl palmitate, butylated p-cresol, tert-butylhydroquinone, butylated hydroquinone monomethyl ether, butylhydroxyanisole, butylhydroxytoluene, propyl gallate or a tocopherol, or combinations thereof.

27. The method of claim 25, wherein the antioxidant is present in an amount between at or about 0.001% and at or about 5%, between at or about 0.005% and at or about 2.5%, or between at or about 0.01% and at or about 1%, by weight, of the composition.

28. The method of claim 2, wherein the composition further comprises a preservative.

29. The method of claim 28, wherein the preservative is azoles, benzisothiazolin-3-one, benzalkonium quaternary compounds, benzyl alcohol, borates, 2-bromo-2-nitro-propane-1,3-diol, butylparaben, 5-chloro-2-methyl-4-isothiazolin-3-one, chlorphenesin, chloroxylenol, diazolidinyl urea, a dimethyl-benzylalkyl-ammonium chloride, ethylparaben, formaldehyde, glutaraldehyde, halogenated salicylanilides, hexachlorophene, isobutylparaben, isothiazolin-3-one, 2-methyl-4-isothiazoline-3-one, methylparaben, monochloracetamide, neomycin sulfate, o-phenylphenol and salts thereof, phenoxyethanol, propionic acid and salts thereof, propylparaben, sodium benzoate, sorbic acid and salts thereof, tebuconazole or triazoles, or combinations thereof.

30. The method of claim 28, wherein the preservative is present in an amount between at or about 0.001% and at or about 5%, or between at or about 0.005% and at or about 2.5%, or between at or about 0.01% to at or about 1%, by weight, of the composition.

31. The method of claim 2, wherein the composition further comprises a colorant.

32. The method of claim 31, wherein the colorant is a dye or pigment.

33. The method of claim 31, wherein the colorant is present in an amount between at or about 0.0001% and at or about 1%, or between at or about 0.0005% and at or about 0.5%, by weight, of the composition.

34. The method of claim 2, wherein the composition further comprises a synergist.

35. The method of claim 34, wherein the synergist is bis-(2,3,3,3-tetrachloropropyl)ether, dodecyl imidazole, N-(2-ethylhexyl)bicyclo-[2,2,1]hept-5-ene-2,3-dicarboxyimide piperonyl butoxide, isobornyl thiocyanatoacetate, safroxan or sesame, or combinations thereof.

36. The method of claim 34, wherein the synergist is present in an amount of at or about 1% to at or about 50%, by weight, of the composition.

37. The method of claim 2, wherein the composition further comprises a penetration agent.

38. The method of claim 37, wherein the penetration agent is silicone dioxide, petroleum distillate, light solvent naphtha or D-limonene, or combinations thereof.

39. The method of claim 37, wherein the penetration agent is present in an amount of at or about 0.001% to at or about 50%, by weight, of the composition.

40. The method of claim 2 wherein the composition is formulated as a personal care or cosmetic composition.

41. The method of claim 2 wherein the composition is formulated as a household care product.

42. The method of claim 11, wherein the composition further comprises at least or about at least 0.2 to at least or about at least 5% gelling agent that is agar, an alginate, a carbomer, carboxyvinyl polymers, dibenzylidene alditols, carboxypolymethylene, collagen, dextrin fatty acid esters, gelatin, hydrogenated styrene/isoprene copolymers, 12-hydroxystearic acid, κ-carrageenan, gellan gum, a lower hydroxy cellulose, pectin, polyacrylic acids, styrene-ethylene/propylene block copolymers, styrene-ethylene/butylene-styrene block copolymers, sucrose fatty acid esters or a wax or combinations thereof.

43. The method of claim 2, wherein the composition further comprises an additional compound that repels and/or kills pests that is N,N-diethyl-meta-toluamide, picaridin (2-(2-hydroxyethyl)-1-piperidinecarboxylic acid 1-methylpropyl ester), citronella oil, camphor oil, cedarwood oil, coumarin, 2-hydroxy-methylcyclohexyl acetic acid lactone, beta-alanine, 2-hydroxymethyl-cyclohexylidene acetic acid lactone, 2-hydroxy-methylcyclohexyl propionic acid lactone, p-menthane-3,8-diol, or 3-[N-butyl-N-acetyl]-aminopropionic acid ethyl ester, or combinations thereof.

44. The method of claim 43, wherein the additional compound that repels and/or kills pests is present in an amount of at least or about at least 0.1% and at least or about at least 25%, by weight, of the composition.

* * * * *

SEQUENCE LISTING

<160> NUMBER OF SEQ ID NOS: 3

<210> SEQ ID NO 1
<211> LENGTH: 555
<212> TYPE: PRT
<213> ORGANISM: Hyoscyamus muticus
<220> FEATURE:
<223> OTHER INFORMATION: Premnaspirodiene synthase

<400> SEQUENCE: 1

Met Ala Pro Ala Ile Val Met Ser Asn Tyr Glu Glu Glu Glu Ile Val
1 5 10 15

Arg Pro Val Ala Asp Phe Ser Pro Ser Leu Trp Gly Asp His Phe His
20 25 30

Ser Phe Ser Val Asp Asn Gln Val Ala Glu Lys Tyr Ala Gln Glu Ile
35 40 45

Glu Thr Leu Lys Glu Gln Thr Ser Thr Met Leu Ser Ala Ala Cys Gly
50 55 60

```
Thr Thr Leu Thr Glu Lys Leu Asn Leu Ile Asp Ile Ile Glu Arg Leu
65                  70                  75                  80

Gly Ile Ala Tyr His Phe Glu Lys Gln Ile Glu Asp Met Leu Asp His
                85                  90                  95

Ile Tyr Arg Ala Asp Pro Tyr Phe Glu Ala His Glu Tyr Asn Asp Leu
            100                 105                 110

Asn Thr Ser Ser Val Gln Phe Arg Leu Leu Arg Gln His Gly Tyr Asn
        115                 120                 125

Val Ser Pro Asn Ile Phe Ser Arg Phe Gln Asp Ala Asn Gly Lys Phe
    130                 135                 140

Lys Glu Ser Leu Arg Ser Asp Ile Arg Gly Leu Leu Asn Leu Tyr Glu
145                 150                 155                 160

Ala Ser His Val Arg Thr His Lys Glu Asp Ile Leu Glu Glu Ala Leu
                165                 170                 175

Val Phe Ser Val Gly His Leu Glu Ser Ala Ala Pro His Leu Lys Ser
            180                 185                 190

Pro Leu Ser Lys Gln Val Thr His Ala Leu Glu Gln Ser Leu His Lys
        195                 200                 205

Ser Ile Pro Arg Val Glu Ile Arg Tyr Phe Ile Ser Ile Tyr Glu Glu
    210                 215                 220

Glu Glu Phe Lys Asn Asp Leu Leu Leu Arg Phe Ala Lys Leu Asp Tyr
225                 230                 235                 240

Asn Leu Leu Gln Met Leu His Lys His Glu Leu Ser Glu Val Ser Arg
                245                 250                 255

Trp Trp Lys Asp Leu Asp Phe Val Thr Thr Leu Pro Tyr Ala Arg Asp
            260                 265                 270

Arg Ala Val Glu Cys Tyr Phe Trp Thr Met Gly Val Tyr Ala Glu Pro
        275                 280                 285

Gln Tyr Ser Gln Ala Arg Val Met Leu Ala Lys Thr Ile Ala Met Ile
    290                 295                 300

Ser Ile Val Asp Asp Thr Phe Asp Ala Tyr Gly Ile Val Lys Glu Leu
305                 310                 315                 320

Glu Val Tyr Thr Asp Ala Ile Gln Arg Trp Asp Ile Ser Gln Ile Asp
                325                 330                 335

Arg Leu Pro Glu Tyr Met Lys Ile Ser Tyr Lys Ala Leu Leu Asp Leu
            340                 345                 350

Tyr Asp Asp Tyr Glu Lys Glu Leu Ser Lys Asp Gly Arg Ser Asp Val
        355                 360                 365

Val His Tyr Ala Lys Glu Arg Met Lys Glu Ile Val Gly Asn Tyr Phe
    370                 375                 380

Ile Glu Gly Lys Trp Phe Ile Glu Gly Tyr Met Pro Ser Val Ser Glu
385                 390                 395                 400

Tyr Leu Ser Asn Ala Leu Ala Thr Ser Thr Tyr Tyr Leu Leu Thr Thr
                405                 410                 415

Thr Ser Tyr Leu Gly Met Lys Ser Ala Thr Lys Glu His Phe Glu Trp
            420                 425                 430

Leu Ala Thr Asn Pro Lys Ile Leu Glu Ala Asn Ala Thr Leu Cys Arg
        435                 440                 445

Val Val Asp Asp Ile Ala Thr Tyr Glu Val Glu Lys Gly Arg Gly Gln
    450                 455                 460

Ile Ala Thr Gly Ile Glu Cys Tyr Met Arg Asp Tyr Gly Val Ser Thr
465                 470                 475                 480
```

```
Glu Val Ala Met Glu Lys Phe Gln Glu Met Ala Asp Ile Ala Trp Lys
                485                 490                 495

Asp Val Asn Glu Glu Ile Leu Arg Pro Thr Pro Val Ser Ser Glu Ile
            500                 505                 510

Leu Thr Arg Ile Leu Asn Leu Ala Arg Ile Ile Asp Val Thr Tyr Lys
        515                 520                 525

His Asn Gln Asp Gly Tyr Thr His Pro Glu Lys Val Leu Lys Pro His
    530                 535                 540

Ile Ile Ala Leu Val Val Asp Ser Ile Asp Ile
545                 550                 555


<210> SEQ ID NO 2
<211> LENGTH: 502
<212> TYPE: PRT
<213> ORGANISM: Hyoscyamus muticus
<220> FEATURE:
<223> OTHER INFORMATION: premnaspirodiene oxygenase

<400> SEQUENCE: 2

Met Gln Phe Phe Ser Leu Val Ser Ile Phe Leu Phe Leu Ser Phe Leu
 1               5                  10                  15

Phe Leu Leu Arg Lys Trp Lys Asn Ser Asn Ser Gln Ser Lys Lys Leu
            20                  25                  30

Pro Pro Gly Pro Trp Lys Leu Pro Leu Leu Gly Ser Met Leu His Met
        35                  40                  45

Val Gly Gly Leu Pro His His Val Leu Arg Asp Leu Ala Lys Lys Tyr
    50                  55                  60

Gly Pro Leu Met His Leu Gln Leu Gly Glu Val Ser Ala Val Val Val
65                  70                  75                  80

Thr Ser Pro Asp Met Ala Lys Glu Val Leu Lys Thr His Asp Ile Ala
                85                  90                  95

Phe Ala Ser Arg Pro Lys Leu Leu Ala Pro Glu Ile Val Cys Tyr Asn
            100                 105                 110

Arg Ser Asp Ile Ala Phe Cys Pro Tyr Gly Asp Tyr Trp Arg Gln Met
        115                 120                 125

Arg Lys Ile Cys Val Leu Glu Val Leu Ser Ala Lys Asn Val Arg Ser
    130                 135                 140

Phe Ser Ser Ile Arg Arg Asp Glu Val Leu Arg Leu Val Asn Phe Val
145                 150                 155                 160

Arg Ser Ser Thr Ser Glu Pro Val Asn Phe Thr Glu Arg Leu Phe Leu
                165                 170                 175

Phe Thr Ser Ser Met Thr Cys Arg Ser Ala Phe Gly Lys Val Phe Lys
            180                 185                 190

Glu Gln Glu Thr Phe Ile Gln Leu Ile Lys Glu Val Ile Gly Leu Ala
        195                 200                 205

Gly Gly Phe Asp Val Ala Asp Ile Phe Pro Ser Leu Lys Phe Leu His
    210                 215                 220

Val Leu Thr Gly Met Glu Gly Lys Ile Met Lys Ala His His Lys Val
225                 230                 235                 240

Asp Ala Ile Val Glu Asp Val Ile Asn Glu His Lys Lys Asn Leu Ala
                245                 250                 255

Met Gly Lys Thr Asn Gly Ala Leu Gly Gly Glu Asp Leu Ile Asp Val
            260                 265                 270

Leu Leu Arg Leu Met Asn Asp Gly Gly Leu Gln Phe Pro Ile Thr Asn
        275                 280                 285
```

```
Asp Asn Ile Lys Ala Ile Ile Phe Asp Met Phe Ala Ala Gly Thr Glu
    290                 295                 300

Thr Ser Ser Ser Thr Leu Val Trp Ala Met Val Gln Met Met Arg Asn
305                 310                 315                 320

Pro Thr Ile Leu Ala Lys Ala Gln Ala Glu Val Arg Glu Ala Phe Lys
                325                 330                 335

Gly Lys Glu Thr Phe Asp Glu Asn Asp Val Glu Glu Leu Lys Tyr Leu
            340                 345                 350

Lys Leu Val Ile Lys Glu Thr Leu Arg Leu His Pro Pro Val Pro Leu
        355                 360                 365

Leu Val Pro Arg Glu Cys Arg Glu Glu Thr Glu Ile Asn Gly Tyr Thr
    370                 375                 380

Ile Pro Val Lys Thr Lys Val Met Val Asn Val Trp Ala Leu Gly Arg
385                 390                 395                 400

Asp Pro Lys Tyr Trp Asp Asp Ala Asp Asn Phe Lys Pro Glu Arg Phe
                405                 410                 415

Glu Gln Cys Ser Val Asp Phe Ile Gly Asn Asn Phe Glu Tyr Leu Pro
            420                 425                 430

Phe Gly Gly Gly Arg Arg Ile Cys Pro Gly Ile Ser Phe Gly Leu Ala
        435                 440                 445

Asn Val Tyr Leu Pro Leu Ala Gln Leu Leu Tyr His Phe Asp Trp Lys
    450                 455                 460

Leu Pro Thr Gly Met Glu Pro Lys Asp Leu Asp Leu Thr Glu Leu Val
465                 470                 475                 480

Gly Val Thr Ala Ala Arg Lys Ser Asp Leu Met Leu Val Ala Thr Pro
                485                 490                 495

Tyr Gln Pro Ser Arg Glu
            500


<210> SEQ ID NO 3
<211> LENGTH: 504
<212> TYPE: PRT
<213> ORGANISM: Nicotiana tabacum
<220> FEATURE:
<223> OTHER INFORMATION: 5-epi-aristolochene dihydroxylase

<400> SEQUENCE: 3

Met Gln Phe Phe Ser Leu Val Ser Ile Phe Leu Phe Leu Ser Phe Leu
 1               5                  10                  15

Phe Leu Leu Arg Lys Trp Lys Asn Ser Asn Ser Gln Ser Lys Lys Leu
            20                  25                  30

Pro Pro Gly Pro Trp Lys Ile Pro Ile Leu Gly Ser Met Leu His Met
        35                  40                  45

Ile Gly Gly Glu Pro His His Val Leu Arg Asp Leu Ala Lys Lys Tyr
    50                  55                  60

Gly Pro Leu Met His Leu Gln Leu Gly Glu Ile Ser Ala Val Val Val
65                  70                  75                  80

Thr Ser Arg Asp Met Ala Lys Glu Val Leu Lys Thr His Asp Val Val
                85                  90                  95

Phe Ala Ser Arg Pro Lys Ile Val Ala Met Asp Ile Ile Cys Tyr Asn
            100                 105                 110

Gln Ser Asp Ile Ala Phe Ser Pro Tyr Gly Asp His Trp Arg Gln Met
        115                 120                 125

Arg Lys Ile Cys Val Met Glu Leu Leu Asn Ala Lys Asn Val Arg Ser
    130                 135                 140
```

-continued

```
Phe Ser Ser Ile Arg Arg Asp Glu Val Val Arg Leu Ile Asp Ser Ile
145                 150                 155                 160

Arg Ser Asp Ser Ser Ser Gly Glu Leu Val Asn Phe Thr Gln Arg Ile
                165                 170                 175

Ile Trp Phe Ala Ser Ser Met Thr Cys Arg Ser Ala Phe Gly Gln Val
            180                 185                 190

Leu Lys Gly Gln Asp Ile Phe Ala Lys Lys Ile Arg Glu Val Ile Gly
        195                 200                 205

Leu Ala Glu Gly Phe Asp Val Val Asp Ile Phe Pro Thr Tyr Lys Phe
    210                 215                 220

Leu His Val Leu Ser Gly Met Lys Arg Lys Leu Leu Asn Ala His Leu
225                 230                 235                 240

Lys Val Asp Ala Ile Val Glu Asp Val Ile Asn Glu His Lys Lys Asn
                245                 250                 255

Leu Ala Ala Gly Lys Ser Asn Gly Ala Leu Gly Gly Glu Asp Leu Ile
            260                 265                 270

Asp Val Leu Leu Arg Leu Met Asn Asp Thr Ser Leu Gln Phe Pro Ile
        275                 280                 285

Thr Asn Asp Asn Ile Lys Ala Val Ile Val Asp Met Phe Ala Ala Gly
    290                 295                 300

Thr Glu Thr Ser Ser Thr Thr Thr Val Trp Ala Met Ala Glu Met Met
305                 310                 315                 320

Lys Asn Pro Ser Val Phe Thr Lys Ala Gln Ala Glu Val Arg Glu Ala
                325                 330                 335

Phe Arg Asp Lys Val Ser Phe Asp Glu Asn Asp Val Glu Glu Leu Lys
            340                 345                 350

Tyr Leu Lys Leu Val Ile Lys Glu Thr Leu Arg Leu His Pro Pro Ser
        355                 360                 365

Pro Leu Leu Val Pro Arg Glu Cys Arg Glu Asp Thr Asp Ile Asn Gly
    370                 375                 380

Tyr Thr Ile Pro Ala Lys Thr Lys Val Met Val Asn Val Trp Ala Leu
385                 390                 395                 400

Gly Arg Asp Pro Lys Tyr Trp Asp Asp Ala Glu Ser Phe Lys Pro Glu
                405                 410                 415

Arg Phe Glu Gln Cys Ser Val Asp Phe Phe Gly Asn Asn Phe Glu Phe
            420                 425                 430

Leu Pro Phe Gly Gly Gly Arg Arg Ile Cys Pro Gly Met Ser Phe Gly
        435                 440                 445

Leu Ala Asn Leu Tyr Leu Pro Leu Ala Gln Leu Leu Tyr His Phe Asp
    450                 455                 460

Trp Lys Leu Pro Thr Gly Ile Met Pro Arg Asp Leu Asp Leu Thr Glu
465                 470                 475                 480

Leu Ser Gly Ile Thr Ile Ala Arg Lys Gly Gly Leu Tyr Leu Asn Ala
                485                 490                 495

Thr Pro Tyr Gln Pro Ser Arg Glu
            500
```